United States Patent
Ishibashi et al.

(10) Patent No.: US 10,600,974 B2
(45) Date of Patent: Mar. 24, 2020

(54) IRIDIUM COMPLEX COMPOUND, PROCESS FOR PRODUCING THE COMPOUND, COMPOSITION INCLUDING THE COMPOUND, ORGANIC ELECTROLUMINESCENT ELEMENT, DISPLAY DEVICE, AND ILLUMINATOR

(71) Applicant: Mitsubishi Chemical Corporation, Chiyoda-ku (JP)

(72) Inventors: Koichi Ishibashi, Kanagawa (JP); Kazuhiro Nagayama, Kanagawa (JP); Hideji Komatsu, Kanagawa (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 370 days.

(21) Appl. No.: 15/175,225

(22) Filed: Jun. 7, 2016

(65) Prior Publication Data
US 2016/0293866 A1   Oct. 6, 2016

Related U.S. Application Data

(63) Continuation of application No. PCT/JP2014/082805, filed on Dec. 11, 2014.

(30) Foreign Application Priority Data

Dec. 12, 2013 (JP) ................. 2013-257200

(51) Int. Cl.
*H01L 51/00* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS

| 8,958,625 B1 | 2/2015 | Wehnes et al. |
| 2001/0019782 A1 | 9/2001 | Igarashi et al. |

(Continued)

FOREIGN PATENT DOCUMENTS

| CN | 101899296 A | 12/2010 |
| CN | 102503986 A | 6/2012 |

(Continued)

OTHER PUBLICATIONS

Machine English translation of JP 2012-074444 A. Jul. 3, 2018.*
(Continued)

*Primary Examiner* — Jay Yang
(74) *Attorney, Agent, or Firm* — Oblon, McClelland, Maier & Neustadt, L.L.P.

(57) ABSTRACT

The object of the invention is to provide an iridium complex compound which emits red light with a high luminescent quantum yield, a process for producing the compound, an organic electroluminescent element which employs the iridium complex compound and has a high luminescent efficiency, a display device, and an illuminator. The present invention relates to an iridium complex compound represented by the following formula (1), which contains a phenyl(iso)quinoline or phenylquinazoline ligand and a phenylazole ligand:

$$\text{Ir}(L^1)_m(L^2)_n(L^3)_{3-m-n} \qquad (1)$$

15 Claims, 1 Drawing Sheet

(51) Int. Cl.
*C07F 15/00* (2006.01)
*H01L 51/50* (2006.01)

(52) U.S. Cl.
CPC .......... C09K 2211/1007 (2013.01); C09K 2211/1011 (2013.01); C09K 2211/1029 (2013.01); C09K 2211/1033 (2013.01); C09K 2211/1037 (2013.01); C09K 2211/1044 (2013.01); C09K 2211/185 (2013.01); H01L 51/008 (2013.01); H01L 51/0052 (2013.01); H01L 51/0059 (2013.01); H01L 51/0067 (2013.01); H01L 51/0072 (2013.01); H01L 51/0081 (2013.01); H01L 51/5016 (2013.01); H01L 2251/5384 (2013.01)

(56) References Cited

U.S. PATENT DOCUMENTS

| | | |
|---|---|---|
| 2007/0040168 A1 | 2/2007 | Igarashi et al. |
| 2007/0122655 A1 | 5/2007 | Deaton et al. |
| 2009/0153037 A1 | 6/2009 | Kim et al. |
| 2009/0174316 A1 | 7/2009 | Kim et al. |
| 2009/0179555 A1 | 7/2009 | Kim et al. |
| 2009/0184631 A1 | 7/2009 | Kim et al. |
| 2010/0252822 A1 | 10/2010 | Takahashi |
| 2010/0270916 A1 | 10/2010 | Xia et al. |
| 2011/0274327 A1 | 11/2011 | Wehnes et al. |
| 2012/0068165 A1 | 3/2012 | Hayashi |
| 2012/0292601 A1 | 11/2012 | Kottas et al. |
| 2013/0051676 A1 | 2/2013 | Wehnes et al. |
| 2013/0202165 A1 | 8/2013 | Wehnes et al. |
| 2013/0208956 A1 | 8/2013 | Wehnes et al. |
| 2013/0208967 A1 | 8/2013 | Wehnes |
| 2013/0328019 A1 | 12/2013 | Xia et al. |
| 2015/0023580 A1 | 1/2015 | Wehnes et al. |
| 2015/0155502 A1 | 6/2015 | Ishibashi et al. |

FOREIGN PATENT DOCUMENTS

| | | |
|---|---|---|
| EP | 2 055 709 A2 | 5/2009 |
| EP | 2 055 709 A3 | 5/2009 |
| EP | 2 055 710 A1 | 5/2009 |
| JP | 2001-345183 A | 12/2001 |
| JP | 2003-192691 A | 7/2003 |
| JP | 2006-89398 A | 4/2006 |
| JP | 2006-290781 A | 10/2006 |
| JP | 2007-81388 A | 3/2007 |
| JP | 2009-137941 A | 6/2009 |
| JP | 2009-149607 A | 7/2009 |
| JP | 2009-173630 A | 8/2009 |
| JP | 2009-185017 A | 8/2009 |
| JP | 2010-278354 A | 12/2010 |
| JP | 2012-74444 A | 4/2012 |
| JP | 2012074444 A * | 4/2012 |
| JP | 2012074444 A * | 4/2012 |
| JP | 2012-525405 A | 10/2012 |
| TW | 201043627 A1 | 12/2010 |
| WO | WO 02/15645 A1 | 2/2002 |
| WO | WO 2009/034987 A1 | 3/2009 |
| WO | WO 2010/137411 A1 | 12/2010 |
| WO | WO 2011/137411 A1 | 11/2011 |
| WO | WO 2012/158851 A1 | 11/2012 |
| WO | WO 2014/024889 A1 | 2/2014 |

OTHER PUBLICATIONS

Machine English translation of JP 2001-345183 A. Jul. 3, 2018.*
Extended European Search Report dated Dec. 6, 2016 in patent application No. 14869968.9.
Combined Chinese Office Action and Search Report dated Apr. 2, 2018 in Chinese Patent Application No. 201480067335.3 (with English translation), 18 pages.
Extended European Search Report dated Oct. 28, 2016 in Patent Application No. 14869968.9.
International Search Report dated Mar. 3, 2015 in PCT/JP2014/082805 (with English translation).
M. A. Baldo, et al., "Highly efficient phosphorescent emission from organic electroluminescent devices", letters to nature, vol. 395, 1998, pp. 151-154.
M. A. Baldo, et al., "Very high-efficiency green organic light-emitting devices based on electrophosphorescence", Applied Physics Letters, vol. 75, No. 1, 1999, pp. 4-6.
Hartmut Yersin, "Highly Efficient OLEDs with Phosphorescent Materials", Wiley-VCH GmbH, 2008, pp. 148-151 and Cover Pages.
Akira Tsuboyama, et al., "Homoleptic Cyclometalated Iridium Complexes with Highly Efficient Red Phosphorescence and Application to Organic Light-Emitting Diode", Journal of the American Chemical Society, vol. 125, No. 42, 2003, pp. 12971-12979.
Qunbo MCI, et al., "A highly efficient red electrophosphorescent iridium(III) complex containing phenyl quinazoline ligand in polymer light-emitting diodes", Journal of the Materials Chemistry, vol. 22, 2012, pp. 6878-6884.
Hye Joo Lee, et al., "Homoleptic vs. Heteroleptic Orange Light-Emitting Iridium Complexes Chelated with Benzothiazole Derivatives", Mol. Cryst. Liq. Cryst., vol. 584, 2013, pp. 53-59.
Japanese Office Action dated Jun. 26, 2018 in Patent Application No. 2015-552523 (with English translation), 8 pages.
Chinese Office Action dated Feb. 27, 2019 in Chinese Patent Application No. 201480067335.3 (with English abstract), 14 pages.
Office Action in Japanese patent application No. 2015-552503 dated Jul. 9, 2019. (w/Machine Translation).
Decision on Rejection dated Sep. 30, 2019 in corresponding Chinese Application No. 201480067335.3 (w/English Translation).
Decision on Rejection dated Sep. 30, 2019 in corresponding Chinse Application No. 20148006733.5. (w/English Translation).

* cited by examiner

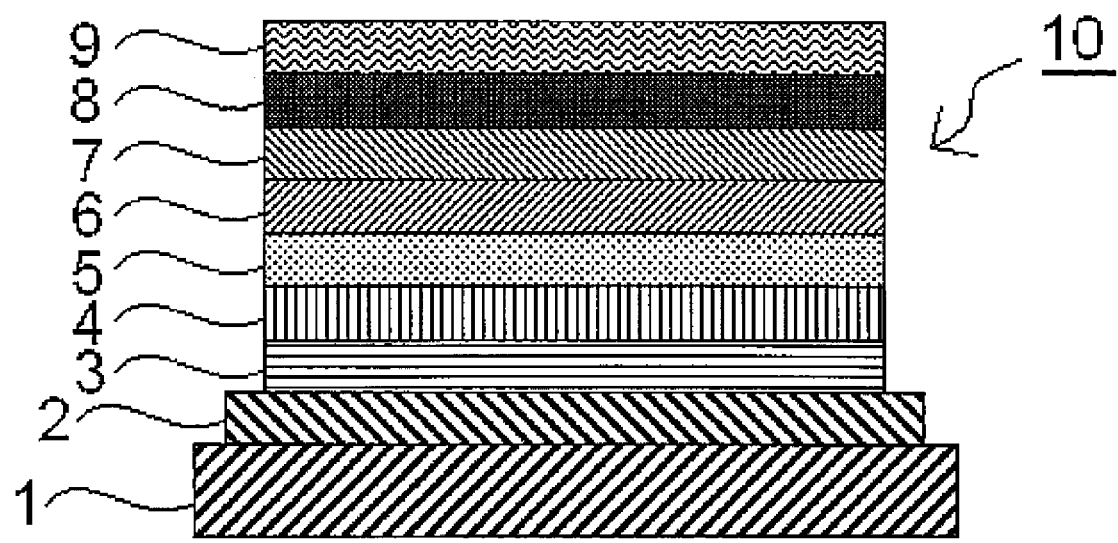

US 10,600,974 B2

IRIDIUM COMPLEX COMPOUND, PROCESS FOR PRODUCING THE COMPOUND, COMPOSITION INCLUDING THE COMPOUND, ORGANIC ELECTROLUMINESCENT ELEMENT, DISPLAY DEVICE, AND ILLUMINATOR

TECHNICAL FIELD

The present invention relates to an iridium complex compound. The invention relates to an iridium complex compound which emit phosphorescent red light with a high luminescent quantum yield, a process for producing the compound, a composition and an organic electroluminescent element which include the compound, and a display device and an illuminator which include the organic electroluminescent element.

BACKGROUND ART

Various electronic devices in which an organic electroluminescent element (hereinafter often referred to as "organic EL element") is utilized, such as organic EL illuminators and organic EL displays, are being put to practical use in recent years. Since organic EL elements are low in applied voltage and in power consumption, emit light areally, and are capable of emitting light of three primary colors, application thereof to illuminators and displays is being investigated enthusiastically. Improvements in luminescent efficiency are desired for that purpose.

As a means for improving the luminescent efficiency, it has been proposed to use a phosphorescent material in the emission layer of an organic EL element so as to utilize the phenomenon in which the recombination of holes with electrons yields singlet excitons and triplet excitons in a ratio of 1:3 (non-patent documents 1 and 2). Widely known as the phosphorescent material are, for example, ortho-metalized iridium complex compounds such as bis(2-phenylpyridinato-N,C2')iridium acetylacetonate (Ir(ppy)$_2$(acac)), tris(2-phynylpyridinato-N,C2')iridium (Ir(ppy)$_3$), and tris(1-phenylisoquinoline-N,C2')iridium (Ir(piq)$_3$) (non-patent documents 3 and 4). In particular, iridium complex compounds which emit phosphorescent red light are disclosed in non-patent documents 3 to 5 and patent documents 1 to 3, and organic EL elements employing these iridium compounds have been produced.

It is known that there is a strong correlation between the luminescent quantum yield of an iridium complex compound and the luminescent efficiency of an organic EL element produced using the compound. It is therefore necessary that an iridium complex compound having a high luminescent quantum yield should be developed for obtaining an organic EL element having a high luminescent efficiency.

PRIOR ART DOCUMENTS

Patent Documents

Patent Document 1: JP-A-2006-290781
Patent Document 2: U.S. Patent Application Publication No. 2007/0122655
Patent Document 3: Chinese Patent Application Publication No. 101899296

Non-Patent Documents

Non-Patent Document 1: Nature, Vol. 395, pp. 151-154, 1998
Non-Patent Document 2: Applied Physics Letters, Vol. 75, pp. 4-6, 1999
Non-Patent Document 3: H. Yersin, ed., Highly Efficient OLEDs with Phosphorescent Materials, WILEY-VCH GmbH, 2008
Non-Patent Document 4: Journal of the American Chemical Society, Vol. 125, pp. 12971-12979, 2003
Non-Patent Document 5: Journal of Materials Chemistry, Vol. 22, pp. 6878-6884, 2012

SUMMARY OF THE INVENTION

Problem that the Invention is to Solve

However, the phenyl(iso)quinoline-based red-phosphorescent material (patent document 1) and phenylquinazoline-based red-phosphorescent material (patent documents 2 and 3 and non-patent document 5) which have been used hitherto have low luminescent quantum yields as compared with green-phosphorescent materials, and organic EL elements produced using these compounds have a low luminescent efficiency. It has hence been desired to improve the luminescent quantum yields of the red-phosphorescent materials.

Subjects for the invention are: to provide an iridium complex compound which emit phosphorescent red light with a high luminescent quantum yield to overcome the problem; and to provide an organic electroluminescent element having a high luminescent efficiency and a display device and an illuminator which employ the organic electroluminescent element.

Means for Solving the Problem

The present inventors diligently made investigations in view of the problem described above. As a result, the inventors have discovered that an iridium complex compound which includes a phenyl(iso)quinoline or phenylquinazoline ligand and a phenylazole ligand emits red light with a satisfactory luminescent quantum yield and that an organic electroluminescent element employing the iridium complex compound has an improved luminescent efficiency. The present invention has been thus achieved.

Essential points of the invention are as follows.

<1> An iridium complex compound represented by the following formula (1):

$$\text{Ir}(L^1)_m(L^2)_n(L^3)_{3-m-n} \quad (1)$$

[In formula (1), Ir represents an iridium atom; $L^1$ to $L^3$ each independently represent an organic ligand bonded to the Ir, and the $L^1$ is selected from the group consisting of ligands represented by any of the following formula (2-1) to formula (2-3) and the $L^2$ is a ligand represented by the following formula (3-1); m and n each are an integer of 1 or 2, and m+n is 3 or less; the $L^3$ is not a ligand represented by any of formulae (2-1) to (2-3) or by formula (3-1); and in the case where there are a plurality of moieties represented by any of $L^1$ to $L^3$, these moieties may be the same or different.],

[Chem. 1]

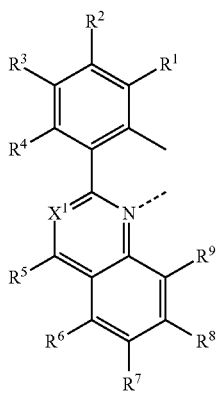
(2-1)

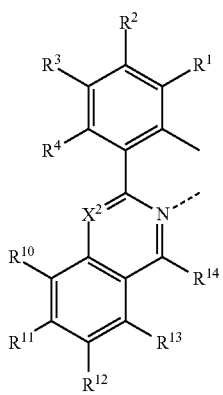
(2-2)

[Chem.2]

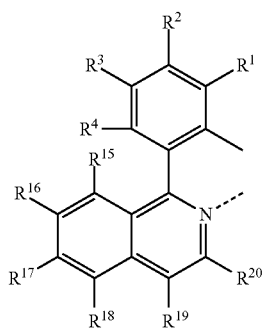
(2-3)

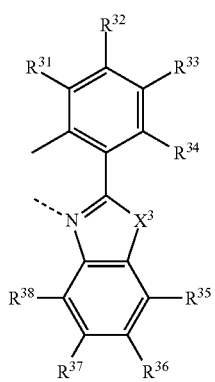
(3-1)

[In the formulae, $X^1$ and $X^2$ each independently represent a nitrogen atom or C—$R^{21}$; and $R^1$ to $R^{21}$ and $R^{31}$ to $R^{38}$ each independently represent a hydrogen atom, an alkyl group having 1-20 carbon atoms, a (hetero)aralkyl group having 7-40 carbon atoms, an alkoxy group having 1-20 carbon atoms, a (hetero)aryloxy group having 3-20 carbon atoms, an alkylsilyl group in which each alkyl group has 1-20 carbon atoms, a (hetero)arylsilyl group in which each aryl group has 6-20 carbon atoms, an alkylcarbonyl group having 2-20 carbon atoms, an arylcarbonyl group having 7-20 carbon atoms, an alkylamino group having 1-20 carbon atoms, a (hetero)arylamino group having 6-20 carbon atoms, or a (hetero)aryl group having 3-30 carbon atoms, and these groups may further have substituents, $R^1$ to $R^4$ and $R^{31}$ to $R^{34}$ each may be bonded to any adjacent one of the $R^1$ to $R^4$ or of the $R^{31}$ to $R^{34}$ to form a ring, and the ring may further have one or more substituents, $X^3$ represents an oxygen atom, a sulfur atom, or N—$R^{39}$, and $R^{39}$ represents an alkyl group having 1-20 carbon atoms, a (hetero)aralkyl group having 7-40 carbon atoms, or a (hetero)aryl group having 3-20 carbon atoms.].

<2> The iridium complex compound according to the <1> above, wherein n in the formula (1) is 2.

<3> The iridium complex compound according to the <1> or <2> above, wherein $X^3$ in the formula (3-1) is a sulfur atom.

<4> The iridium complex compound according to any one of the <1> to <3> above, wherein $X^1$ and $X^2$ in the formula (2-1) and the formula (2-2) are each a nitrogen atom.

<5> The iridium complex compound according to any one of the <1> to <4> above, wherein at least one of $L^1$ to $L^3$ in the formula (1) includes at least one partial structure represented by the following formula (4):

$$—Ar^1—Z \qquad (4)$$

[In the formula, $Ar^1$ represents an arylene group having 6-20 carbon atoms, and Z represents an alkyl group having 5-20 carbon atoms, a (hetero)aralkyl group having 7-40 carbon atoms, an alkoxy group having 4-20 carbon atoms, a (hetero)aryloxy group having 3-20 carbon atoms, or a substituent represented by the following formula (4-1).],

[Chem. 3]

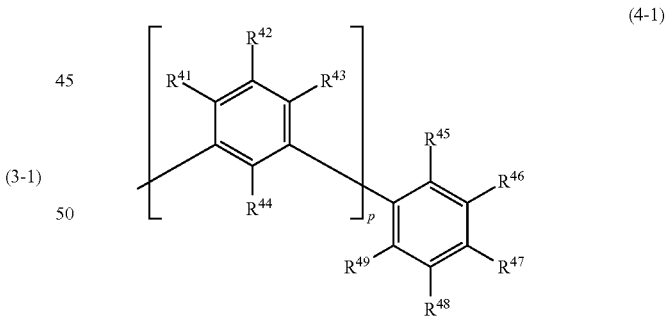
(4-1)

[In the formula, $R^{41}$ to $R^{44}$ each independently represent a hydrogen atom, a fluorine atom, a chlorine atom, a bromine atom, an alkyl group having 1-20 carbon atoms, a (hetero)aralkyl group having 7-40 carbon atoms, an alkoxy group having 1-20 carbon atoms, a (hetero)aryloxy group having 3-20 carbon atoms, or a (hetero)aryl group having 3-20 carbon atoms; $R^{45}$ to $R^{49}$ each independently represent a hydrogen atom, a fluorine atom, a chlorine atom, a bromine atom, an alkyl group having 1-20 carbon atoms, a (hetero)aralkyl group having 7-40 carbon atoms, an alkoxy group having 1-20 carbon atoms, or a (hetero)aryloxy group having 3-20 carbon atoms; and p represents an integer of 1 to 4, and when p is 2 or larger, the multiple $R^{41}$ moieties to $R^{44}$ moieties each may be the same or different.].

<6> The iridium complex compound according to the <5> above, wherein $L^2$, which is represented by the formula (3-1), includes the partial structure represented by the formula (4-1).

<7> The iridium complex compound according to any one of the <1> to <6> above, wherein $R^1$ to $R^{21}$ and $R^{31}$ to $R^{38}$ in the formulae (2-1) to (2-3) and the formula (3-1) each independently are a hydrogen atom, an alkyl group having 1-4 carbon atoms, an aryl group having 6-18 carbon atoms (the aryl group being not an aralkyl-substituted phenyl group), a phenyl group substituted with one or more aralkyl groups having 7-16 carbon atoms, or an arylamino group having 6-15 carbon atoms, or are bonded to any adjacent one of the $R^1$ to $R^{21}$ or of the $R^{31}$ to $R^{34}$ to form an aromatic heterocyclic group.

<8> The iridium complex compound according to any one of the <1> to <7> above, wherein at least two of $R^1$ to $R^9$ in the formula (2-1), at least two of $R^1$ to $R^4$ and $R^{10}$ to $R^{14}$ in the formula (2-2), and at least two of $R^1$ to $R^4$ and $R^{16}$ to $R^{20}$ in the formula (2-3) are a group other that a hydrogen atom, ant at least one of $R^{31}$ to $R^{38}$ in the formula (3-1) is a group other than a hydrogen atom.

<9> The iridium complex compound according to the <8> above, wherein at least one of the groups other than a hydrogen atom is a phenyl group substituted with one or more aralkyl groups having 7-16 carbon atoms.

<10> The iridium complex compound according to any one of the <5> to <9> above, wherein $R^3$ in the formulae (2-1) to (2-3) or $R^{33}$ in the formula (3-1) includes the substituent represented by the formula (4).

<11> A process for producing the iridium complex compound according to any one of the <1> to <10> above, comprising:

[1] reacting an iridium complex compound represented by the following formula (5) with a compound corresponding to a ligand represented by the formula (3-1) or

[2] reacting an iridium complex compound represented by the following formula (6) with a compound corresponding to a ligand represented by any of the formulae (2-1) to (2-3), in the presence of a sliver salt:

[Chem. 4]

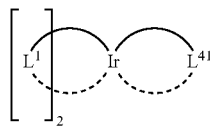

(5)

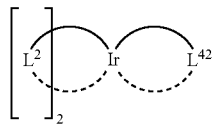

(6)

[In the formulae, $L^1$ and $L^2$ respectively represent the same ligands as the $L^1$ and $L^2$ in the formula (1), and $L^{41}$ and $L^{42}$ represent an organic ligand, with the proviso that $L^{41}$ is not a ligand represented by the formula (3-1) and $L^{42}$ is not a ligand represented by any of the formulae (2-1) to (2-3).]

<12> The process for production according to the <11> above, wherein $L^{41}$ and $L^{42}$ in the formula (5) and the formula (6) are represented by the following formula (7-1) or formula (7-2).

[Chem. 5]

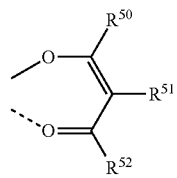

(7-1)

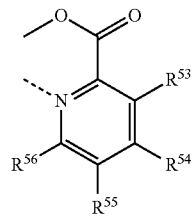

(7-2)

[In the formulae, $R^{50}$ to $R^{56}$ each independently represent a hydrogen atom, an alkyl group which has 1-20 carbon atoms and may have been substituted with one or more fluorine atoms, a phenyl group which may have been substituted with one or more alkyl groups having 1-20 carbon atoms, or a halogen atom.]

<13> A composition which comprises the iridium complex compound according to any one of the <1> to <10> above and a solvent.

<14> An organic electroluminescent element which comprises an anode, a cathode, and one or more organic layers disposed between the anode and the cathode, wherein at least one of the organic layers comprises the iridium complex compound according to any one of the <1> to <10> above.

<15> A display device which employs the organic electroluminescent element according to the <14> above.

<16> An illuminator which employs the organic electroluminescent element according to the <14> above.

Effects of the Invention

The iridium complex compound of the invention emits red light with a satisfactory quantum yield, and the organic electroluminescent element, which is produced using the iridium complex compound, has a high luminescent efficiency and is useful. This organic electroluminescent element is useful as display devices and illuminators.

BRIEF DESCRIPTION OF THE DRAWING

The FIGURE is a cross-sectional view which schematically shows an example of the structure of an organic electroluminescent element of the invention.

MODES FOR CARRYING OUT THE INVENTION

Modes for carrying out the invention are explained below in detail. However, the invention should not be construed as being limited to the following modes, and the invention can be variously modified within the spirit of the invention.

<Iridium Complex Compound>

The iridium complex compound of the invention is characterized by being represented by the following formula (1).

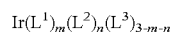

(1)

In formula (1), Ir represents an iridium atom. $L^1$ to $L^3$ each independently represent an organic ligand bonded to the Ir, and m and n each are an integer of 1 or 2, m+n being 3 or less. However, $L^1$ is a ligand participating in red luminescence, and is selected from the group consisting of ligands represented by any of formulae (2-1) to (2-3), which will be described later, and $L^2$ is an electron-withdrawing ligand contributing to an improvement in quantum yield and represents a ligand represented by formula (3-1), which will be described later. It is preferable that $L^1$ should be represented by formula (2-1) or formula (2-2), from the standpoint of durability. It is preferable that $L^2$ should be represented by formula (3-1), from the standpoint of the durability of the electron-withdrawing ligand. $L^3$ is not a ligand represented by any of formulae (2-1) to (2-3) or by formula (3-1), and in the case where there are a plurality of moieties represented by any of $L^1$ to $L^3$, these moieties may be the same or different.

It is preferable that m+n should be 3, from the standpoints of synthesis yield and durability. It is preferable that n should be 2.

Ligands $L^1$ and $L^2$ are described below in detail. Although ligand $L^1$, which is represented by any of formula (2-1) to formula (2-3), and ligand $L^2$, which is represented by formula (3-1), differ in function in the iridium complex as stated above, these ligands can have common substituents. $L^1$ and $L^2$ are hence explained together below for convenience.

[Chem. 6]

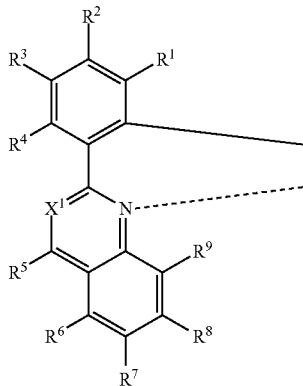

(2-1)

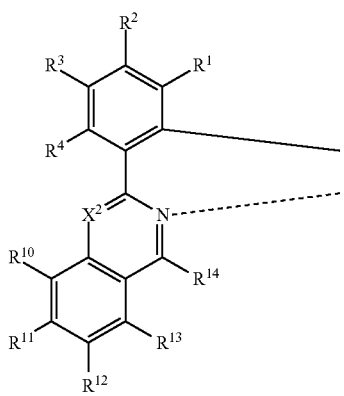

(2-2)

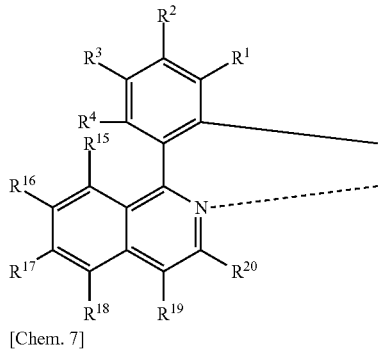

(2-3)

[Chem. 7]

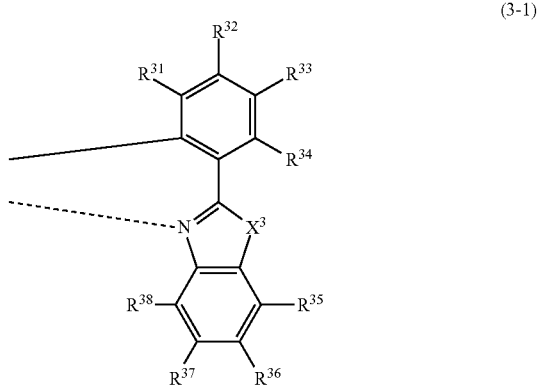

(3-1)

[In the formulae, $X^1$ and $X^2$ each independently represent a nitrogen atom or C—$R^{21}$. $R^1$ to $R^{21}$ and $R^{31}$ to $R^{38}$ each independently represent a hydrogen atom, an alkyl group having 1-20 carbon atoms, a (hetero)aralkyl group having 7-40 carbon atoms, an alkoxy group having 1-20 carbon atoms, a (hetero)aryloxy group having 3-20 carbon atoms, an alkylsilyl group in which each alkyl group has 1-20 carbon atoms, an arylsilyl group in which each aryl group has 6-20 carbon atoms, an alkylcarbonyl group having 2-20 carbon atoms, an arylcarbonyl group having 7-20 carbon atoms, an alkylamino group having 1-20 carbon atoms, an arylamino group having 6-20 carbon atoms, or a (hetero)aryl group having 3-30 carbon atoms. These groups may further have substituents.

$R^1$ to $R^4$ and $R^{31}$ to $R^{34}$ each may be bonded to any adjacent one of the $R^1$ to $R^4$ or of the $R^{31}$ to $R^{34}$ to form a ring, and the ring may further have one or more substituents.

$X^3$ represents an oxygen atom, a sulfur atom, or N—$R^{39}$, and $R^{39}$ represents an alkyl group having 1-20 carbon atoms, a (hetero)aralkyl group having 7-40 carbon atoms, or a (hetero)aryl group having 3-20 carbon atoms.]

<With Respect to Formula (2-1) to Formula (2-3)>

In formula (2-1) to formula (2-3), $X^1$ and $X^2$ each are the atom or group shown above. However, from the standpoint of durability, it is more preferable that $X^1$ and $X^2$ should be both nitrogen atoms. $R^1$ to $R^{21}$ each independently represent any of the atom and groups shown above. One of the features of the iridium complex of the invention resides in that the ligand $L^1$, which is represented by any of formula (2-1) to formula (2-3), has a phenyl(iso)quinoline framework or a phenylquinazoline framework, and differences in the kinds of the moieties represented by $R^1$ to $R^{21}$ of the framework exert little influence on the effect.

From the standpoint of durability, $X^1$ and $X^2$ each more preferably are a hydrogen atom, an alkyl group having 1-20 carbon atoms, a (hetero)aralkyl group having 7-40 carbon atoms, an arylamino group having 6-20 carbon atoms, or a (hetero)aryl group having 3-20 carbon atoms, among the atom and groups shown above, and even more preferably are a hydrogen atom, an alkyl group having 1-20 carbon atoms, a (hetero)aralkyl group having 7-40 carbon atoms, or a (hetero)aryl group having 3-20 carbon atoms. These groups, which exclude hydrogen atom, may have been further substituted.

In this description, the terms (hetero)aryl group, (hetero)aralkyl group, and (hetero)aryloxy group respectively mean an aryl group which may contain one or more heteroatoms, an aralkyl group which may contain one or more heteroatoms, and an aryloxy group which may contain one or more heteroatoms. The expression "may contain one or more heteroatoms" means the state in which one or more of the carbon atoms constituting the main framework of the aryl group, aralkyl group, or aryloxy group have been replaced with one or more heteroatoms, and examples of the heteroatoms include nitrogen, oxygen, sulfur, phosphorus, and silicon atoms. Of these, nitrogen atom is preferred from the standpoint of durability. From the standpoint of durability, it is preferable that the (hetero)aryl group, (hetero)aralkyl group, and (hetero)aryloxy group each should be one in which no carbon atom has been replaced with a heteroatom. Namely, it is preferable that these groups should be an aryl group, an aralkyl group, and an aryloxy group.

The alkyl group having 1-20 carbon atoms may be any of linear, branched, and cyclic alkyl groups. Specific examples thereof include methyl, ethyl, n-propyl, n-butyl, n-pentyl, n-hexyl, n-octyl, isopropyl, isobutyl, isopentyl, t-butyl, and cyclohexyl. Preferred of these are linear alkyl groups having 1-6 carbon atoms, such as methyl, ethyl, n-butyl, and n-hexyl.

With respect to examples of the (hetero)aralkyl group having 7-40 carbon atoms, the term "(hetero)aralkyl group" means a linear, branched, or cyclic alkyl group in which the hydrogen atoms as components of the group have been partly replaced with one or more (hetero)aryl groups. Specific examples thereof include 1-phenyl-1-ethyl, cumyl, 5-phenyl-1-pentyl, 6-phenyl-1-hexyl, 7-phenyl-1-heptyl, and tetrahydronaphthyl. Preferred of these are aralkyl groups having 8-20 carbon atoms, such as 5-phenyl-1-pentyl, 6-phenyl-1-hexyl, and 7-phenyl-1-heptyl. In particular, aralkyl groups having 10-15 carbon atoms are preferred from the standpoint of high durability.

Examples of the alkoxy group having 1-20 carbon atoms include methoxy, ethoxy, propyloxy, isopropyloxy, hexyloxy, cyclohexyloxy, and octadecyloxy. Preferred of these is hexyloxy.

Examples of the (hetero)aryloxy group having 3-20 carbon atoms include phenoxy and 4-methylphenyloxy. Preferred of these is phenoxy.

Examples of the alkylsilyl group having 1-20 carbon atoms include trimethylsilyl, triethylsilyl, triisopropylsilyl, t-butyldimethylsilyl, and t-butyldiphenylsilyl. Preferred of these are triisopropylsilyl, t-butyldimethylsilyl, and t-butyldiphenylsilyl.

Examples of the (hetero)arylsilyl group having 3-20 carbon atoms include diphenylpyridylsilyl and triphenylsilyl. Preferred of these is triphenylsilyl.

Examples of the alkylcarbonyl group having 2-20 carbon atoms include acetyl, propionyl, pivaloyl, caproyl, decanoyl, and cyclohexylcarbonyl. Preferred of these are acetyl and pivaloyl.

Examples of the (hetero)arylcarbonyl group having 4-20 carbon atoms include benzoyl, naphthoyl, and anthrayl. Preferred of these is benzoyl.

Examples of the alkylamino group having 1-20 carbon atoms include methylamino, dimethylamino, diethylamino, ethylmethylamino, dihexylamino, dioctylamino, and dicyclohexylamino. Preferred of these are dimethylamino and dicyclohexylamino.

Examples of the (hetero)arylamino group having 3-20 carbon atoms include (4-pyridylphenyl)phenylamino, phenylamino, diphenylamino, di(4-tolyl)amino, and di(2,6-dimethylphenyl)amino. Preferred of these are arylamino groups having 6-16 carbon atoms, such as diphenylamino and di(4-tolyl)amino.

The term "(hetero)aryl group having 3-30 carbon atoms" means both an aromatic hydrocarbon group having a free valence of 1 and an aromatic heterocyclic group having a free valence of 1.

Examples thereof include the following groups each having a free valence of 1: a benzene ring, naphthalene ring, anthracene ring, phenanthrene ring, perylene ring, tetracene ring, pyrene ring, benzpyrene ring, chrysene ring, triphenylene ring, fluoranthene ring, furan ring, benzofuran ring, dibenzofuran ring, thiophene ring, benzothiophene ring, dibenzothiophene ring, pyrrole ring, pyrazole ring, imidazole ring, oxadiazole ring, indole ring, carbazole ring, pyrroloimidazole ring, pyrrolopyrazole ring, pyrrolopyrrole ring, thienopyrrole ring, thienothiophene ring, furopyrrole ring, furofuran ring, thienofuran ring, benzisooxazole ring, benzisothiazole ring, benzimidazole ring, pyridine ring, pyrazine ring, pyridazine ring, pyrimidine ring, triazine ring, quinoline ring, isoquinoline ring, cinnoline ring, quinoxaline ring, benzimidazole ring, perimidine ring, quinazoline ring, quinazolinone ring, and azulene ring.

Preferred of such (hetero)aryl groups, from the standpoints of quantum yield and durability, are a benzene ring, naphthalene ring, dibenzofuran ring, dibenzothiophene ring, carbazole ring, pyridine ring, pyrimidine ring, and triazine ring which each have a free valence of 1. More preferred of these is either an aryl group which has 6-18 carbon atoms (more preferably 6-14 carbon atoms), such as a benzene ring, naphthalene ring, or phenanthrene ring, and which has a free valence of 1 and may have been substituted with one or more alkyl groups having 1-8 carbon atoms or a pyridine ring which has a free valence of 1 and which may have been substituted with one or more alkyl groups having 1-4 carbon atoms. It is more preferable that the (hetero)aryl group should be an aryl group which has 6-18 carbon atoms (more preferably 6-14 carbon atoms), such as a benzene ring, naphthalene ring, or phenanthrene ring, and which has a free valence of 1 and may have been substituted with one or more alkyl groups having 1-8 carbon atoms.

In the present invention, the term "free valence" means a linking site capable of forming a bond with another free valence, as described in Yūki-kagaku/Sei-kagaku Meimei-hō (jō) (revised version, 2nd edition, Nankodo Co., Ltd., published in 1992). For example, the term "benzene ring having a free valence of 1" means a phenyl group, and the term "benzene ring having a free valence of 2" means a phenylene group.

$R^1$ to $R^{21}$ may further have substituents. Specifically, $R^1$ to $R^{21}$ each may have been substituted with at least one substituent selected from the group consisting of a fluorine atom, a chlorine atom, a bromine atom, and the substituents enumerated above as the substituents represented by $R^1$ to $R^{21}$. Examples of these substituents are the same as those shown hereinabove.

$R^1$ to $R^4$ each may be bonded to any adjacent one of the $R^1$ to $R^4$ to form a ring. The ring thus formed may be either a hydrocarbon ring or a heterocyclic ring.

Examples of such rings include a fluorene ring, naphthalene ring, phenanthrene ring, triphenylene ring, chrysene ring, benzofuran ring, dibenzofuran ring, benzothiophene ring, dibenzothiophene ring, carbazole ring, carboline ring, tetrahydronaphthalene ring, quinoline ring, quinazoline ring, azaphenanthrene ring, and azatriphenylene ring. Preferred of these are a fluorene ring, naphthalene ring, carbazole ring, and carboline ring. More preferred are a fluorene ring, naphthalene ring, and carbazole ring.

These rings each may be further substituted with at least one substituent selected from the group consisting of the substituents shown above as examples of the substituents which may be further possessed by $R^1$ to $R^{21}$. Examples of these substituents are the same as those shown hereinabove.

From the standpoint of durability, it is more preferable that $R^1$ to $R^{21}$ should each independently be a hydrogen atom, an alkyl group having 1-4 carbon atoms, an aralkyl group having 10-15 carbon atoms, an arylamino group having 6-16 carbon atoms, an aryl group having 6-18 carbon atoms (excluding aralkyl-substituted phenyl), or a phenyl group substituted with one or more aralkyl groups having 7-16 carbon atoms, among the atom and groups shown above, or be bonded to any adjacent one of the $R^1$ to $R^{21}$ to form an aromatic heterocyclic group. It is especially preferable that $R^1$ to $R^{21}$ should each independently be a hydrogen atom, an alkyl group having 1-4 carbon atoms, an aryl group having 6-18 carbon atoms (excluding aralkyl-substituted phenyl), a phenyl group substituted with one or more aralkyl groups having 7-16 carbon atoms, or an arylamino group having 6-15 carbon atoms or be bonded to any adjacent one of $R^1$ to $R^{21}$ to form an aromatic heterocyclic group.

From the standpoints of solubility and durability, it is preferable that at least two, preferably at least three, of substituents $R^1$ to $R^9$ in formula (2-1), at least two, preferably at least three, of substituents $R^1$ to $R^4$ and $R^{10}$ to $R^{14}$ in formula (2-2), and at least two, preferably at least three, of substituents $R^1$ to $R^4$ and $R^{16}$ to $R^{20}$ in formula (2-3) should not be hydrogen atoms. From the standpoint of attaining both solubility and durability, it is preferable that at least one of these substituents should be a phenyl group substituted with one or more aralkyl groups having 7-16 carbon atoms. For the same reason, it is preferable that at least one of the groups other than a hydrogen atom should be a phenyl group substituted with one or more aralkyl groups having 7-16 carbon atoms.

It is more preferable, from the standpoint of quantum yield, that $L^1$ should be represented by formula (2-1) or formula (2-2), among those.

<With Respect to Formula (3-1)>

In formula (3-1), $X^3$ represents an oxygen atom, a sulfur atom, or $N-R^{39}$, and $R^{39}$ represents an alkyl group having 1-20 carbon atoms, a (hetero)aralkyl group having 7-40 carbon atoms, or a (hetero)aryl group having 3-20 carbon atoms. However, from the standpoint of obtaining a high quantum yield, it is preferable that $X^3$ should be a ligand which has a strong electron-withdrawing nature. It is therefore preferable that $X^3$ should be an oxygen atom or a sulfur atom. Meanwhile, from the standpoint of durability, a ligand having high aromaticity is preferred and, hence, it is more preferable that $X^3$ should be a sulfur atom.

$R^{31}$ to $R^{38}$ in formula (3-1) are substituents represented by the same definition as the $R^1$ to $R^{21}$ described above. One of the features of the iridium complex of the invention resides in that ligand $L^2$, which is represented by formula (3-1), has a phenylazole framework, and differences in the kinds of the moieties represented by $R^{31}$ to $R^{38}$ exert little influence on the effect.

Examples of the groups represented by $R^{31}$ to $R^{38}$ and preferred examples thereof are the same as in the case of $R^1$ to $R^{21}$. However, preferred examples of the aryl group further include biphenyl, terphenyl, and quaterphenyl. Consequently, the number of carbon atoms of the aryl group is preferably 6-30, especially preferably 6-18. In the case where any of $R^{31}$ to $R^{34}$ is bonded to any adjacent one of the $R^{31}$ to $R^{34}$ to form a ring, examples of the ring are the same as in the case of $R^1$ to $R^4$.

From the standpoint of durability, it is preferable that $R^{31}$ to $R^{38}$ should each independently be a hydrogen atom or a group selected from among an alkyl group having 1-4 carbon atoms, an aryl group having 6-18 carbon atoms (excluding aralkyl-substituted phenyl), an aralkyl group having 10-15 carbon atoms, a phenyl group substituted with one or more aralkyl groups having 7-16 carbon atoms, and an arylamino group having 6-15 carbon atoms, or be bonded to any adjacent one of the $R^{31}$ to $R^{38}$ to form an aromatic heterocyclic group. It is more preferable that $R^{31}$ to $R^{38}$ should each independently be a hydrogen atom, an alkyl group having 1-4 carbon atoms, an aryl group having 6-18 carbon atoms (excluding aralkyl-substituted phenyl), a phenyl group substituted with one or more aralkyl groups having 7-16 carbon atoms, or an arylamino group having 6-15 carbon atoms or be bonded to any adjacent one of the $R^{31}$ to $R^{38}$ to form an aromatic heterocyclic group.

Furthermore, from the standpoints of durability and solubility, it is preferable that at least one of substituents $R^{31}$ to $R^{38}$ in formula (3-1) should not be a hydrogen atom. For the same reason, it is preferable that at least one of the groups other than a hydrogen atom should be a phenyl group substituted with one or more aralkyl groups having 7-16 carbon atoms.

Ligand $L^1$, which is represented by any of formula (2-1) to formula (2-3), and ligand $L^2$, which is represented by formula (3-1), in the iridium complex compound represented by formula (1) were explained above. It is, however, preferable that the iridium complex compound represented by formula (1) should be one in which at least one of ligands $L^1$ to $L^3$ includes at least one partial structure represented by the following formula (4), from the standpoints of enabling the iridium complex compound represented by formula (1) to show improved solubility in the solvent when used for producing a composition containing the iridium complex compound and of thereby preventing the quantum yield and durability from decreasing due to aggregation. Furthermore, from the standpoint of quantum yield, it is more preferable that $L^2$, which is represented by formula (3-1), should include a partial structure represented by the following formula (4).

$$-Ar^1-Z \qquad (4)$$

[In the formula, $Ar^1$ represents an arylene group having 6-20 carbon atoms, and Z represents an alkyl group having 5-20 carbon atoms, a (hetero)aralkyl group having 7-40 carbon atoms, an alkoxy group having 4-20 carbon atoms, a (hetero) aryloxy group having 3-20 carbon atoms, or a substituent represented by formula (4-1), which will be described later.]

The arylene group represented by $Ar^1$ may be a group which constitutes the phenyl(iso)quinoline framework, phenylquinazoline framework, or phenylazole framework as the basic framework of each of formulae (2-1) to (2-3) or formula (3-1) or may be a group which constitutes a substituent of any of these frameworks.

From the standpoint of attaining both solubility and durability, it is preferable that Z should be an alkyl group having 5-20 carbon atoms, a (hetero)aralkyl group having 7-40 carbon atoms, or a substituent represented by formula (4-1), which will be described later. More preferably, Z is a (hetero)aralkyl group having 7-40 carbon atoms or a substituent represented by formula (4-1), which will be described later.

Examples of the arylene group having 6-20 carbon atoms include a benzene ring, naphthalene ring, fluorene ring, anthracene ring, phenanthrene ring, perylene ring, tetracene ring, pyrene ring, benzpyrene ring, chrysene ring, triphenylene ring, and fluoranthene ring which each have a free valence of 2. Of these, the benzene ring having a free valence of 2 is preferred from the standpoint of durability.

Examples of the alkyl group having 5-20 carbon atoms include linear, branched, or cyclic alkyl groups, and specific examples thereof include n-pentyl, n-hexyl, n-octyl, isopentyl, and cyclohexyl. Preferred of these are linear alkyl groups having 5-10 carbon atoms, such as n-pentyl, n-hexyl, and n-octyl.

With respect to examples of the (hetero)aralkyl group having 7-40 carbon atoms, the term "(hetero)aralkyl group" means a linear, branched, or cyclic alkyl group in which the hydrogen atoms as components of the group have been partly replaced with one or more (hetero)aryl group. Specific examples thereof include 1-phenyl-1-ethyl, cumyl, 5-phenyl-1-pentyl, 6-phenyl-1-hexyl, 7-phenyl-1-heptyl, and tetrahydronaphthyl. Preferred of these are aralkyl groups having 10-15 carbon atoms, such as 5-phenyl-1-pentyl, 6-phenyl-1-hexyl, and 7-phenyl-1-heptyl.

Examples of the alkoxy group having 4-20 carbon atoms include hexyloxy, cyclohexyloxy, and octadecyloxy. Preferred of these are alkoxy groups having 4-8 carbon atoms, in particular, hexyloxy.

Examples of the (hetero)aryloxy group having 3-20 carbon atoms include phenoxy and 4-methylphenyloxy. Preferred of these are aryloxy groups having 6-8 carbon atoms, in particular, phenoxy.

The substituent represented by formula (4-1) has the following structure.

[Chem. 8]

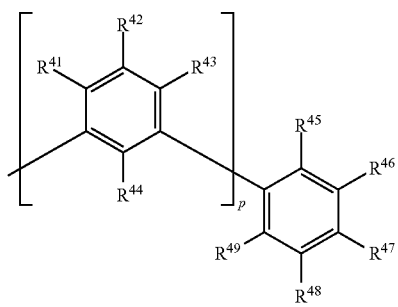

(4-1)

[In the formula, $R^{41}$ to $R^{44}$ each independently represent a hydrogen atom, a fluorine atom, a chlorine atom, a bromine atom, an alkyl group having 1-20 carbon atoms, a (hetero)aralkyl group having 7-40 carbon atoms, an alkoxy group having 1-20 carbon atoms, a (hetero)aryloxy group having 3-20 carbon atoms, or a (hetero)aryl group having 3-20 carbon atoms. $R^{45}$ to $R^{49}$ each independently represent a hydrogen atom, a fluorine atom, a chlorine atom, a bromine atom, an alkyl group having 1-20 carbon atoms, a (hetero)aralkyl group having 7-40 carbon atoms, an alkoxy group having 1-20 carbon atoms, or a (hetero)aryloxy group having 3-20 carbon atoms. Symbol p represents an integer of 1 to 4, and when p is 2 or larger, the multiple $R^{41}$ moieties to $R^{44}$ moieties each may be the same or different.]

Examples of these substituents are the same as those shown hereinabove. From the standpoint of durability, however, it is preferable that $R^{41}$ to $R^{49}$ should each be a hydrogen atom.

It is preferable that the iridium complex compound of the invention should contain at least one substituent represented by formula (4) as a partial structure, because this partial structure improves the solubility of the compound in organic solvents and brings about the effects of preventing the quantum yield from decreasing due to aggregation and of preventing an organic electroluminescent element produced by a wet-process coating-fluid application method from decreasing in durability. Furthermore, from the standpoint of preventing the iridium complex compound from changing in maximal-luminescence peak or decreasing in durability, it is more preferable that the substituent represented by formula (4) should be included in the $R^3$ within each of formulae (2-1) to (2-3) or in the $R^{33}$ within formula (3-1), and it is even more preferable that the $R^3$ and/or $R^{33}$ should be a substituent represented by formula (4).

It is even more preferable that $L^2$, which is represented by formula (3-1), should include a partial structure represented by formula (4-1).

<Methods for Synthesizing the Iridium Complex Compound>

The iridium complex compound of the invention can be synthesized from ligands which can be synthesized, for example, by a combination of known methods, and from an iridium compound.

For synthesizing the iridium complex compound of the invention, common methods for synthesizing iridium complex compounds can be applied, such as, for example, a method in which a dinuclear iridium complex is formed and a tris-ligand compound is formed thereafter, as shown by the following (scheme A), and a method in which an iridium complex intermediate is formed from a dinuclear iridium complex and an iridium complex compound of the invention is formed thereafter, as shown by the following (scheme B) or (scheme C). However, usable synthesis methods are not limited to these examples. In (scheme A) and (scheme B), $X^1$ and $X^3$ respectively have the same meanings as the $X^1$ and $X^3$ within formula (2-1) and formula (3-1) described above, R represents a hydrogen atom or any substituent. The multiple R moieties may be the same or different.

scheme A
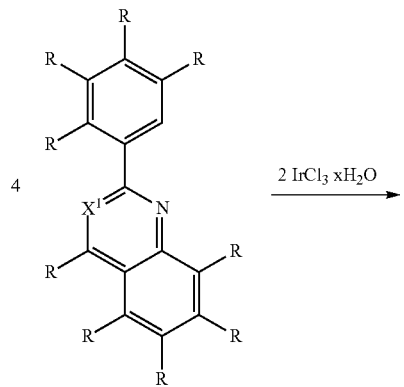
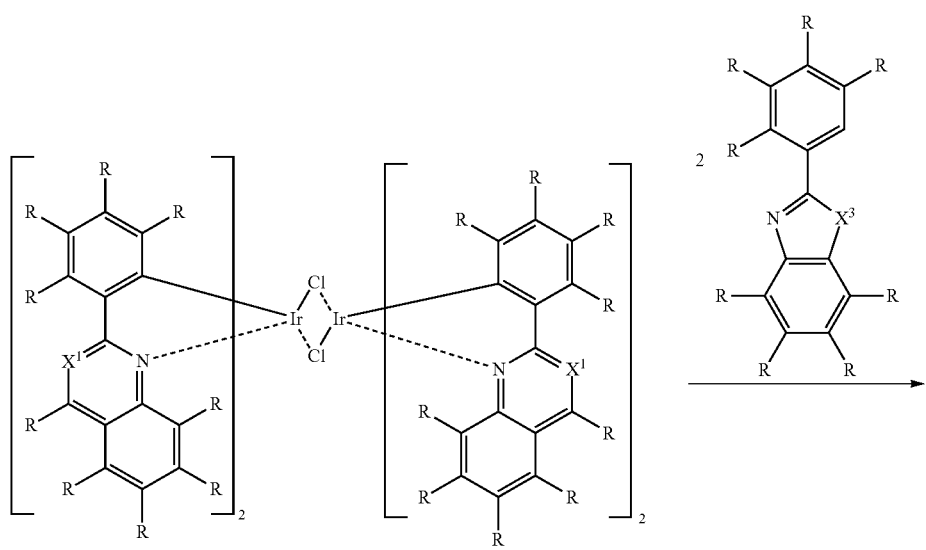
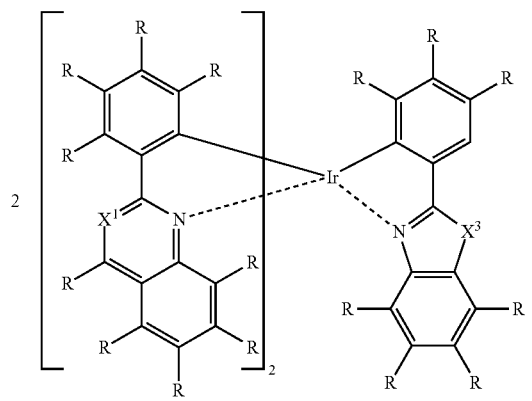

(scheme B)
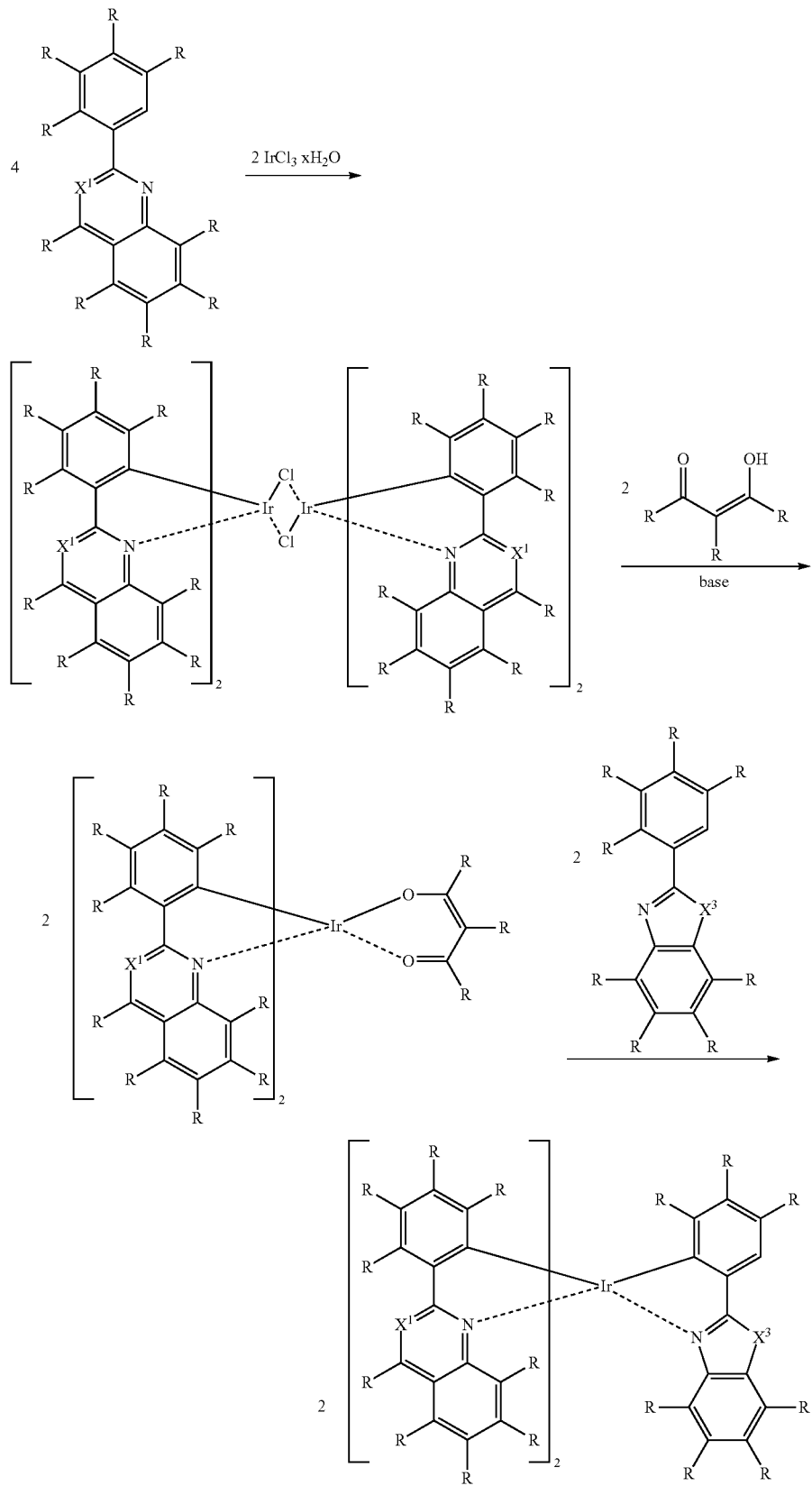

(scheme C)
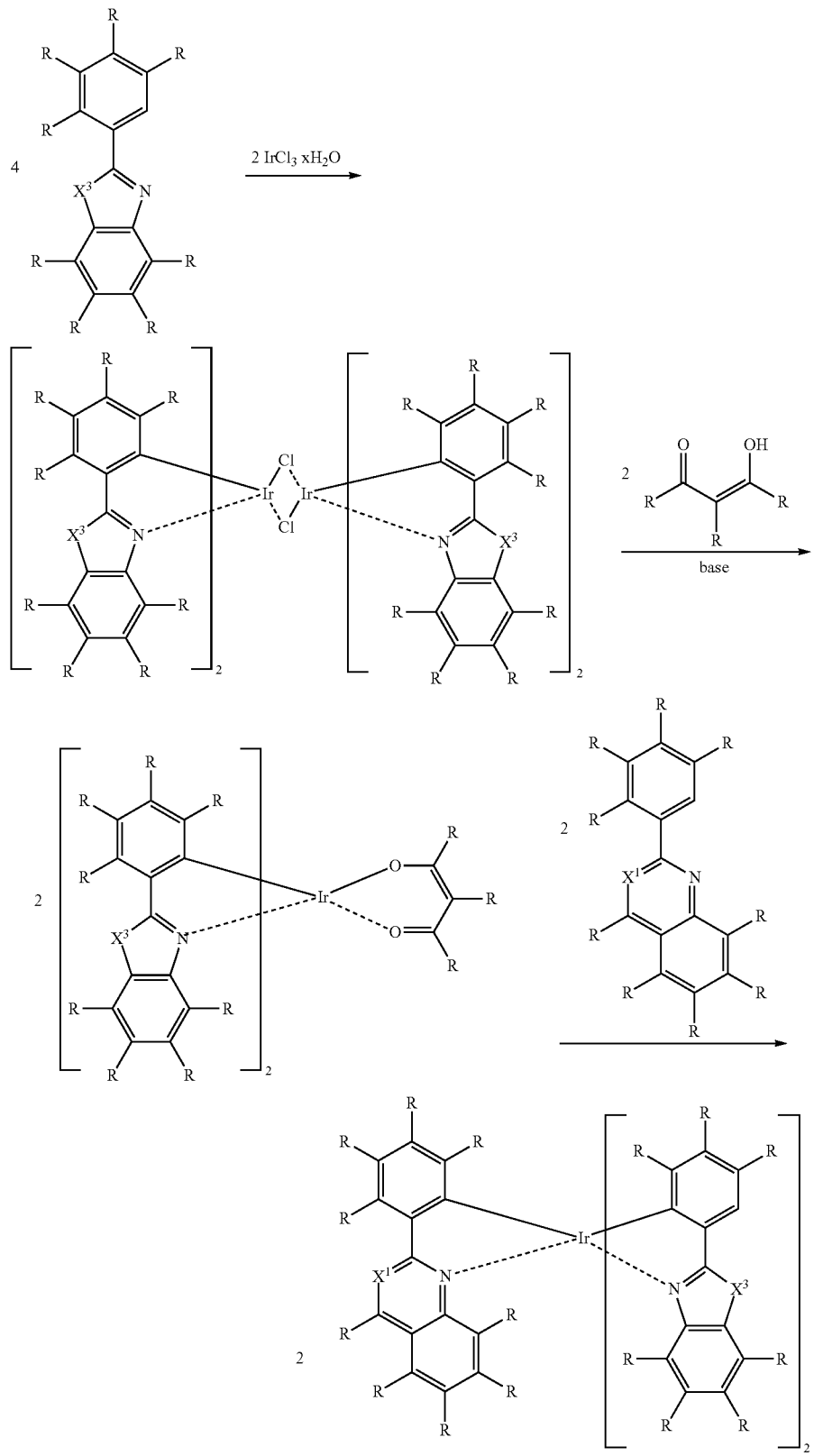

In each of the reaction schemes (scheme A), (scheme B), and (scheme C), it is possible to appropriately regulate the feed ratio in which the ligand(s) and the iridium compound are actually fed, while taking account of the efficiency of the reaction and selectivity. As the iridium compound, appropriate iridium compounds such as, for example, an Ir(acac)$_3$ complex or an Ir-cyclooctadienyl complex may be used besides the IrCl$_3$.xH$_2$O complex shown above. Meanwhile, as the iridium complex compound synthesized as an intermediate, use can be made of known auxiliary ligands, e.g., picolinate complexes, besides the ketonate complex shown above (see, for example, non-patent document 3 and *Inorganic Chemistry*, No. 40, pp. 1704-1711, 2001). A base compound such as a carbonic acid salt, a halogen-trapping agent such as a silver salt, and the like may be further used to accelerate the reactions. With respect to reaction temperature, it is preferred to use a temperature of about 50-400° C. It is more preferred to use a high temperature of 90° C. or higher. The reactions may be conducted without using a solvent, or known solvents may be used.

From the standpoint of synthesis yield, it is more preferable that the iridium complex compound of the invention should be synthesized in accordance with the method represented by the reaction scheme (scheme B) or (scheme C). Namely, it is preferred to react an iridium complex compound represented by the following formula (5) or formula (6) and any desired ligand in the presence of a silver salt such as silver trifluoromethanesulfonate, silver trifluoroacetate, silver tetrafluoroborate, silver picolinate, or bis(trifluoromethanesulfonyl)imidosilver, preferably in the presence of silver trifluoromethanesulfonate (the following reaction scheme (scheme D) or (scheme E)).

It is more preferred to react [1] an iridium complex compound represented by the following formula (5) with a compound corresponding to a ligand represented by formula (3-1) or [2] an iridium complex compound represented by the following formula (6) with a compound corresponding to a ligand represented by any of formula (2-1) to formula (2-3), in the presence of the silver salt.

[Chem. 10]

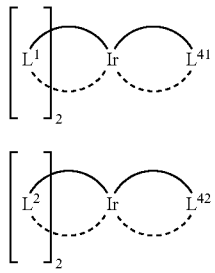

(5)

(6)

In formula (5) and formula (6), L$^1$ and L$^2$ respectively represent the same ligands as the L$^1$ and L$^2$ in formula (1), and L$^{41}$ and L$^{42}$ represent organic ligands, with the proviso that L$^{41}$ is not a ligand represented by formula (3-1) and L$^{42}$ is not a ligand represented by any of formulae (2-1) to (2-3).

As L$^{41}$ and L$^{42}$, use can be made of a known auxiliary ligand such as a diketone type ligand, e.g., acetylacetone, an aromatic heterocyclic carboxylic acid type ligand, e.g., 2-picolinic acid, pyrazole or a composite salt thereof, or a phosphorus-compound ligand, e.g., bis(diphenylphosphino) ethane (see, for example, non-patent document 3 and *Inorganic Chemistry*, No. 40, pp. 1704-1711, 2001).

scheme D

[Chem. 11]

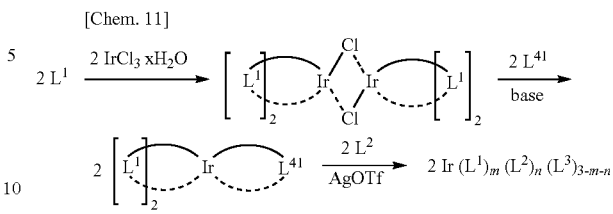

(scheme E)

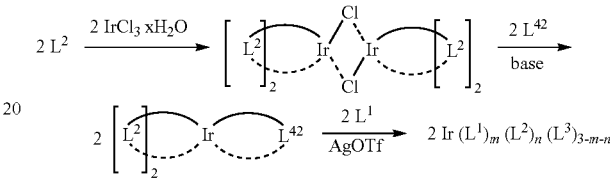

L$^1$ to L$^3$, L$^{41}$, L$^{42}$, m, and n in the reaction schemes (scheme D) and (scheme E) are the same as described above. Furthermore, Ir represents an iridium atom, and AgOTf represents silver triflate. From the standpoint of synthesis yield, it is more preferable that L$^{41}$ and L$^{42}$ should be represented by the following formula (7-1) or formula (7-2).

[Chem. 12]

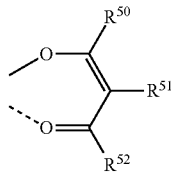

(7-1)

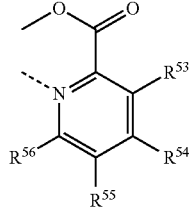

(7-2)

In formula (7-1) and formula (7-2), R$^{50}$ to R$^{56}$ each independently represent a hydrogen atom, an alkyl group which has 1-20 carbon atoms and may have been substituted with one or more fluorine atoms, a phenyl group which may have been substituted with one or more alkyl groups having 1-20 carbon atoms, or a halogen atom. Examples thereof are the same as those shown hereinabove.

<Molecular Weight>

The molecular weight of the iridium complex compound of the invention is usually 500 or higher, preferably 600 or higher, and is usually 3,000 or less, preferably 2,000 or less, from the standpoint of the high stability of the complex. However, use of a polymeric compound which contains the iridium complex compound of the invention as a side chain is also suitable.

SPECIFIC EXAMPLES

Preferred specific examples of the iridium complex compound of the invention are shown below. However, the invention should not be construed as being limited to the following examples. In this description, Me represents a methyl group, Ph represents a phenyl group, and Et represents an ethyl group.

(1) Examples of the iridium complex compound in which $L^1$ is formula (2-1), $L^2$ is formula (3-1), and m+n is 3:

[Chem. 13]

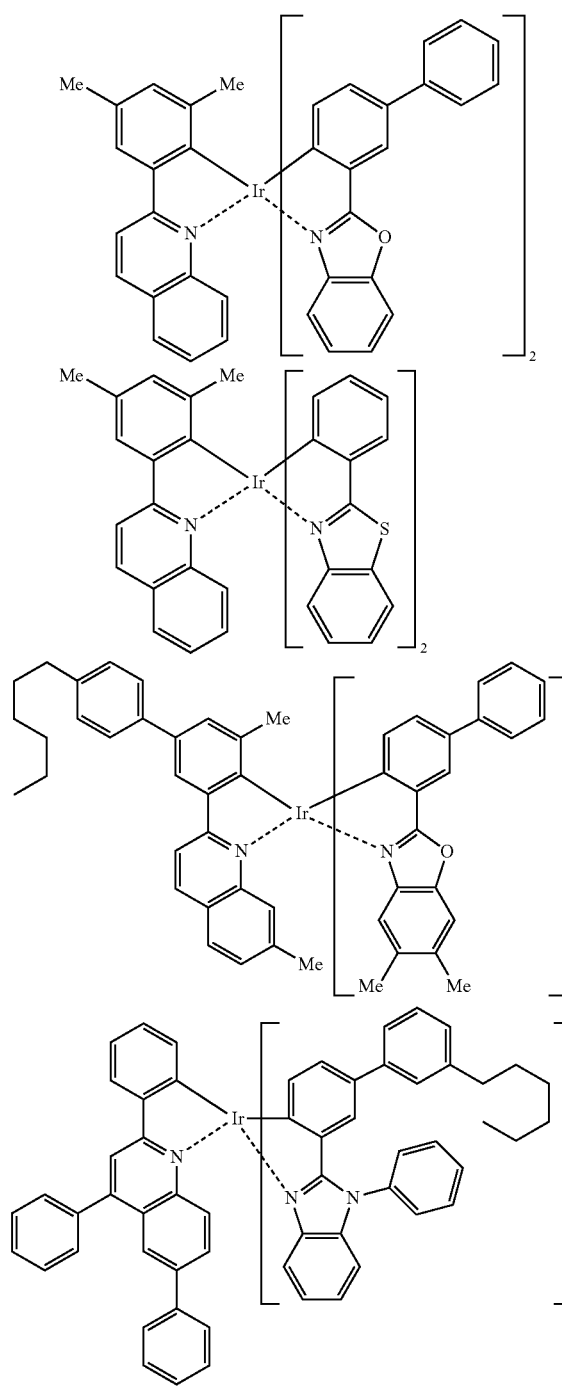
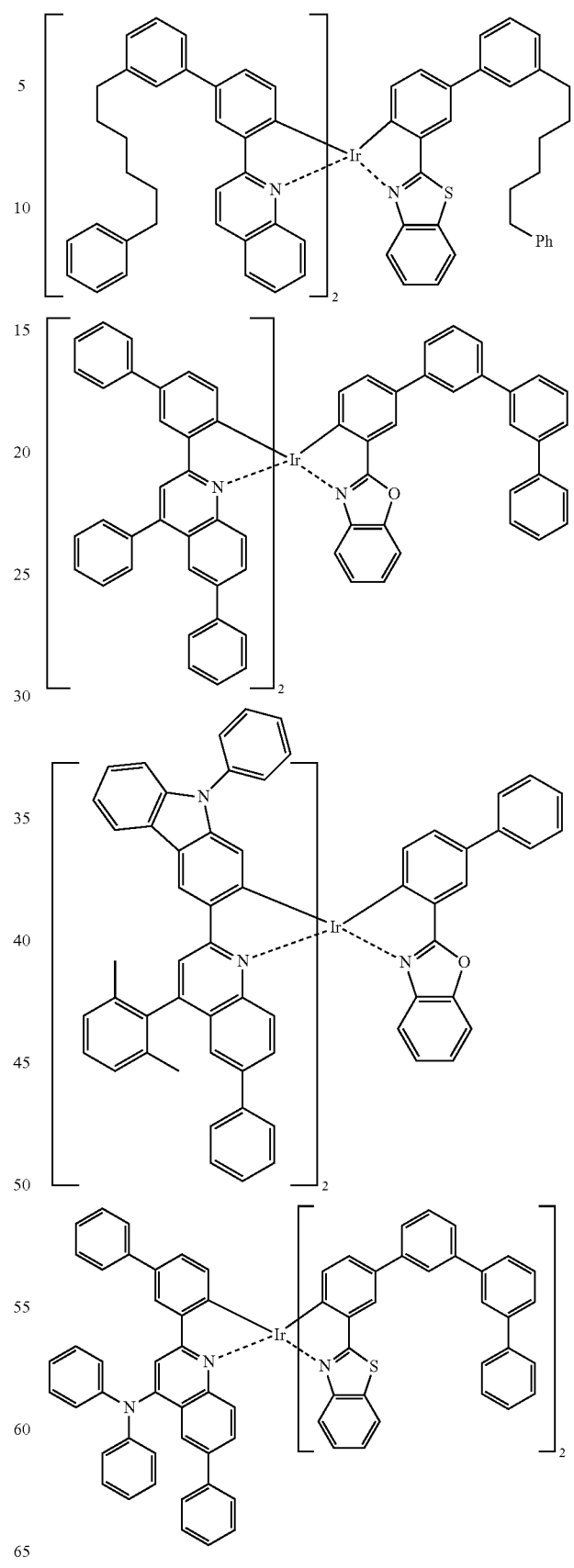

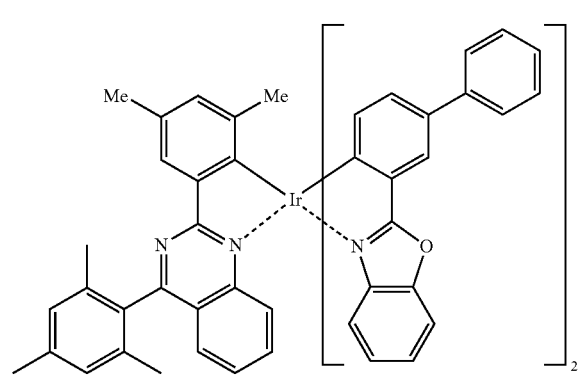
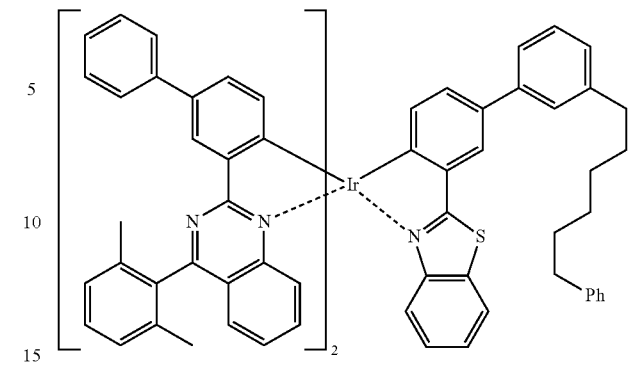
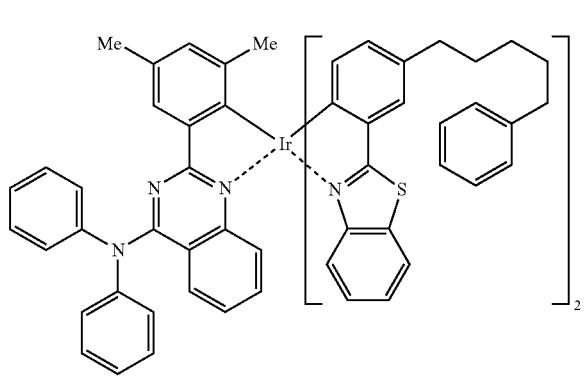
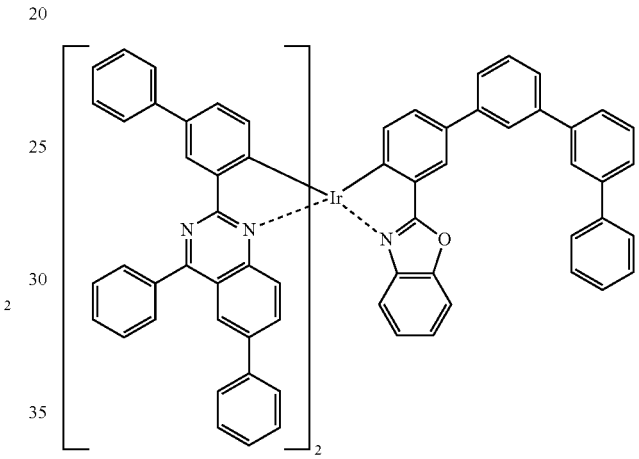
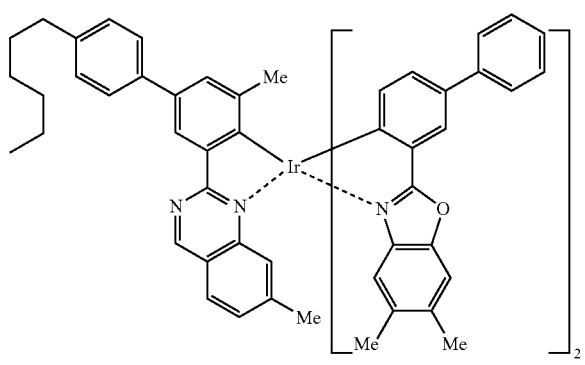
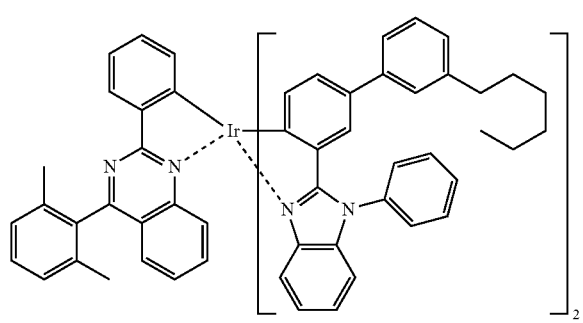

-continued
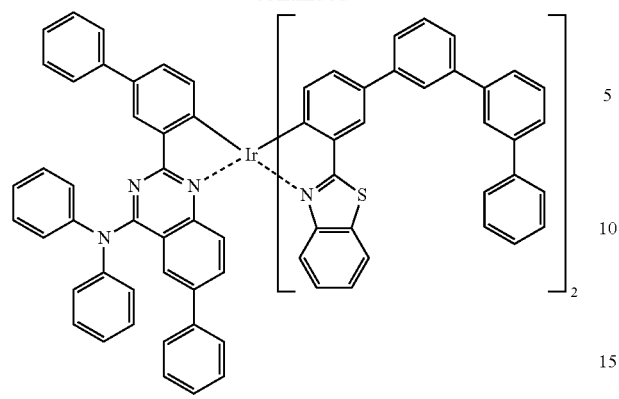
(2) Examples of the iridium complex compound in which $L^1$ is formula (2-2), $L^2$ is formula (3-1), and m+n is 3:
[Chem. 15]
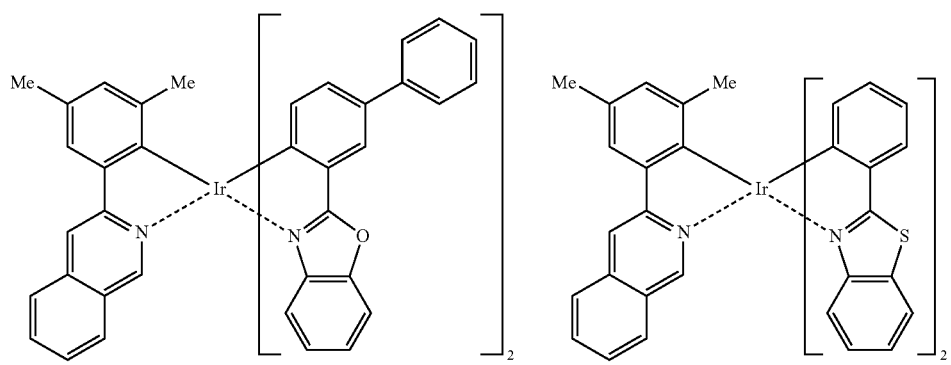
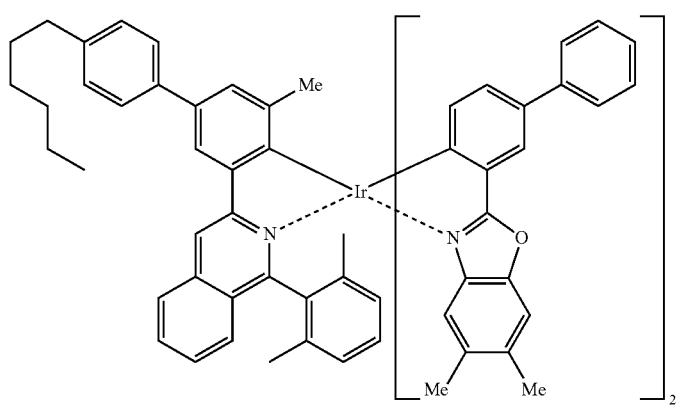

-continued
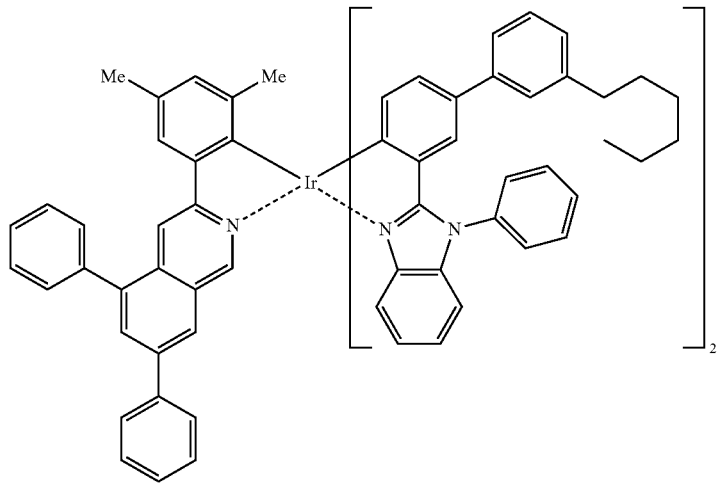
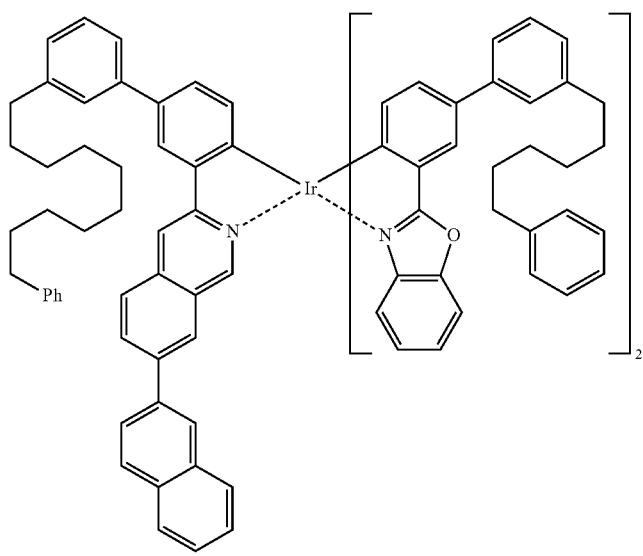
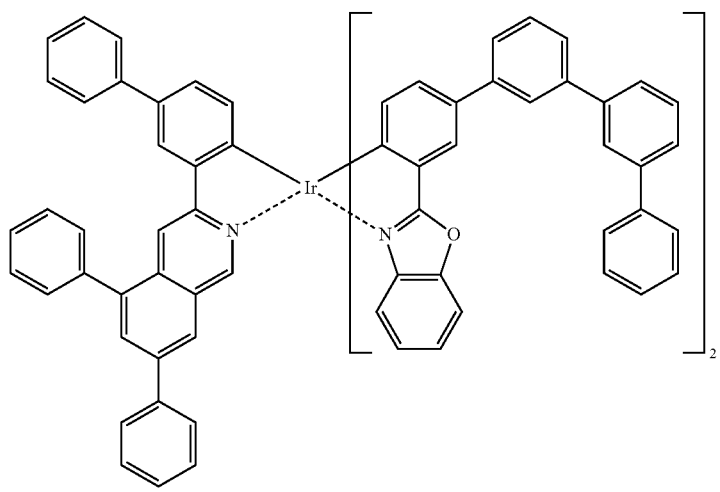

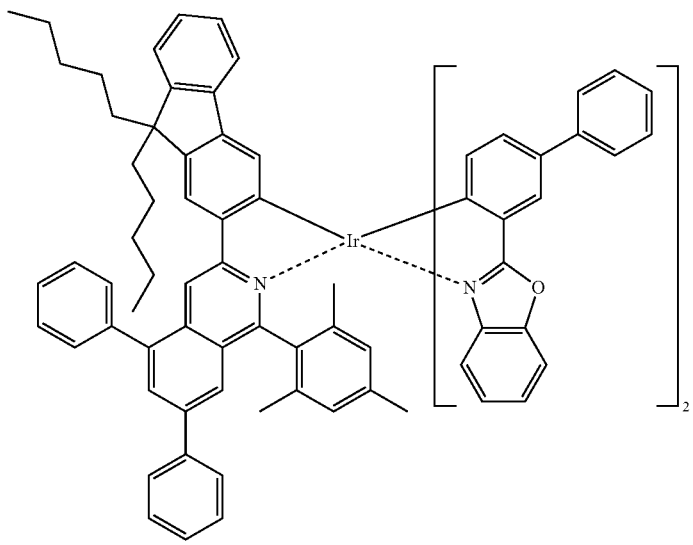
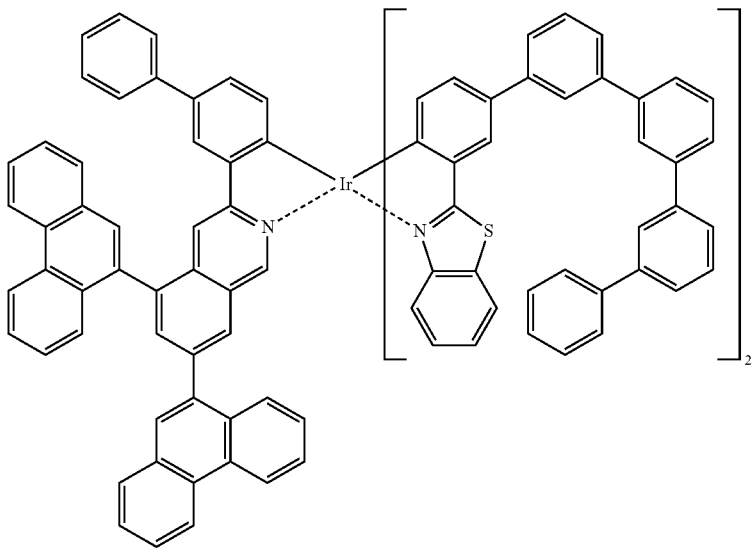
[Chem. 16]
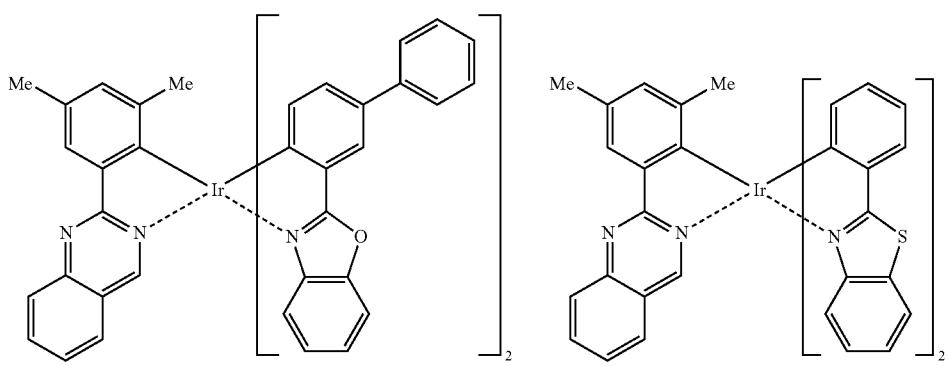

-continued
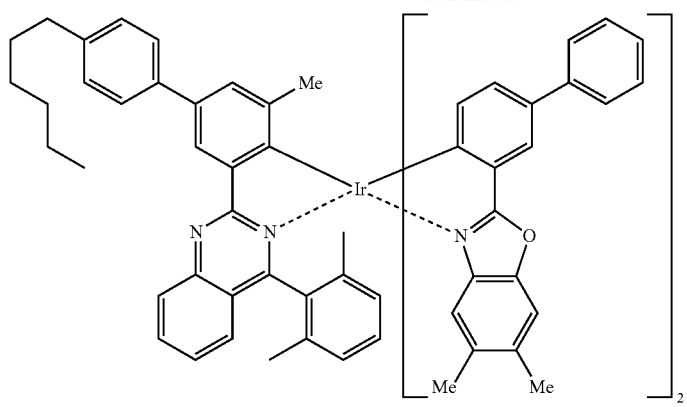
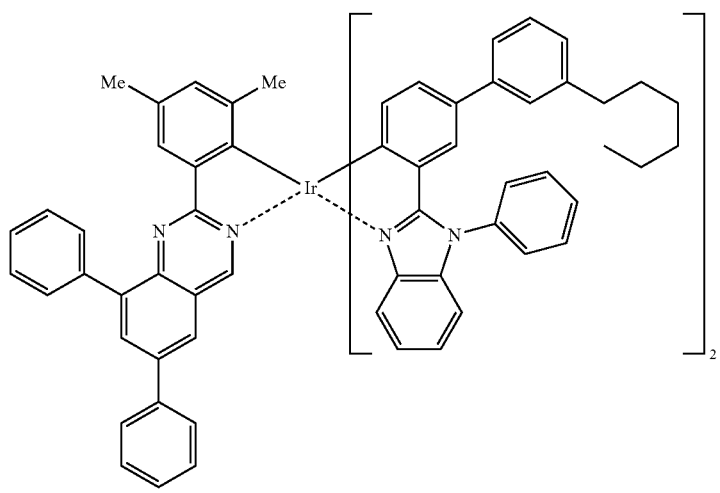
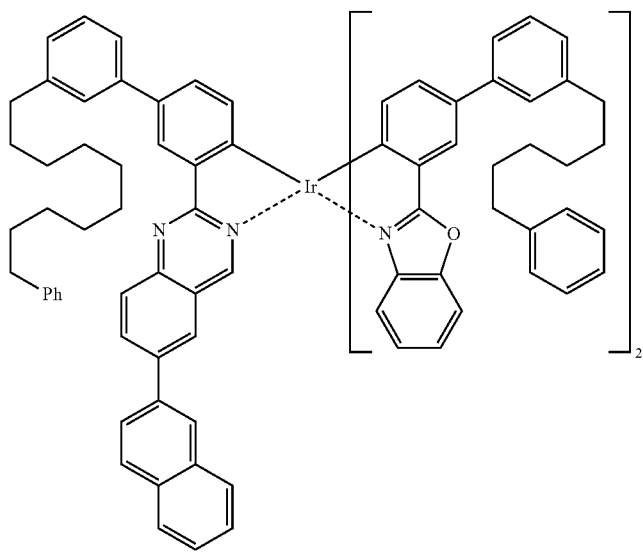

-continued
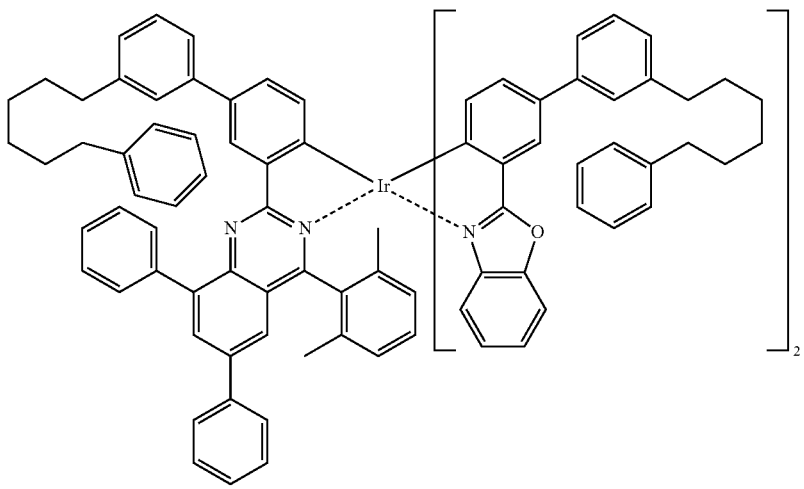
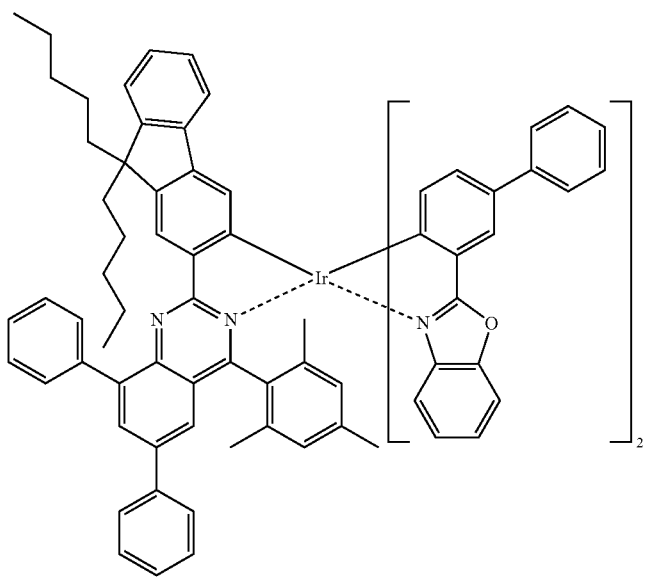
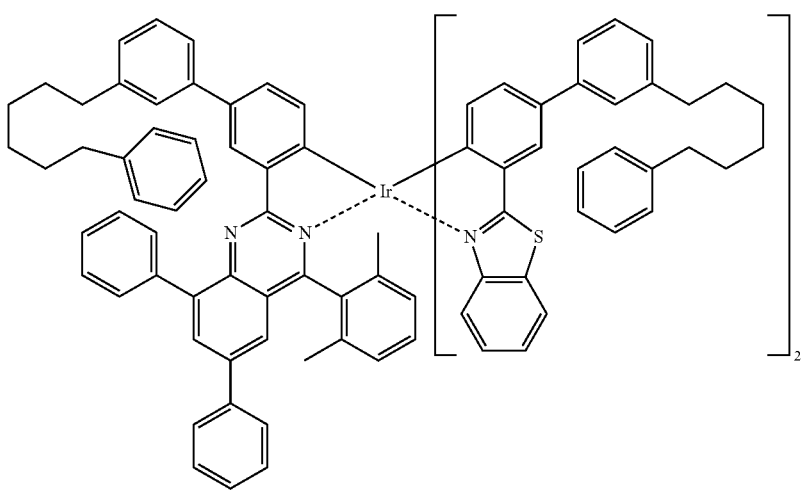

-continued
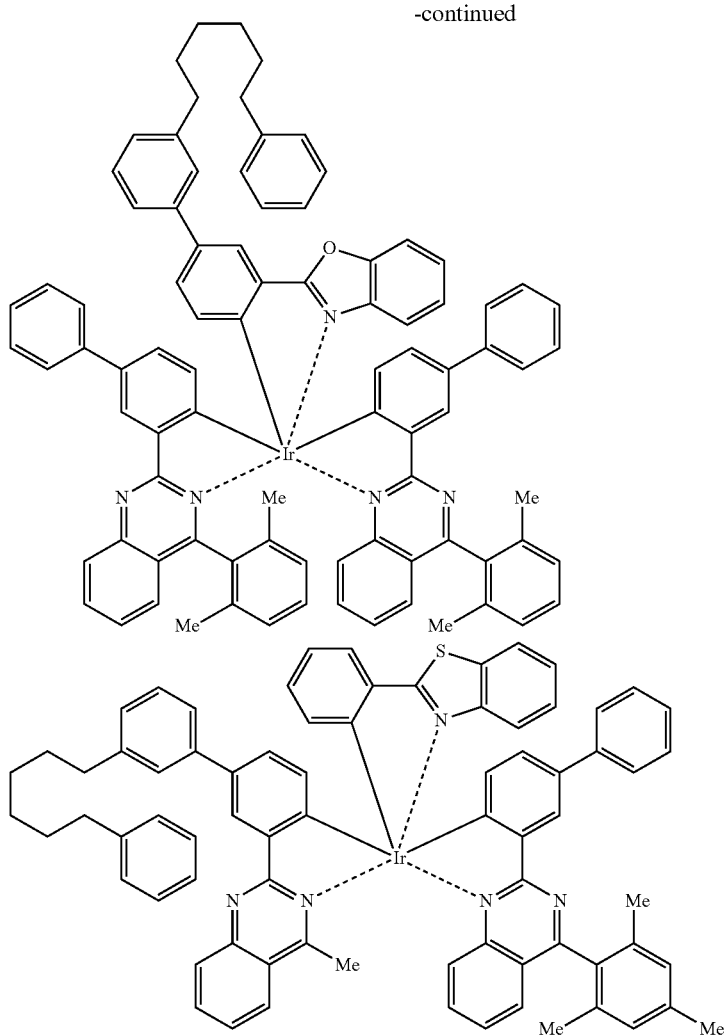
(3) Examples of the iridium complex compound in which $L^1$ is formula (2-3), $L^2$ is formula (3-1), and m+n is 3:
[Chem. 17]
-continued
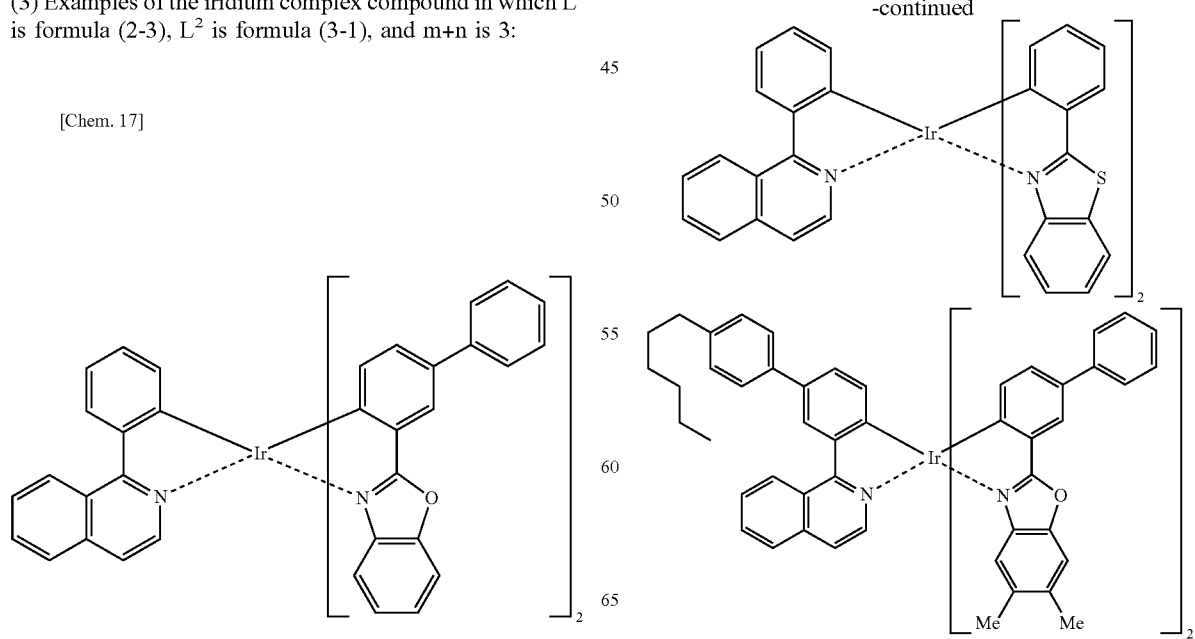

-continued

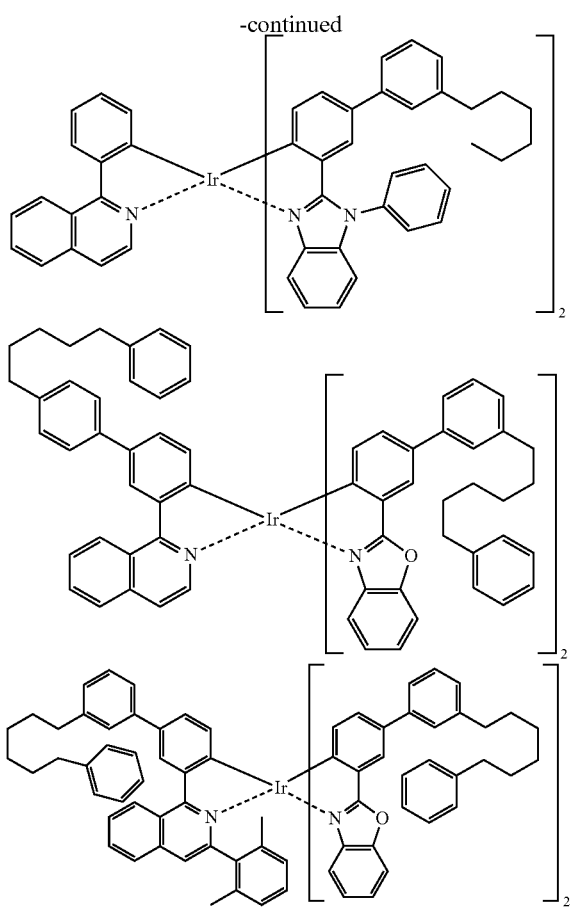

<Structural Features>

The iridium complex compound of the invention produces an effect wherein the compound emits red light with a high quantum yield and an organic electroluminescent element produced using this compound has a high luminescent efficiency. The reasons why this effect is brought about are thought to be as follows, from structural features.

It is generally known that red-luminescent iridium complex compounds are small in energy gap as compared with green-luminescent iridium complexes and hence have a high non-radiative transition rate (the energy gap law). Due to the small energy gap, red-luminescent iridium complex compounds have a relatively low luminescent quantum yield. Consequently, for improving the luminescent quantum yield of an iridium complex compound which emits red light, it is necessary to enhance the MLCT (metal to ligand charge transfer) properties and thereby heighten the radiative transfer rate, which participates in luminescence.

The present inventors investigated correlations between the structures and properties of various iridium complex compounds. As a result, the inventors have discovered that in the case where an iridium complex compound has both an electron-withdrawing ligand (e.g., a phenylazole ligand or the like) and a ligand contributing to red luminescence (e.g., a phenylquinoline ligand, phenylquinazoline ligand, or the like), this iridium complex compound emits red light and shows an increased radiative transfer rate. Although the reason therefor is unclear at present, it is presumed that the ligand field splitting of iridium has changed due to the electron-withdrawing ligand and this change has enhanced the MLCT properties, resulting in the increase in radiative transfer rate.

As described above, since the iridium complex compound of the invention has both a phenyl(iso)quinoline or phenylquinazoline ligand and an electron-withdrawing ligand such as a phenylazole ligand, the iridium complex compound emits red light with a satisfactory quantum yield, making it possible to provide an organic electroluminescent element in which the compound is utilized and which has a high luminescent efficiency.

<Applications of the Iridium Complex Compound>

The iridium complex compound of the invention is suitable for use as a material for organic electroluminescent elements, i.e., as an organic-electroluminescent-element material, and is suitable also for use as a luminescent material for organic electroluminescent elements, other luminescent elements, etc.

<Composition Containing the Iridium Complex Compound>

Since the iridium complex compound of the invention has excellent solubility, it is preferred to use the compound together with a solvent. A composition containing the iridium complex compound of the invention and a solvent (hereinafter often referred to as "iridium-complex-compound-containing composition") is explained below.

The iridium-complex-compound-containing composition of the invention includes the iridium complex compound of the invention described above and a solvent. The iridium-complex-compound-containing composition of the invention is usually used for forming a layer or a film by a wet-process form formation method, and it is especially preferable that the composition be used for forming an organic layer of an organic electroluminescent element. It is especially preferable that the organic layer should be a emission layer.

Namely, it is preferable that the iridium-complex-compound-containing composition should be a composition for organic electroluminescent elements, and it is especially preferred to use the composition as a composition for luminescent-layer formation.

The content of the iridium complex compound of the invention in the iridium-complex-compound-containing composition is usually 0.001% by weight or higher, preferably 0.005% by weight or higher, and is usually 50% by weight or less, preferably 30% by weight of less. By regulating the content of the iridium complex compound in the composition so as to be within that range, this composition, when used in an organic-electroluminescent-element application, can be made to give an organic electroluminescent element in which holes and electrons are efficiently injected into the emission layer from adjoining layers (for example, the hole transport layer and the hole blocking layer) and which has a reduced operating voltage. Incidentally, only one iridium complex compound of the invention may be contained in the iridium-complex-compound-containing composition or two or more iridium complex compounds of the invention may be contained in combination in the composition.

In the case where the iridium-complex-compound-containing composition of the invention is to be used, for example, for an organic electroluminescent element, this composition can contain a charge-transporting compound for use in organic electroluminescent elements, in particular, in emission layers, besides the iridium complex compound described above and the solvent.

In the case where the iridium-complex-compound-containing composition of the invention is to be used for forming the emission layer of an organic electroluminescent element, it is preferable that this composition should contain the iridium complex compound of the invention as a dopant material and another charge-transporting compound as a host material.

The solvent contained in the iridium-complex-compound-containing composition of the invention is a liquid ingredient which has volatility and is used in order to form, by a wet-process film formation method, a layer which contains the iridium complex compound.

Since the iridium complex compound of the invention, which is a solute, has high solubility, the solvent is not particularly limited so long as the charge-transporting compound which will be described later dissolves therein satisfactorily.

Preferred examples of the solvent include: alkanes such as n-decane, cyclohexane, ethylcyclohexane, decaline, and bicyclohexane; aromatic hydrocarbons such as toluene, xylene, mesitylene, phenylcyclohexane, and tetralin; halogenated aromatic hydrocarbons such as chlorobenzene, dichlorobenzene, and trichlorobenzene; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, 2,4-dimethylanisole, and diphenyl ether; aromatic esters such as phenyl acetate, phenyl propionate, methyl benzoate, ethyl benzoate, propyl benzoate, and n-butyl benzoate; alicyclic ketones such as cyclohexanone, cyclooctanone, and fenchone; alicyclic alcohols such as cyclohexanol and cyclooctanol; aliphatic ketones such as methyl ethyl ketone and dibutyl ketone; aliphatic alcohols such as butanol and hexanol; and aliphatic ethers such as ethylene glycol dimethyl ether, ethylene glycol diethyl ether, and propylene glycol 1-monomethyl ether acetate (PGMEA). Preferred of these are alkanes and aromatic hydrocarbons. In particular, phenylcyclohexane has a viscosity and a boiling point which are preferred in wet film formation processes.

One of these solvents may be used alone, or any desired two or more thereof may be used in combination in any desired proportion.

The solvent has a boiling point of usually 80° C. or higher, preferably 100° C. or higher, more preferably 150° C. or higher, especially preferably 200° C. or higher. The boiling point thereof is usually 300° C. or lower, preferably 280° C. or lower, more preferably 250° C. or lower. In case where the boiling point thereof is lower than the lower limit, there is a possibility that film formation stability during wet-process film formation might decrease due to solvent vaporization from the composition.

The content of the solvent per 100 parts by weight of the composition is preferably 10 parts by weight or more, more preferably 50 parts by weight or more, especially preferably 80 parts by weight or more, and is preferably 99.95 parts by weight or less, more preferably 99.9 parts by weight or less, especially preferably 99.8 parts by weight or less.

The emission layer usually has a thickness of about 3-200 nm. However, in case where the content of the solvent is less than that lower limit, there is a possibility that the composition might have too high viscosity and hence have reduced applicability for film formation. Meanwhile, in case where the content of the solvent exceeds the upper limit, there is a tendency that film formation is difficult because the film obtained by solvent removal after film formation cannot have a sufficiently large thickness.

As the other charge-transporting compound which can be contained in the iridium-complex-compound-containing composition of the invention, use can be made of ones which have hitherto been used as materials for organic electroluminescent elements. Examples thereof include the charge-transporting compounds shown in International Publication WO 2012/096263.

One of these charge-transporting compounds may be used alone, or any desired two or more thereof may be used in combination in any desired proportion.

The content of the other charge-transporting compound in the iridium-complex-compound-containing composition of the invention, per 100 parts by weight of the composition, is usually 0.01 part by weight or more, preferably 0.05 parts by weight or more, and is usually 50 parts by weight or less, preferably 30 parts by weight or less.

The iridium-complex-compound-containing composition of the invention may further contain compounds other than the compounds, etc. shown above, according to need. For example, besides the solvent shown above, another solvent may be contained. Examples of such solvent include: amides such as N,N-dimethylformamide and N,N-dimethylacetamide; and dimethyl sulfoxide. One of these may be used alone, or any desired two or more thereof may be used in combination in any desired proportion.

[Organic Electroluminescent Element]

The organic electroluminescent element of the invention includes a substrate and, disposed thereover, at least an anode, a cathode, and one or more organic layers interposed between the anode and the cathode, and is characterized in that at least one of the organic layers includes the complex compound of the invention. The organic layers include a emission layer.

The organic layer which contains the complex compound of the invention preferably is a layer formed using the composition according to the invention, and more preferably is a layer formed therefrom by a wet-process film formation method. It is preferable that the layer formed by a wet-process film formation method should be the emission layer.

The FIGURE is a schematic cross-sectional view which shows an example of a preferred structure of an organic electroluminescent element 10 of the invention. In The FIGURE, numeral 1 denotes a substrate, 2 denotes an anode, 3 denotes a hole injection layer, 4 denotes a hole transport layer, 5 denotes a emission layer, 6 denotes a hole blocking layer, 7 denotes an electron transport layer, 8 denotes an electron injection layer, and 9 denotes a cathode.

[1] Substrate

The substrate 1 serves as the support of the organic electroluminescent element, and use is made of a plate of quartz or glass, a metal sheet, a metal foil, a plastic film or sheet, or the like. Especially preferred is a glass plate or a plate of a transparent synthetic resin such as a polyester, polymethacrylates, polycarbonate, or polysulfone. In the case of using a synthetic-resin substrate, it is necessary to take account of gas barrier properties. In case where the substrate has too low gas barrier properties, there are cases where the surrounding air passes through the substrate to deteriorate the organic electroluminescent element. Consequently, one of preferred methods is to dispose a dense silicon oxide film or the like on at least one surface of the synthetic-resin substrate to ensure gas barrier properties.

[2] Anode

An anode 2 is disposed over the substrate 1. The anode 2 serves to inject holes into a layer located on the emission layer side (for example, the hole injection layer 3, hole transport layer 4, or emission layer 5).

This anode 2 is usually constituted of a metal such as aluminum, gold, silver, nickel, palladium, or platinum, a metal oxide such as an oxide of indium and/or tin, a metal halide such as copper iodide, carbon black, a conductive polymer such as poly(3-methylthiophene), polypyrrole, or polyaniline, or the like.

The anode 2 is frequently formed usually by sputtering, vacuum deposition, or the like. In the case where fine particles of a metal such as silver, fine particles of copper iodide or the like, carbon black, fine particles of a conductive metal oxide, a fine powder of a conductive polymer, or the like is used to form the anode, use may be made of a method in which such a particulate material is dispersed in an appropriate binder resin solution and the dispersion is applied to the substrate 1 to thereby form an anode 2. Furthermore, in the case of a conductive polymer, use may be made of a method in which a thin film is directly formed on the substrate 1 by electrolytic polymerization or the conductive polymer is applied to the substrate 1 to form an anode 2 (*Appl. Phys. Lett.*, Vol. 60, p. 2711, 1992).

The anode 2 usually has a single-layer structure. However, the anode 2 can be made to have a multilayer structure configured of a plurality of materials, according to need.

The thickness of the anode 2 varies depending on the transparency required. In the case where transparency is required, it is desirable that the anode 2 should have a visible-light transmittance of usually 60% or higher, preferably 80% or higher. In this case, the thickness of the anode is usually 5 nm or larger, preferably 10 nm or larger, and is usually about 1,000 nm or less, preferably about 500 nm or less.

In the case where the anode 2 may be opaque, this anode 2 may have any desired thickness and may be the substrate 1. It is also possible to superpose a layer of another conductive material on the anode 2.

It is preferred to subject the anode surface to an ultraviolet (UV)/ozone treatment or a treatment with an oxygen plasma or argon plasma, for the purpose of removing impurities adherent to the anode to regulate the ionization potential and improve the hole injection properties.

[3] Hole Injection Layer

The hole injection layer 3 is a layer which transports holes from the anode 2 to the emission layer 5, and is usually formed on the anode 2. For forming the hole injection layer 3 according to the invention, either a vacuum deposition method or a wet-process film formation method may be used without particular limitations. However, it is preferred to form the layer by a wet-process form formation method from the standpoint of diminishing dark spots.

The thickness of the hole injection layer 3 is usually 5 nm or larger, preferably 10 nm or larger, and is usually 1,000 nm or less, preferably 500 nm or less.

<Formation of Hole Injection Layer by Wet-Process Film Formation Method>

In the case where a hole injection layer 3 is formed by a wet-process film formation method, the hole injection layer 3 is formed usually by mixing the materials for constituting the hole injection layer 3 with an appropriate solvent (solvent for hole injection layer formation) to prepare a composition for film formation (composition for hole injection layer formation), applying the composition for hole injection layer formation by an appropriate technique on the layer (usually the anode) which is to underlie the hole injection layer 3, and drying the resultant coating film.

(Hole-Transporting Compound)

The composition for hole injection layer formation usually includes both a hole-transporting compound as a constituent material for the hole injection layer and a solvent. The hole-transporting compound may usually be a polymer compound such as a polymer or a low-molecular-weight compound such as a monomer, so long as the compound is one which has hole-transporting properties and is for use in the hole injection layers of organic electroluminescent elements. However, it is preferable that the hole-transporting compound should be a polymer compound.

The hole-transporting compound preferably is a compound having an ionization potential of 4.5-6.0 eV, from the standpoint of barrier to charge injection from the anode 2 into the hole injection layer 3.

Examples of the hole-transporting compound include aromatic amine derivatives, phthalocyanine derivatives, porphyrin derivatives, oligothiophene derivatives, polythiophene derivatives, benzylphenyl derivatives, a compound configured of tertiary amines connected to each other by a fluorene group, hydrazone derivatives, silazane derivatives, silanamine derivatives, phosphamine derivatives, quinacridone derivatives, polyaniline derivatives, polypyrrole derivatives, polyphenylenevinylene derivatives, polythienylenevinylene derivatives, polyquinoline derivatives, polyquinoxaline derivatives, and carbon.

The term "derivatives" in the invention has the following meaning. In the case of aromatic amine derivatives, for example, that term means a conception which includes aromatic amines themselves and compounds in each of which the main framework is an aromatic amine, and the aromatic amine derivatives may be either polymers or monomers.

Any one of such hole-transporting compounds for use as a material for the hole injection layer 3 may be contained alone, or two or more thereof may be contained. In the case where two or more hole-transporting compounds are contained, the combination is not limited. However, it is preferred to use one or more aromatic tertiary amine polymer compounds in combination with one or more other hole-transporting compounds.

From the standpoints of non-crystallinity and visible-light transmittance, aromatic amine compounds are preferred of the compounds shown above as examples, and aromatic tertiary amine compounds are especially preferred. The term "aromatic tertiary amine compounds" herein means compounds each having an aromatic tertiary amine structure, and these compounds include compounds each having a group derived from an aromatic tertiary amine.

The aromatic tertiary amine compounds are not particularly limited in the kinds thereof. However, from the standpoint of even luminescence due to a surface-smoothing effect, polymer compounds having a weight-average molecular weight of 1,000-1,000,000 (polymer type compounds each made up of consecutive repeating units) are more preferred. Preferred examples of such aromatic tertiary amine polymer compounds may be selected from among conventionally known hole-transporting compounds, without particular problems. Examples thereof include the polymer compounds disclosed in JP-A-2000-036390, JP-A-2007-169606, and JP-A-2009-212510.

(Electron-Accepting Compound)

It is preferable that the composition for charge injection layer formation should contain an electron-accepting compound as a constituent material for the hole injection layer.

The electron-accepting compound preferably is a compound which has oxidative ability and has the ability to accept one electron from the hole-transporting compound described above. Specifically, compounds having an electron affinity of 4 eV or higher are preferred, and compounds having an electron affinity of 5 eV or higher are more preferred.

Examples of such electron-accepting compounds include one or more compounds selected from the group consisting of triarylboron compounds, metal halides, Lewis acids, organic acids, onium salts, salts of arylamines with metal halides, and salts of arylamines with Lewis acids. More specifically, examples thereof include: inorganic compounds having a high valence, such as iron(III) chloride (JP-A-11-251067) and ammonium peroxodisulfate; cyano compounds such as tetracyanoethylene; aromatic boron compounds such as tris(pentafluorophenyl)borane (JP-A-2003-31365); onium salts substituted with an organic group (International Publication WO 2005/089024); fullerene derivatives; iodine; and sulfonic acid ions such as polystyrenesulfonic acid ions, alkylbenzenesulfonic acid ions, and camphorsulfonic acid ions.

These electron-accepting compounds can improve the electrical conductivity of the hole injection layer by oxidizing the hole-transporting compound.

The content of the electron-accepting compound in the hole injection layer or in the composition for hole injection layer formation, based on the hole-transporting compound, is usually 0.1% by mole or higher, preferably 1% by mole or higher, but is usually 100% by mole or less, preferably 40% by mole or less.

(Solvent)

It is preferable that the solvent in the composition for hole injection layer formation to be used in a wet-process film formation method should include at least one compound in which the constituent materials for the hole injection layer can dissolve. This solvent has a boiling point which is usually 110° C. or higher, preferably 140° C. or higher, in particular 200° C. or higher, and is usually 400° C. or lower, in particular 300° C. or lower. In case where the solvent has too low a boiling point, there is a possibility that the drying rate might be too high, resulting in a deterioration in film quality. Meanwhile, in case where the solvent has too high a boiling point, it is necessary to use a higher temperature in the drying step and there is a possibility that the elevated temperature might adversely affect other layers or the substrate.

Examples of the solvent include ether solvents, ester solvents, aromatic hydrocarbon solvents, and amide solvents. There are no particular problems so long as a conventional solvent is selected. Examples thereof are shown in JP-A-2007-169606, International Publication WO 2006/087945, and JP-A-2009-212510.

(Method for Film Formation)

After preparation of the composition for hole injection layer formation, this composition is applied by a wet-process film formation method on the layer (usually the anode 2) which is to underlie the hole injection layer 3, and the resultant coating film is dried. Thus, the hole injection layer 3 can be formed. Conventional methods disclosed, for example, in JP-A-2009-212510 can be applied.

<Formation of Hole Injection Layer by Vacuum Deposition Method>

In the case where a hole injection layer 3 is formed by vacuum deposition, one or more constituent materials for the hole injection layer 3 (for example, the hole-transporting compound and electron-accepting compound described above) are put in one or more crucibles disposed in a vacuum vessel (when two or more materials are used, these materials are put in respective crucibles), and the inside of this vacuum vessel is evacuated with an appropriate vacuum pump to about $10^{-4}$ Pa. Thereafter, the one or more crucibles are heated (when two or more materials are used, the respective crucibles are heated) to vaporize the material(s) while controlling the rate(s) of vaporization (when two or more materials are used, the materials are vaporized while independently controlling the rates of vaporization thereof) and to thereby form a hole injection layer 3 on the anode 2 of a substrate placed so as to face the crucible(s). Incidentally, in the case of using two or more materials, use may be made of a method in which a mixture of these materials is put in a crucible, heated, and vaporized to form a hole injection layer 3.

The degree of vacuum during the deposition is not limited so long as the effects of the invention are considerably lessened. However, the pressure is usually $0.1 \times 10^{-7}$ Torr $(0.13 \times 10^{-5}$ Pa) or higher and is usually $9.0 \times 10^{-6}$ Torr $(12.0 \times 10^{-4}$ Pa) or lower. The rate of deposition is not limited so long as the effects of the invention are considerably lessened. However, the rate of deposition is usually 0.1 Å/sec or higher and is usually 5.0 Å/sec or less.

[4] Hole Transport Layer

A hole transport layer 4 can be formed on the hole injection layer 3 when there is the hole injection layer, or be formed on the anode 2 when there is no hole injection layer 3. The organic electroluminescent element of the invention may have a configuration wherein the hole transport layer has been omitted.

For forming the hole transport layer 4, either a vacuum deposition method or a wet-process film formation method may be used without particular limitations. However, it is preferred to form the layer by a wet-process film formation method, from the standpoint of diminishing dark spots.

As a material for forming the hole transport layer 4, it is preferred to employ a material which has high hole-transporting properties and which can efficiently transport injected holes. From this standpoint, it is preferable that the material should have a low ionization potential, high transparency to visible light, a high hole mobility, and excellent stability and be less apt to generate, during production or use, impurities which serve as traps. Furthermore, since the hole transport layer 4 is in contact with the emission layer 5 in many cases, it s preferable that the material should not reduce the efficiency by quenching the light emitted from the emission layer 5 or by forming exciplexes with the emission layer 5.

As such a material for the hole transport layer 4, use may be made of any material which has conventionally been in use as a constituent material for hole transport layers. Examples thereof include the compounds shown above as examples of the hole-transporting compound to be used in the hole injection layer 3 described above. There are no particular problems so long as a conventionally known hole-transporting compound is selected. For example, the compounds disclosed in JP-A-2009-212510 can be employed.

[5] Emission Layer

A emission layer 5 is usually disposed on the hole transport layer 4. The emission layer 5 is a layer which, between the electrodes to which an electric filed is being applied, is excited by the recombination of holes injected via the hole injection layer 3 from the anode 2 with electrons injected via the electron transport layer 7 from the cathode 9 and which thus serves as the main luminescence source.

It is preferable that the emission layer 5 should include a luminescent material (dopant) and one or more host materials. The emission layer 5 may be formed by a vacuum deposition method using the iridium complex compound of the invention. However, it is especially preferable that the emission layer 5 should be a layer produced by a wet-process film formation method using the iridium-complex-compound-containing composition of the invention.

The term "wet-process film formation method" herein means a method in which a composition containing a solvent is applied for film formation by a wet process such as spin coating, dip coating, die coating, bar coating, blade coating, roll coating, spray coating, capillary coating, ink-jet method, screen printing, gravure printing, or flexographic printing, as described above.

The emission layer 5 may contain other materials and ingredients so long as the performance of the invention is not impaired thereby. In general, in the case of organic electroluminescent elements employing the same materials, the one in which the thickness of the films disposed between the electrodes is smaller has an increased effective electric field and hence a higher injected current, resulting in a decrease in operating voltage. Consequently, organic electroluminescent elements in which the total thickness of the films disposed between the electrodes is smaller have a reduced operating voltage. However, in case where the thickness thereof is too small, short-circuiting occurs due to projections attributable to an electrode of ITO, etc. Some degree of film thickness is hence necessary.

In the invention, in the case where the organic electroluminescent element has one or more organic layers such as, for example, the hole injection layer 3 and the electron transport layer 7 which will be described later, besides the emission layer 5, the total thickness of the emission layer 5 and the other organic layers, e.g., the hole injection layer 3 and the electron transport layer 7, is usually 30 nm or larger, preferably 50 nm or larger, more preferably 100 nm or larger, and is usually 1,000 nm or less, preferably 700 nm or less, more preferably 500 nm or less. Meanwhile, in cases when the layers other than the emission layer 5, such as the hole injection layer 3 and the electron injection layer 8 which will be described later, have high electrical conductivity, charges are injected into the emission layer 5 in an increased amount. It is therefore possible to lower the operating voltage while keeping the total film thickness at a certain value, for example, by increasing the thickness of the hole injection layer 3 and reducing the thickness of the emission layer 5.

Consequently, the thickness of the emission layer 5 is usually 10 nm or larger, preferably 20 nm or larger, and is usually 300 nm or less, preferably 200 nm or less. In the case where the organic electroluminescent element of the invention has the emission layer 5 only between the anode and the cathode, the thickness of this emission layer 5 is usually 30 nm or larger, preferably 50 nm or larger, and is usually 500 nm or less, preferably 300 nm or less.

[6] Hole Blocking Layer

A hole blocking layer 6 is superposed on the emission layer 5 so as to be in contact with the cathode-side surface of the emission layer 5. Disposition of the hole blocking layer 6 is effective especially when a phosphorescent material is used as a luminescent substance or when a material which emits blue light is used.

The hole blocking layer 6 has the function of confining holes and electrons in the emission layer 5 to improve the luminescent efficiency. Namely, the hole blocking layer 6 not only has the function of inhibiting holes which are moving thereinto from the emission layer 5 from reaching the electron transport layer 7 and of thereby increasing the probability of recombination with electrons within the emission layer 5 and confining the resultant excitons in the emission layer 5, but also has the function of efficiently transporting, toward the emission layer 5, the electrons injected from the electron transport layer 7.

Examples of properties required of the material for constituting the hole injection layer 6 include: to have a high electron mobility and a low hole mobility; to have a large energy gap (difference between HOMO and LUMO); and to have a high excited triplet level (T1).

Examples of hole blocking layer materials which satisfy such requirements include metal complexes such as mixed-ligand complexes, e.g., bis(2-methyl-8-quinolinolato)(phenolato)aluminum and bis(2-methyl-8-quinolinolato)(triphenylsinolato)aluminum, and dinuclear metal complexes, e.g., bis(2-methyl-8-quinolato)aluminum-μ-oxobis(2-methyl-8-quinolato)aluminum, styryl compounds such as distyrylbiphenyl derivatives (JP-A-11-242996), triazole derivatives such as 3-(4-biphenylyl)-4-phenyl-5-(4-tert-butylphenyl)-1,2,4-triazole (JP-A-7-41759), and phenanthroline derivatives such as bathocuproine (JP-A-10-79297).

Furthermore, the compound described in International Publication WO 2005/022962 which has at least one pyridine ring substituted at the 2, 4, and 6 positions is also preferred as a hole blocking material. The thickness of the hole blocking layer 6 is usually 0.3 nm or larger, preferably 0.5 nm or larger, and is usually 100 nm or less, preferably 50 nm or less. Although the hole blocking layer 6 can be formed by the same methods as for the hole injection layer 3, the vacuum deposition method is usually used.

[7] Electron Transport Layer

An electron transport layer 7 is disposed between the hole blocking layer 6 and the electron injection layer 8 for the purpose of further improving the luminescent efficiency of the element. The electron transport layer 7 is constituted of a compound that, between the electrodes to which an electric field is being applied, is capable of efficiently transporting, toward the emission layer 5, the electrons injected from the cathode 9. The electron-transporting compound to be used in the electron transport layer 7 must be a compound with which the efficiency of electron injection from the cathode 9 or electron injection layer 8 is rendered high and which has a high electron mobility and is capable of efficiently transporting injected electrons.

Examples of materials which satisfy such requirements include metal complexes such as aluminum complexes of 8-hydroxyquinoline (JP-A-59-194393), metal complexes of 10-hydroxybenzo[h]quinoline, oxadiazole derivatives, distyrylbiphenyl derivatives, silole derivatives, 3- or 5-hydroxyflavone metal complexes, benzoxazole metal complexes, benzothiazole metal complexes, trisbenzimidazolylbenzene (U.S. Pat. No. 5,645,948), quinoxaline compounds (JP-A-6-207169), phenanthroline derivatives (JP-A-5-331459), 2-t-butyl-9,10-N,N'-dicyanoanthraquinone diimine, n-type hydrogenated amorphous silicon carbide, n-type zinc sulfide, and n-type zinc selenide.

The thickness of the electron transport layer 7 may be as follows. A lower limit thereof is usually about 1 nm, preferably about 5 nm, and an upper limit thereof is usually about 300 nm, preferably about 100 nm.

Although the electron transport layer 7 may be formed by a wet-process film formation method or a vacuum deposition method in the same manner as for the hole injection layer 3, a vacuum deposition method is usually used.

[8] Electron Injection Layer

The electron injection layer 8 serves to efficiently inject, into the emission layer 5, the electrons injected from the cathode 9. From the standpoint of efficient injection of electrons, a metal having a low work function is preferred as the material for constituting the electron injection layer 8, and use is made of an alkali metal such as sodium or cesium or an alkaline earth metal such as barium or calcium. The thickness of the electron injection layer 8 is preferably 0.1-5 nm.

To interpose an ultrathin insulating film (0.1-5 nm) of LiF, $MgF_2$, $Li_2O$, $Cs_2CO_3$, or the like between the cathode 9 and the electron transport layer 7 is also an effective means for improving the efficiency of the element (*Appl. Phys. Lett.*, Vol. 70, p. 152, 1997; JP-A-10-74586; *IEEE Trans. Electron. Devices*, Vol. 44, p. 1245, 1997; *SID* 04 *Digest*, p. 154). Furthermore, to dope an organic electron transport material represented by nitrogen-containing heterocyclic compounds such as basophenanthroline or by metal complexes such as aluminum complexes of 8-hydroxyquinoline with an alkali metal such as sodium, potassium, cesium, lithium, or rubidium (as described in JP-A-10-270171, JP-A-2002-100478, JP-A-2002-100482, etc.) is preferred because the doping can improve the electron injection/transport properties and further attain excellent film quality. In this case, the thickness of the film is usually 5 nm or larger, preferably 10 nm or larger, and is usually 200 nm or less, preferably 100 nm or less.

[9] Cathode

The cathode 9 serves to inject electrons into the layer located on the emission layer side (e.g., the electron injection layer 8 or the emission layer 5). Although any of the materials usable as the anode 2 can be used as the material for the cathode 9, a metal having a low work function is preferred from the standpoint of efficient injection of electrons. Use may be made of appropriate metals such as tin, magnesium, indium, calcium, aluminum, and silver or alloys of these metals. Specific examples thereof include electrodes of alloys having a low work function, such as magnesium-silver alloys, magnesium-indium alloys, and aluminum-lithium alloys.

The thickness of the cathode 9 is usually the same as the anode 2.

For the purpose of protecting the cathode made of a metal having a low work function, a layer of a metal which has a high work function and is stable to the air may be superposed on the cathode. Thus, the stability of the organic electroluminescent element can be enhanced. For this purpose, use is made of a metal such as aluminum, silver, copper, nickel, chromium, gold, or platinum.

[10]. Other Constituent Layers

Explanations were given above mainly on elements having the layer configuration shown in The FIGURE. However, the organic electroluminescent element of the invention may have any desired layers, besides the layers explained above, between the anode 2 and the emission layer 5 and between the cathode 9 and the emission layer 5, or any of the layers other than the emission layer 5 may be omitted, so long as the performance of the element is not impaired thereby.

It is also effective to dispose an electron blocking layer between the hole transport layer 4 and the emission layer 5 for the same purpose as that of the hole blocking layer 6. The electron blocking layer not only has the function of inhibiting electrons which are moving thereinto from the emission layer 5 from reaching the hole transport layer 4 and of thereby increasing the probability of recombination with holes within the emission layer 5 and confining the resultant excitons in the emission layer 5, but also has the function of efficiently transporting, toward the emission layer 5, the holes injected from the hole transport layer 4.

Examples of properties required of the electron blocking layer include: to have high hole-transporting properties; to have a large energy gap (difference between HOMO and LUMO); and to have a high excited triplet level (T1). It is preferable that in the case where the emission layer 5 is formed by a wet-process film formation method, the electron blocking layer also should be formed by a wet-process film formation method, since element production is facilitated.

Consequently, it is preferable that the electron blocking layer also should have suitability for wet-process film formation. Examples of materials usable as such electron blocking layer include copolymers of dioctylfluorene with triphenylamine which are represented by F8-TFB (International Publication WO 2004/084260).

Incidentally, constituent layers can be superposed in the order reverse to that shown in The FIGURE. Namely, a cathode 9, electron injection layer 8, electron transport layer 7, hole blocking layer 6, emission layer 5, hole transport layer 4, hole injection layer 3, and anode 2 may be superposed in this order on a substrate 1. It is also possible to dispose the organic electroluminescent element of the invention between two substrates, at least one of which is highly transparent.

Furthermore, it is possible to configure a structure made up of a plurality of stacked stages each having the layer configuration shown in The FIGURE (structure obtained by stacking a plurality of luminescent units). In this case, $V_2O_5$ or the like, for example, can be used as a charge generation layer in place of each of the interfacial layers located between the stages (i.e., between the luminescent units) (in the case where the anode is ITO and the cathode is Al, then the charge generation layer is used in place of these two layers). This configuration brings about a decrease in barrier between the stages, and is more preferred from the standpoints of luminescent efficiency and operating voltage <Display Device and Illuminator>

The display device and illuminator of the invention employ the organic electroluminescent element of the invention described above. The display device and illuminator of the invention are not particularly limited in the types and structures thereof, and can be assembled using the organic electroluminescent element of the invention in accordance with ordinary methods.

For example, the display device and illuminator of the invention can be produced by methods such as those described in Yūki EL Disupurei (Ohmsha, Ltd., published on Aug. 20, 2004, written by TOKITO Shizuo, ADACHI Chihaya, and MURATA Hideyuki).

EXAMPLES

The invention will be explained below in more detail by reference to Examples. However, the invention should not be construed as being limited to the following Examples unless the invention departs from the spirit thereof. Incidentally, the various conditions and values of evaluation results which are given in the following Examples mean preferred upper-limit or lower-limit values in embodiments of the invention. Preferred ranges each may be one which is determined by a combination of the upper limit or lower limit shown above and either the value obtained in any of the following Examples or the values obtained in two or more of the following Examples.

Synthesis Example for Compound D-2 of the Invention Synthesis of Intermediate 8

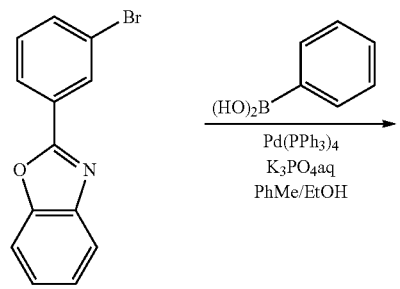

[Chem. 18]

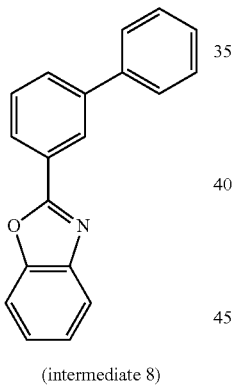

(intermediate 8)

2-(3-Bromophenyl)benzoxazole (25.3 g; 0.091 mol), phenylboronic acid (16.7 g; 0.137 mol), toluene (120 mL), ethanol (60 mL), and an aqueous tripotassium phosphate solution (2.0 mol/L; 115 mL) were introduced in this order, and nitrogen bubbling was then conducted for 45 minutes. Thereto was added Pd(PPh$_3$)$_4$ (2.20 g). Thereafter, the mixture was stirred for 6 hours with heating and refluxing. After the mixture was returned to room temperature, distilled water was added thereto. The resultant mixture was extracted with toluene. The organic layer was washed with saturated aqueous sodium chloride solution and dried with magnesium sulfate, and the solvent was then distilled off under reduced pressure. The residue was subjected to silica gel column chromatography, thereby obtaining intermediate 8 (24.3 g; yield, 98%). The 2-(3-bromophenyl)benzoxazole had been synthesized by the method described in *Organic & Biomolecular Chemistry*, Vol. 9 (No. 14), pp. 5288-5296, 2011.

Synthesis of Intermediate 9

[Chem. 19]

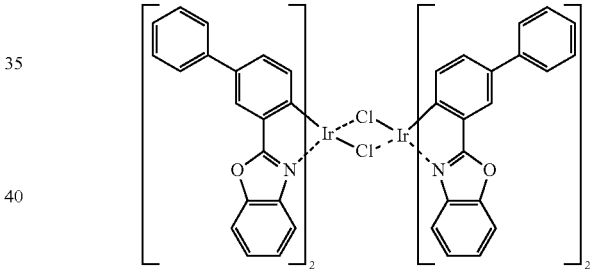

(intermediate 9)

Intermediate 8 (17.4 g; 64.0 mmol), IrCl$_3$.nH$_2$O (10.53 g; 29.1 mmol), 2-EtOEtOH (180 mL), and H$_2$O (30 mL) were introduced in this order, and nitrogen bubbling was conducted for 30 minutes. The mixture was heated at 140° C. for 6 hours and allowed to cool. Methanol was added to the liquid reaction mixture, and the resultant mixture was subjected to suction filtration. The filtration residue was washed with methanol and dried, thereby obtaining intermediate 9 (21.7 g; yield, 97%).

Synthesis of Compound D-2

[Chem. 20]

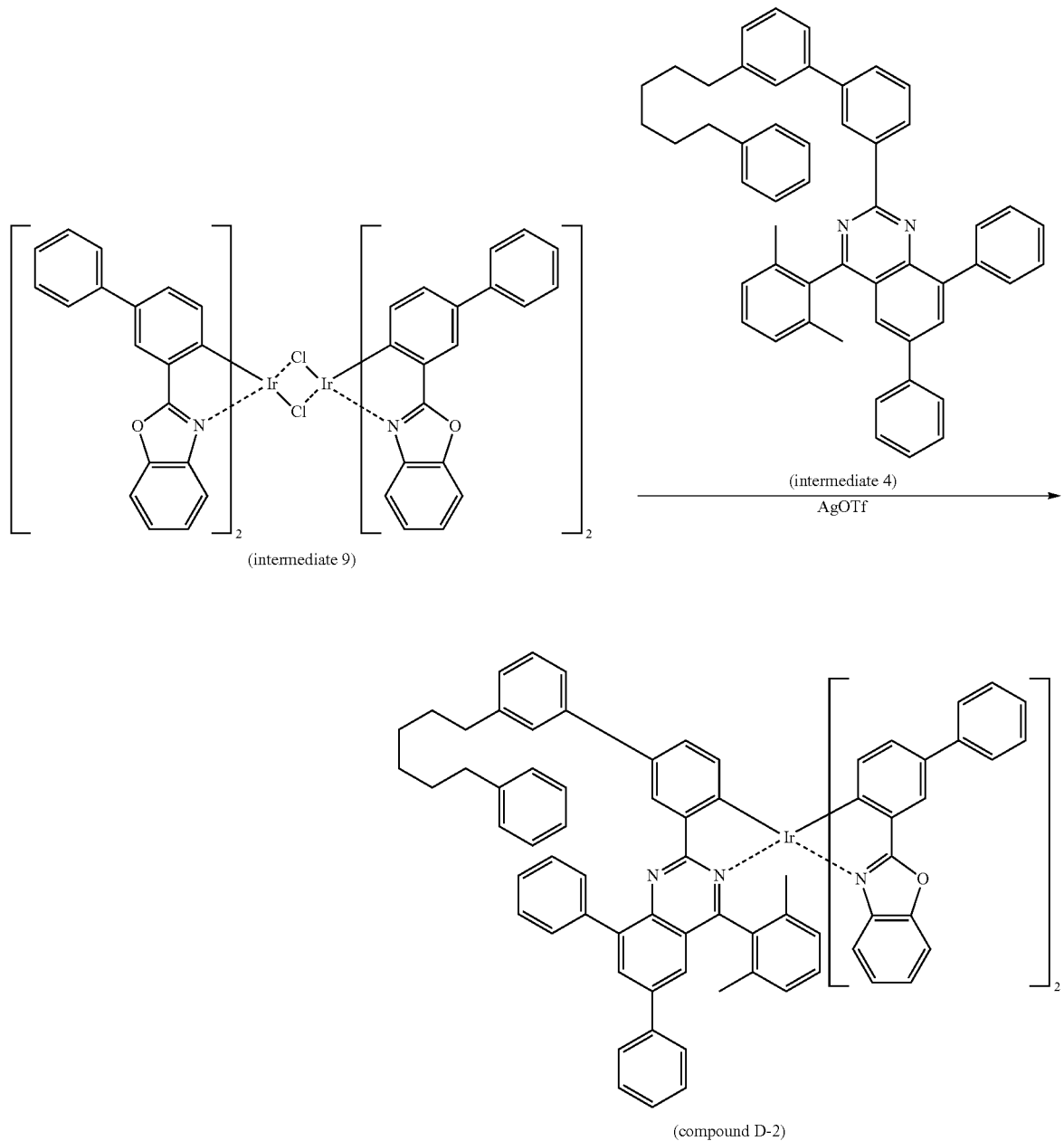

In a nitrogen atmosphere, intermediate 9 (5.37 g; 3.49 mmol) and intermediate 4 (24.4 g; 34.9 mmol) were introduced, and the contents were heated with an oil bath of 180° C. Silver trifluoromethanesulfonate (3.05 g; 11.8 mol) was added thereto, and the mixture was stirred at 180° C. for 2 hours. This mixture was returned to room temperature and then subjected to column chromatography, thereby obtaining compound D-2 (980 mg; yield, 12%).

The results of a $^1$H-NMR examination of the compound obtained are shown below.

$^1$H-NMR (CDCl$_3$, ppm): 8.50 (d, 1H), 8.26 (d, 1H) 8.09 (d, 2H), 7.89 (d, 1H), 7.79 (d, 1H), 7.71 (d, 2H), 7.62-7.56 (m, 3H), 7.53-7.43 (m, 9H), 7.39-7.00 (m, 23H), 6.94-6.88 (m, 2H), 6.72-6.63 (m, 3H), 6.34 (t, 2H), 5.66 (d, 1H), 2.66-2.58 (m, 4H), 1.94 (s, 3H), 1.67-1.62 (m, 4H), 1.41-1.39 (m, 4H), 0.90 (s, 3H).

The ionization potential thereof determined by photoelectric emission spectroscopy was 5.47 eV.

Synthesis Example for Compound D-3 of the Invention

Synthesis of Intermediate 10

[Chem. 21]

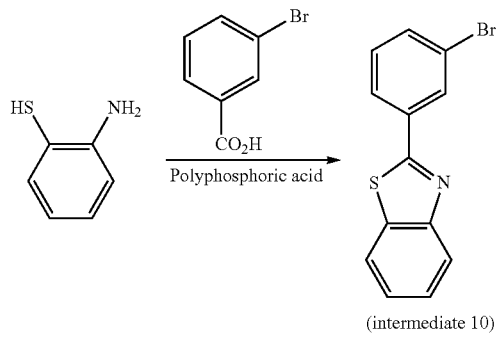

(intermediate 10)

2-Aminothiophenol (25 mL; 0.231 mol), 3-bromobenzoic acid (50.0 g; 0.248 mol), and polyphosphoric acid (60 g) were introduced in this order, and nitrogen displacement was then performed. The contents were stirred for 5 hours with heating at 150° C. After the mixture was returned to room temperature, distilled water was added thereto and the resultant mixture was extracted with methylene chloride. The organic layer was washed with saturated aqueous sodium chloride solution and dried with magnesium sulfate, and the solvent was then distilled off under reduced pressure. The residue was subjected to silica gel column chromatography, thereby obtaining intermediate 10 (60.2 g; yield, 88%). The 2-aminothiophenol and the 3-bromobenzoic acid had been each purchased from Wako Pure Chemical Industries, Ltd.

Synthesis of Intermediate 11

[Chem. 22]

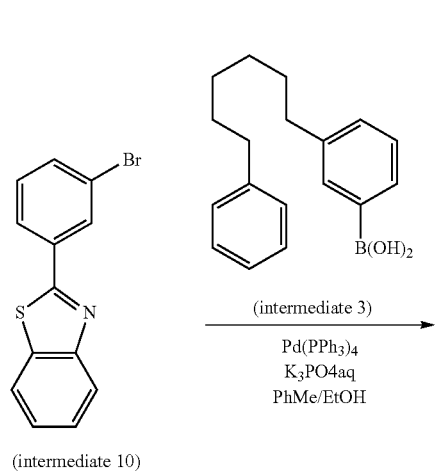

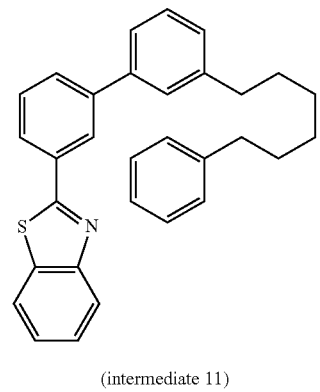

(intermediate 11)

Intermediate 10 (21.6 g; 0.075 mol), intermediate 3 (22.1 g; 0.078 mol), toluene (150 mL), ethanol (75 mL), and an aqueous tripotassium phosphate solution (2.0 mol/L; 95 mL) were introduced in this order, and nitrogen bubbling was then conducted for 45 minutes. Thereto was added Pd(PPh$_3$)$_4$ (2.26 g). Thereafter, the mixture was stirred for 4 hours with heating and refluxing. After the mixture was returned to room temperature, distilled water was added thereto. The resultant mixture was extracted with toluene. The organic layer was washed with saturated aqueous sodium chloride solution and dried with magnesium sulfate, and the solvent was then distilled off under reduced pressure. The residue was subjected to silica gel column chromatography, thereby obtaining intermediate 11 (31.4 g; yield, 94%).

Synthesis of Intermediate 12

[Chem. 22]

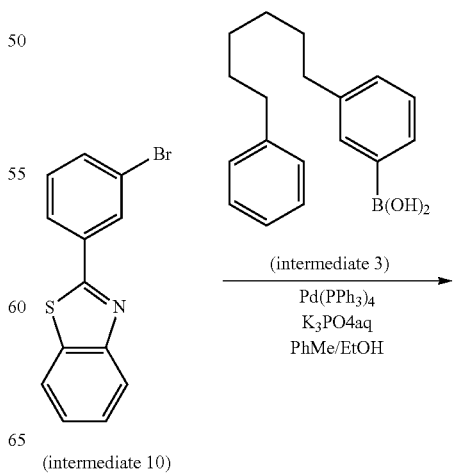

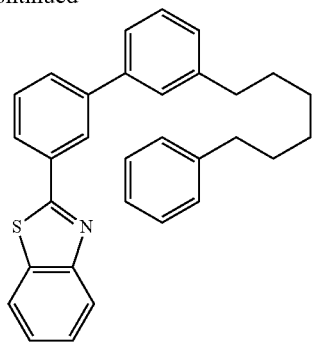

(intermediate 11)

Intermediate 11 (31.4 g; 70.2 mmol), IrCl₃-nH₂O (11.95 g; 33.4 mmol), 2-EtOEtOH (315 mL), and H₂O (30 mL) were introduced in this order, and nitrogen bubbling was conducted for 30 minutes. The mixture was heated at 140° C. for 3 hours and allowed to cool. Methanol was added to the liquid reaction mixture, and the resultant mixture was subjected to suction filtration. The filtration residue was washed with methanol and dried, thereby obtaining intermediate 12 (34.7 g; yield, 93%).

Synthesis of Intermediate 13

[Chem. 24]

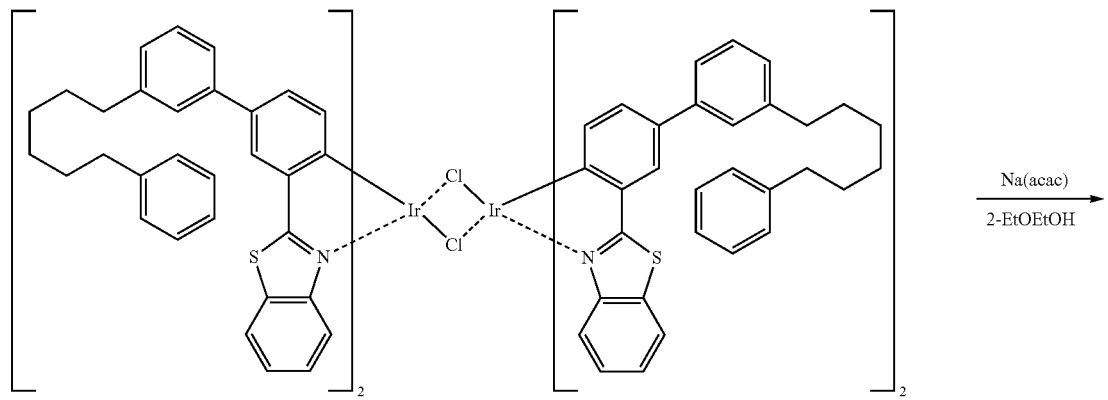

(intermediate 12)

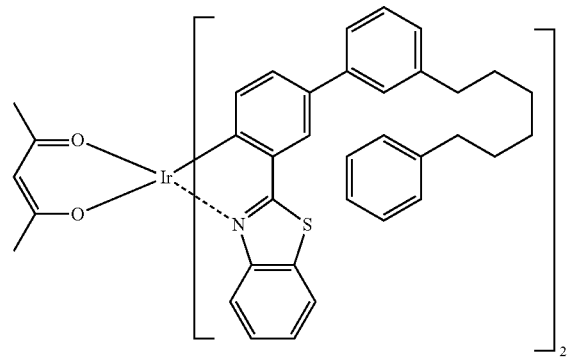

(intermediate 13)

Intermediate 12 (20.8 g; 9.28 mmol), acetylacetonatosodium (3.40 g; 27.8 mmol), and 2-EtOEtOH (200 mL) were introduced in this order, and nitrogen bubbling was conducted for 30 minutes. The mixture was heated at 140° C. for 2 hours and allowed to cool. The solvent was distilled off under reduced pressure. Methylene chloride and distilled water were added to the residue to conduct extraction with the methylene chloride. The organic layer was washed with saturated aqueous sodium chloride solution and dried with magnesium sulfate. The solvent was distilled off under reduced pressure, thereby obtaining intermediate 13 (22.8 g; quant.).

Synthesis of Compound D-3

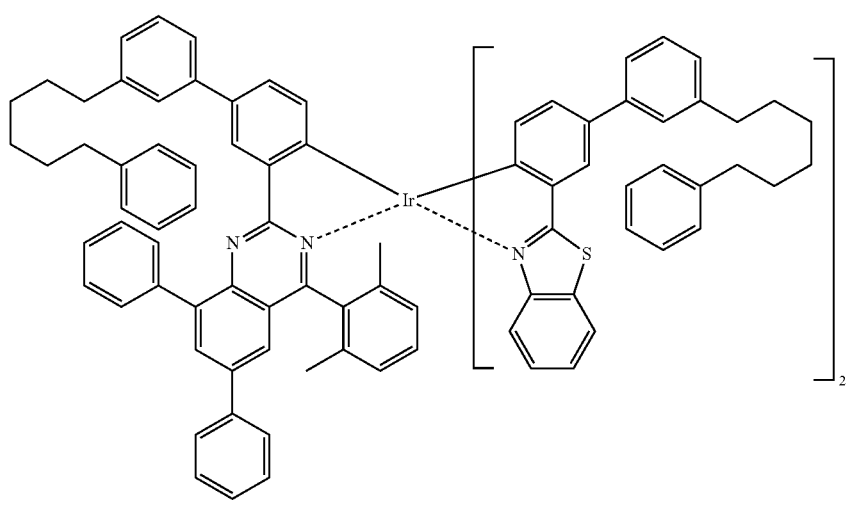

(compound D-3)

In a nitrogen atmosphere, intermediate 13 (1.10 g; 0.929 mmol) and intermediate 4 (3.25 g; 4.65 mmol) were introduced, and the contents were heated with an oil bath of 180° C. Silver trifluoromethanesulfonate (0.41 g; 1.60 mol) was added thereto, and the mixture was stirred at 220° C. for 45 minutes. This mixture was returned to room temperature and then subjected to column chromatography, thereby obtaining compound D-3 (161 mg; yield, 9%). Meanwhile, synthesis of compound D-3 was attempted under the same conditions as in this Synthesis Example, except that the intermediate 13 was replaced with intermediate 12. However, compound D-3 was not obtained.

The results of a $^1$H-NMR examination of the compound obtained are shown below.

$^1$H-NMR (CDCl$_3$, ppm): 8.52 (d, 1H), 8.25 (d, 1H), 8.09 (d, 2H), 7.83-7.77 (m, 2H), 7.63-7.58 (m, 4H), 7.52-6.86 (m, 42H), 6.74-6.51 (m, 6H), 5.71 (d, 1H), 2.70-2.55 (m, 12H), 1.87 (s, 311), 1.71-1.56 (m, 12H), 1.42-1.33 (m, 12H), 0.87 (s, 3H).

The ionization potential thereof determined by photoelectric emission spectroscopy was 5.41 eV.

Synthesis Example for Comparative Compound D-4

Synthesis of Intermediate 14

[Chem. 26]

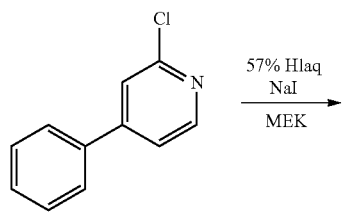

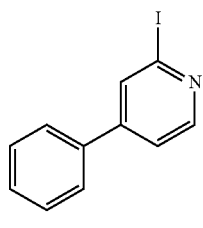

(intermediate 14)

4-Phenyl-2-chloropyridine (40 g), sodium iodide (177 g), and methyl ethyl ketone (350 mL) solution were introduced in this order, and nitrogen bubbling was conducted for 20 minutes. Thereto was added 57% aqueous hydrogen iodide solution (47.3 g). The mixture was heated with refluxing for 17 hours, and was returned to room temperature. Thereafter, water was added thereto, and the resultant mixture was extracted with methylene chloride. The organic layer was washed with saturated aqueous sodium chloride solution and dried with MgSO$_4$, and the solvent was distilled off under reduced pressure. The residue was purified by silica gel column chromatography, thereby obtaining intermediate 14 (50.8 g) having a purity of 88%. The 4-phenyl-2-chloropyridine had been synthesized with reference to the method described in International Publication WO 2010/094242.

Synthesis of Intermediate 15

[Chem. 27]

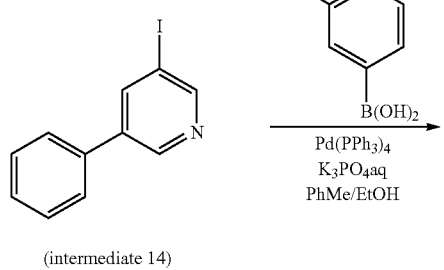

(intermediate 14)

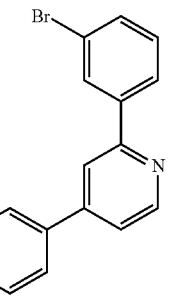

(intermediate 15)

Intermediate 14 (purity, 88%; 50.8 g), 3-bromophenylboronic acid (33.2 g), toluene (232 mL), ethanol (186 mL), and an aqueous tripotassium phosphate solution (2.0 mol/L; 186 mL) were introduced in this order, and nitrogen bubbling was then conducted at 60° C. for 30 minutes. Thereto was added Pd(PPh$_3$)$_4$ (3.82 g). Thereafter, the mixture was stirred for 3.5 hours with heating and refluxing. After the mixture was returned to room temperature, distilled water was added thereto. The resultant mixture was extracted with toluene. The organic layer was washed with saturated aqueous sodium chloride solution and dried with magnesium sulfate, and the solvent was then distilled off under reduced pressure. The residue was subjected to silica gel column chromatography, thereby obtaining intermediate 15 (31.0 g; yield, 60%). The 3-bromophenylboronic acid was a product of Tokyo Kasei Kogyo Co., Ltd.

Synthesis of Intermediate 17

[Chem. 28]

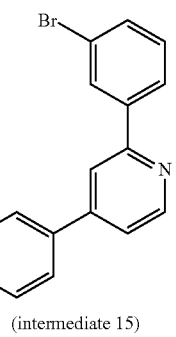

(intermediate 15)

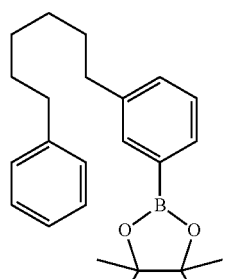

(intermediate 16)

Pd(PPh$_3$)$_4$
K$_3$PO$_4$aq
PhMe/EtOH

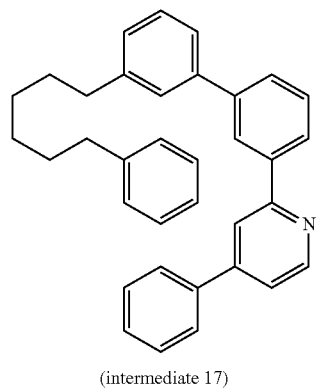

(intermediate 17)

Intermediate 15 (25.5 g), intermediate 16 (32.9 g), toluene (127 mL), ethanol (102 mL), and an aqueous tripotassium phosphate solution (2.0 mol/L; 102 mL) were introduced in this order, and nitrogen bubbling was then conducted at 60° C. for 30 minutes. Thereto was added Pd(PPh$_3$)$_4$ (1.89 g). Thereafter, the mixture was stirred for 3 hours with heating and refluxing. After the mixture was returned to room temperature, distilled water was added thereto. The resultant mixture was extracted with toluene. The organic layer was washed with saturated aqueous sodium chloride solution and dried with magnesium sulfate, and the solvent was then distilled off under reduced pressure. The residue was subjected to silica gel column chromatography, thereby obtaining intermediate 17 (21.7 g; yield, 56%). The intermediate 16 had been synthesized with reference to the method described in German Offenlegungschrift No. 102009023154.

Synthesis of Intermediate 18

[Chem. 29]

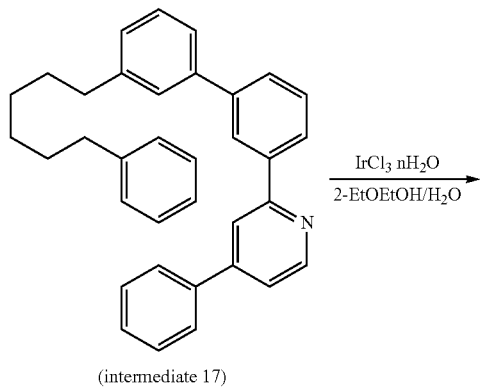

(intermediate 17)

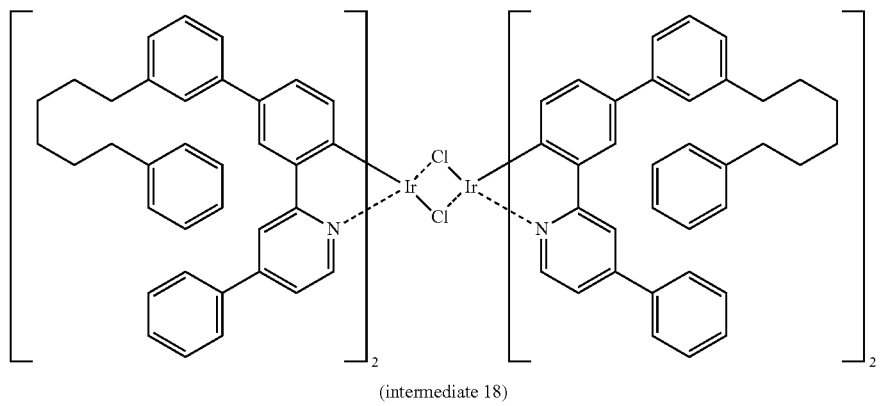

(intermediate 18)

Intermediate 17 (29.0 g; 62.0 mmol), IrCl$_3$.nH$_2$O (10.67 g; 29.5 mmol), 2-EtOEtOH (290 mL), and H$_2$O (85 mL) were introduced in this order, and nitrogen bubbling was conducted for 40 minutes. The mixture was heated at 140° C. for 20 hours and allowed to cool. Methanol was added to the liquid reaction mixture, and the resultant mixture was subjected to suction filtration. The filtration residue was washed with methanol and dried, thereby obtaining intermediate 18 (31.6 g; yield, 93%).

Synthesis of Comparative Compound D-4 duced, and the contents were heated with an oil bath of 180° C. Silver trifluoromethanesulfonate (0.41 g; 1.60 mol) was added thereto, and the mixture was stirred at 180° C. for 1.25 hours. This mixture was returned to room temperature and then subjected to column chromatography, thereby obtaining compound D-4 (361 mg; yield, 2%).

The results of a $^1$H-NMR examination of the compound obtained are shown below.

$^1$H-NMR (CDCl$_3$, ppm): 8.64 (d, 1H), 8.21 (d, 1H), 8.14-8.11 (m, 3H), 7.87 (d, 1H), 7.82-7.78 (m, 2H), 7.67-6.94 (m, 54H), 6.79-6.64 (m, 4H), 6.38 (d, 1H), 2.71-2.54 (m, 12H), 2.12 (s, 3H), 1.69-1.56 (m, 12H), 1.45-1.33 (m, 12H), 0.87 (s, 3H).

[Chem. 30]

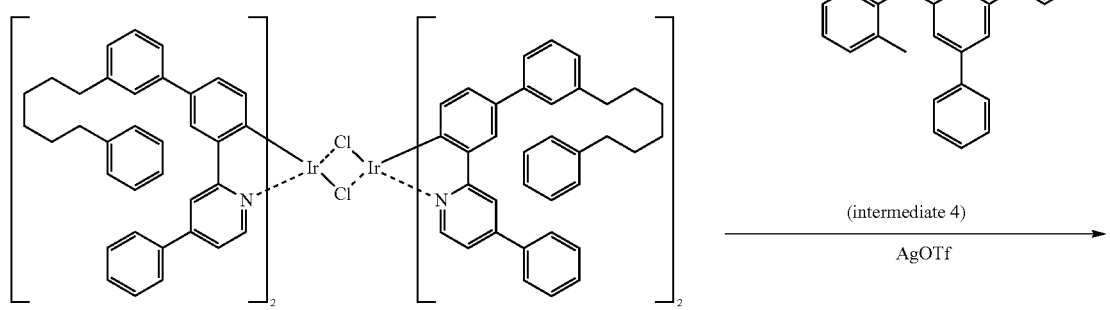

(intermediate 18)

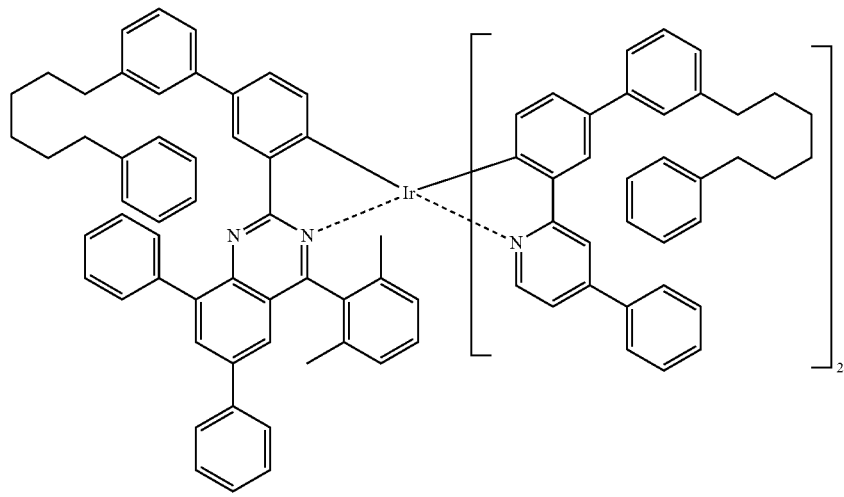

(compound D-4)

In a nitrogen atmosphere, intermediate 18 (10.8 g; 4.65 mmol) and intermediate 4 (32.6 g; 46.6 mmol) were intro- The ionization potential thereof determined by photoelectric emission spectroscopy was 5.34 eV.

Synthesis Example for Compound (D-5) of the Invention

Synthesis of Intermediate 19

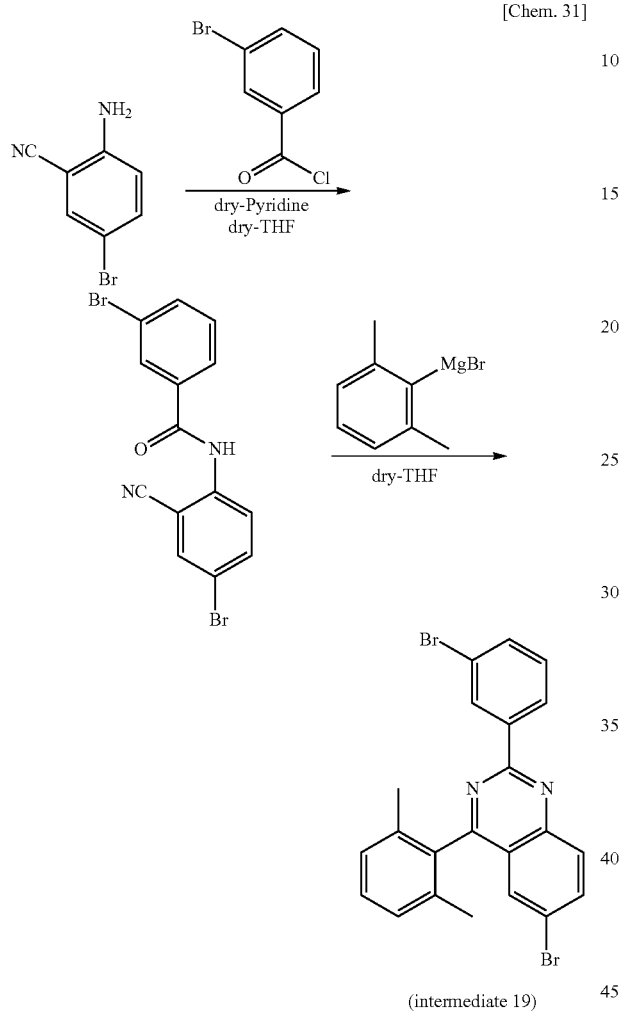

[Chem. 31]

(intermediate 19)

4-Bromo-2-cyanoaniline (22.5 g; 0.114 mol) and dehydrated pyridine (90 mL) were introduced. While the mixture was being cooled with an ice bath, a dehydrated-THF solution (10 mL) of 3-bromobenzoyl chloride (25 g; 0.114 mol) was gradually added dropwise thereto. The resultant mixture was stirred at room temperature for 3 hours. Methylene chloride and distilled water were added thereto, and the organic layer was washed with the distilled water. The solvent was distilled off under reduced pressure. Dehydrated THF (400 mL) was added to the residue. While this mixture was being cooled with an ice bath, a Grignard reagent prepared from 2-bromo-m-xylene (25.5 g; 0.138 mol), magnesium (3.2 g), and dehydrated THF (100 mL) was gradually added dropwise thereto. The mixture was stirred for 4 hours with heating and refluxing. After the mixture was returned to room temperature, saturated aqueous ammonium chloride solution was gradually added thereto while cooling the mixture with an ice bath. The solvent was distilled off under reduced pressure. Thereafter, methylene chloride was added, and the organic layer was washed with an aqueous ammonium chloride solution and dried with magnesium sulfate. The solvent was then distilled off under reduced pressure. The residue was washed with methanol and then subjected to suspension washing with an ethyl acetate/ethanol mixed solvent with heating, thereby obtaining intermediate 19 (15.6 g; yield 51%).

Synthesis of Intermediate 20

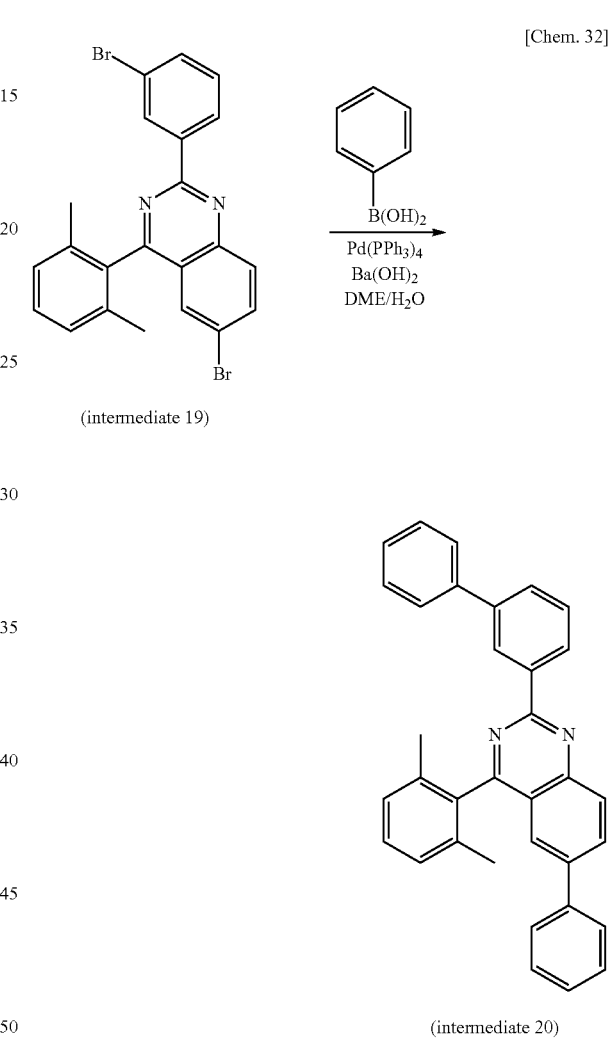

[Chem. 32]

(intermediate 20)

Intermediate 19 (15.6 g; 33.2 mmol), phenylboronic acid (12.2 g; 99.7 mmol), dimethoxyethane (160 mL), and water (90 mL) were introduced in this order, and nitrogen bubbling was then conducted for 90 minutes. Thereto were added Pd(PPh$_3$)$_4$ (1.15 g) and barium hydroxide octahydrate (42.0 g) in this order. Thereafter, the mixture was stirred for 7 hours with heating and refluxing. The resultant mixture was returned to room temperature and then subjected to suction filtration. Distilled water was added to the filtrate, and this mixture was extracted with methylene chloride. The organic layer was washed with water and dried with magnesium sulfate. Thereafter, the solvent was distilled off under reduced pressure. The residue was subjected to silica gel column chromatography, thereby obtaining intermediate 20 (11.8 g; yield 77%).

Synthesis of Compound D-5

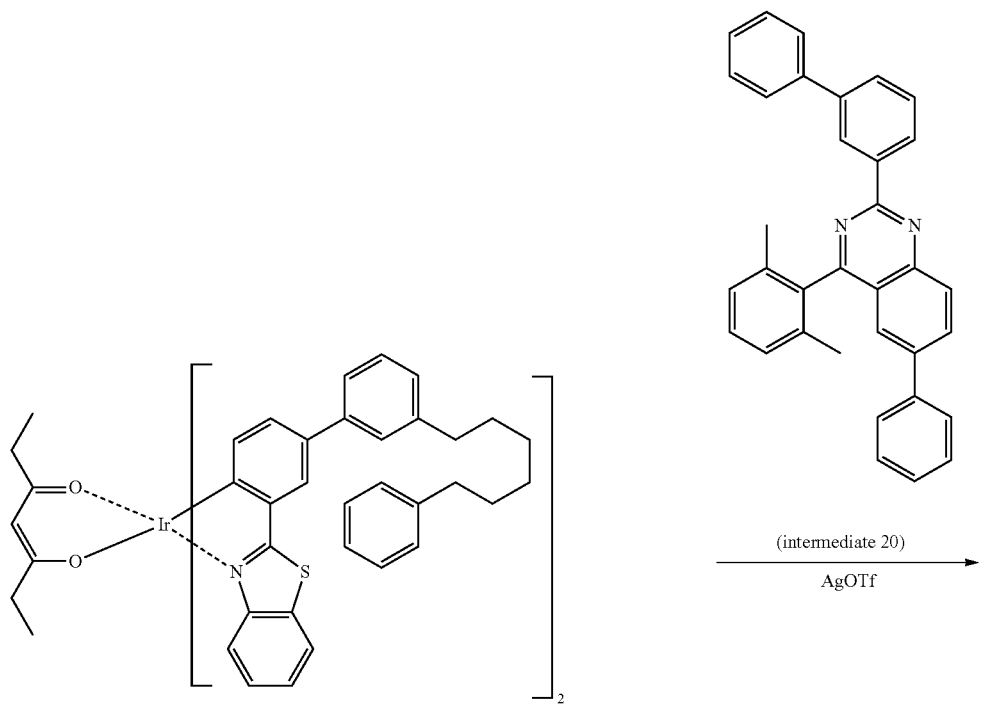

(intermediate 21)

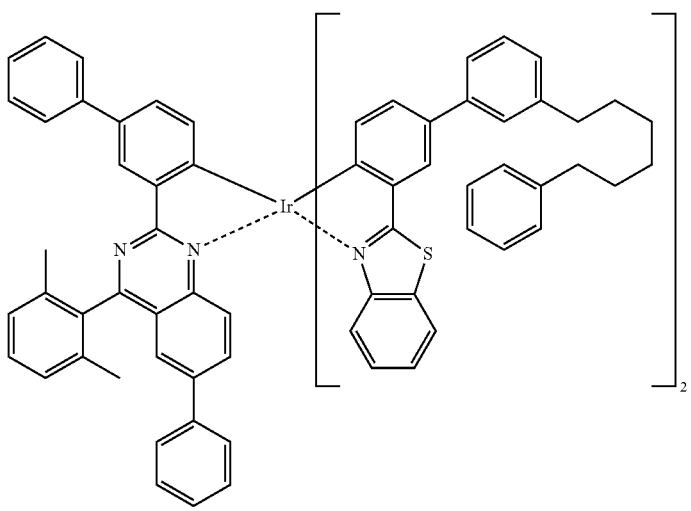

(compound D-5)

In a nitrogen atmosphere, intermediate 21 (8.15 g) and intermediate 20 (12.4 g) were introduced, and the contents were heated with an oil bath of 200° C. Silver trifluoromethanesulfonate (2.94 g) was added thereto, and the mixture was stirred at 200° C. for 45 mixtures. This mixture was returned to room temperature and then subjected to column chromatography, thereby obtaining compound D-5 (1.24 g; yield, 12%). The intermediate 21 had been synthesized by the same method as the synthesis of intermediate 13, except that the Na(acac) for synthesizing the intermediate 13 had been replaced with heptanedione and sodium carbonate.

The results of a $^1$H-NMR examination of the compound obtained are shown below.

$^1$H-NMR (CDCl$_3$, ppm): 8.64 (d, 1H), 7.90 (d, 1H), 7.87-7.81 (m, 4H), 7.66-7.64 (m, 2H), 7.57 (d, 1H), 7.41-7.06 (m, 35H), 6.99-6.95 (m, 1H), 6.88-6.74 (m, 6H), 2.65-2.56 (m, 8H), 2.16 (s, 3H), 2.01 (s, 3H), 1.63-1.58 (m, 8H), 1.38-1.36 (m, 8H).

Synthesis Example for Comparative Compound (D-6)

Synthesis of Comparative Compound D-6

[Chem. 34]

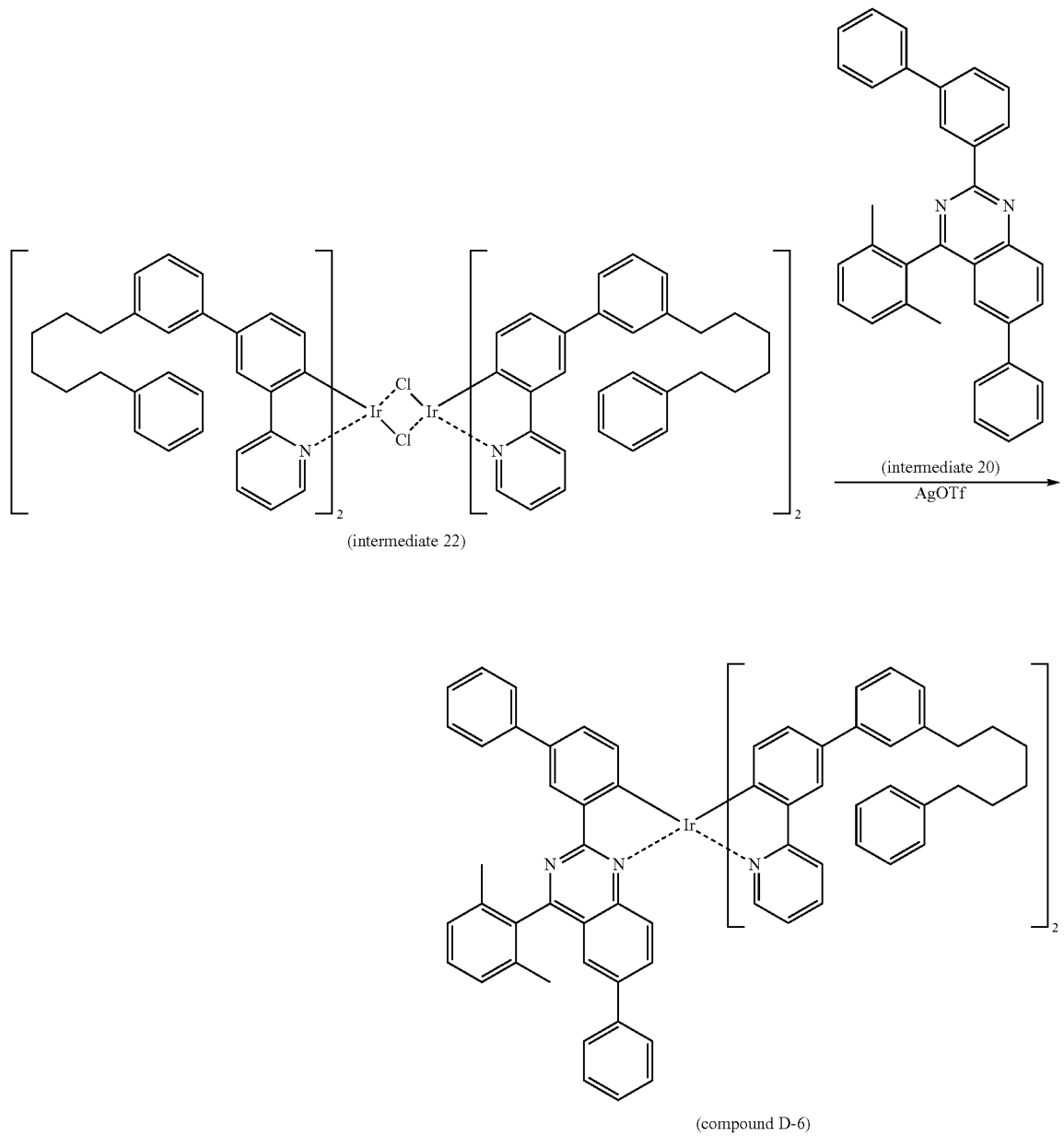

(compound D-6)

In a nitrogen atmosphere, intermediate 22 (2.11 g) and intermediate 20 (3.87 g) were introduced, and the contents were heated with an oil bath of 190° C. Silver trifluoromethanesulfonate (0.91 g) was added thereto, and the mixture was stirred at 200° C. for 1 hour. This mixture was returned to room temperature and then dissolved in methylene chloride. The solution was subjected to suction filtration. The filtrate was concentrated, and the residue was repeatedly subjected to column chromatography, thereby obtaining compound D-6 (46 mg; yield, 2%). The intermediate 22 had been synthesized by the same method as that for synthesizing intermediate 18, using a ligand synthesized by the method described in International Publication WO 2013/105615.

The results of a $^1$H-NMR examination of the compound obtained are shown below.

$^1$H-NMR (CDCl$_3$, ppm): 8.66 (d, 1H), 8.04 (m, 2H), 7.90 (m, 2H), 7.84 (m, 1H), 7.77 (m, 1H), 7.69-6.82 (m, 44H), 2.66-2.56 (m, 8H), 2.14 (s, 3H), 1.96 (s, 3H), 1.70-1.56 (m, 8H), 1.40-1.32 (m, 8H).

Synthesis Example for Compound (D-7) of the Invention

Synthesis of Compound D-7

[Chem. 35]

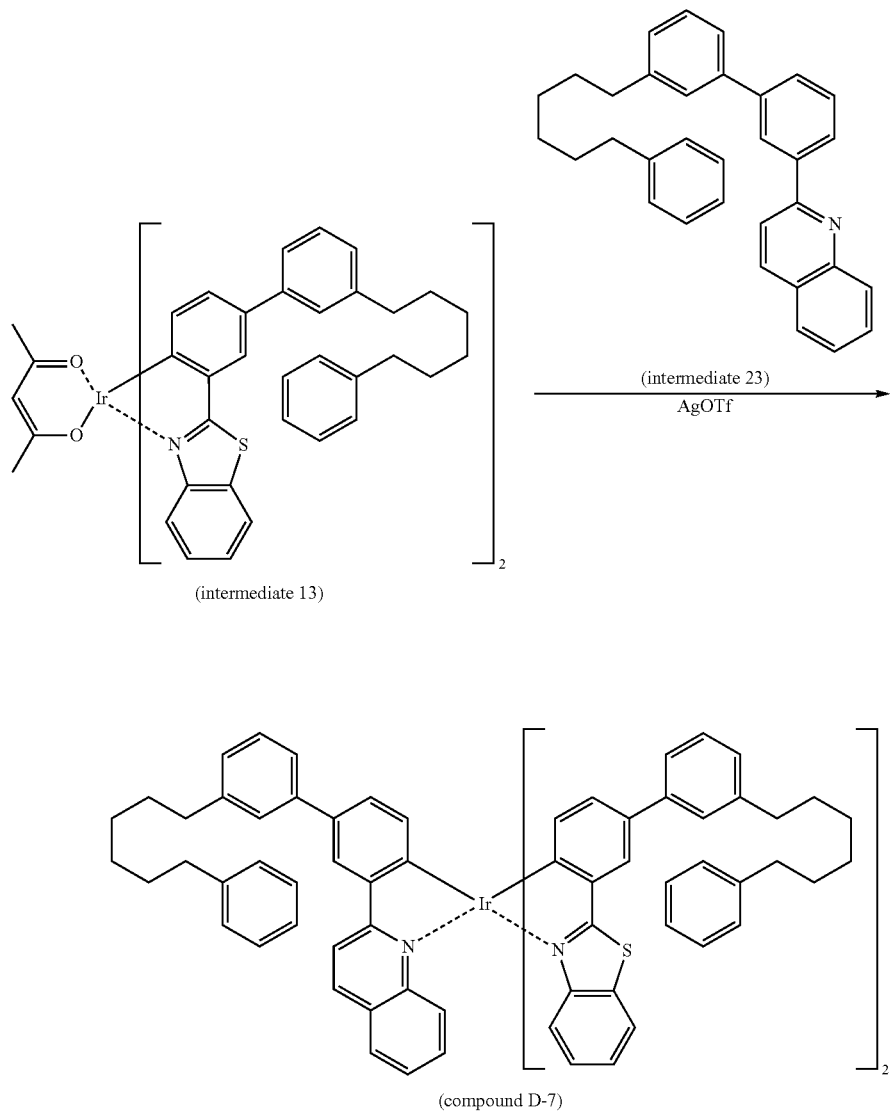

In a nitrogen atmosphere, intermediate 13 (2.58 g), intermediate 23 (1.16 g), and diglyme (20 mL) were introduced, and the contents were heated with an oil bath of 140° C. Silver trifluoromethanesulfonate (0.95 g) was added thereto, and the mixture was stirred at 170° C. for 70 minutes. After this mixture was returned to room temperature, methylene chloride was added thereto. This mixture was concentrated. The residue was subjected to column chromatography, thereby obtaining compound D-7 (6 mg; yield, <1%). The intermediate 23 had been synthesized with reference to the method described in International Publication WO 2013/105615.

The results of a $^1$H-NMR examination of the compound obtained are shown below.

$^1$H-NMR (CDCl$_3$, ppm): 8.27 (d, 1H), 8.14 (d, 1H), 8.10-8.07 (m, 2H), 7.87-7.77 (m, 4H), 7.73-7.71 (m, 1H), 7.46-6.96 (m, 34H), 6.82-6.64 (m, 7H), 2.66-2.55 (m, 12H), 1.68-1.56 (m, 12H), 1.40-1.32 (m, 12H).

Synthesis Example for Comparative Compound (D-8)

Synthesis of Comparative Compound D-8

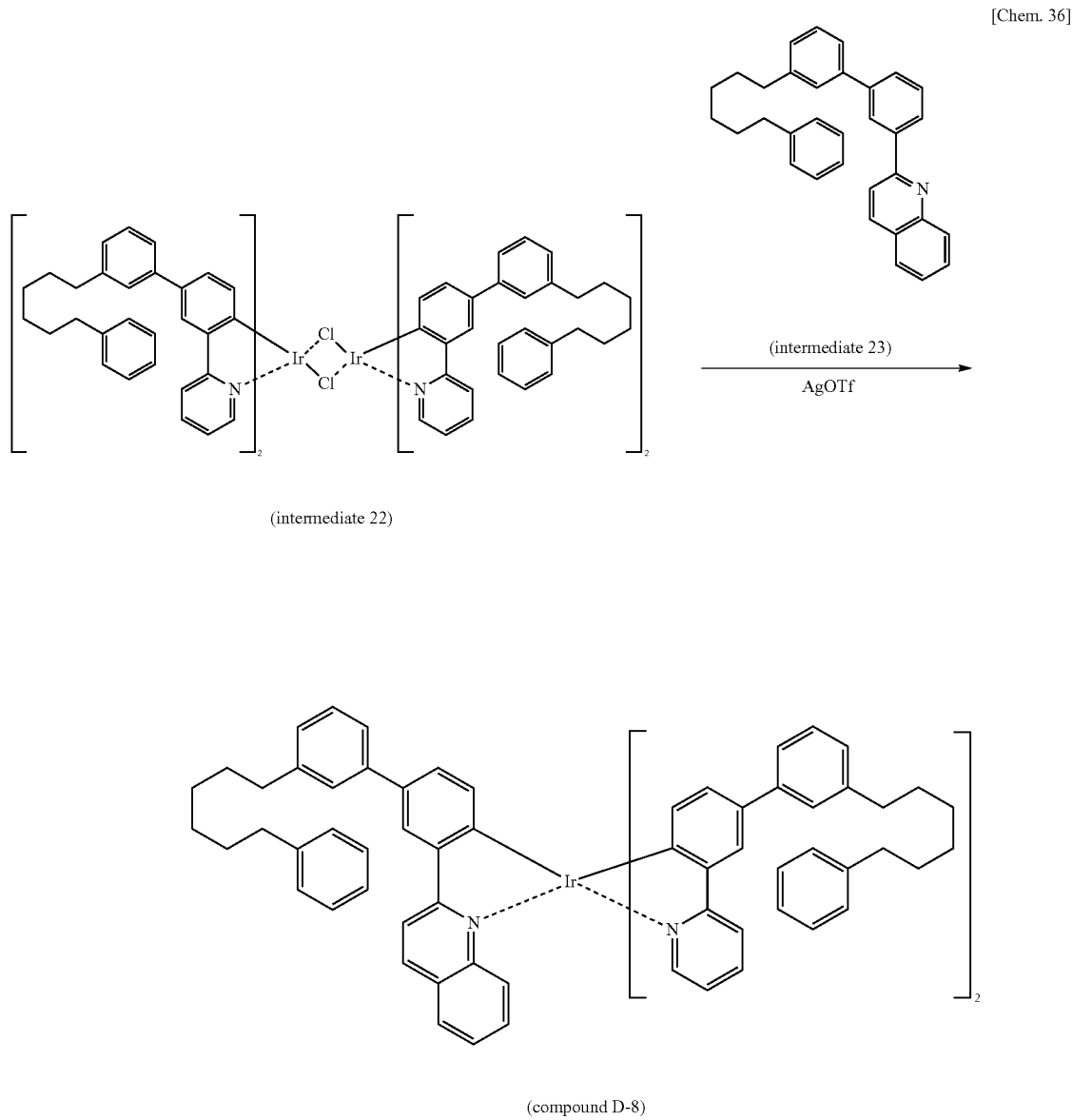

(intermediate 22)

(intermediate 23)

(compound D-8)

In a nitrogen atmosphere, intermediate 22 (2.85 g), intermediate 23 (3.75 g), and diglyme (2 mL) were introduced, and the mixture was heated with an oil bath of 140° C. Silver trifluoromethanesulfonate (1.24 g) was added thereto, and the mixture was stirred at 170° C. for 70 minutes. This mixture was returned to room temperature and then dissolved in methylene chloride. The solution was subjected to suction filtration. The filtrate was concentrated, and the residue was repeatedly subjected to column chromatography, thereby obtaining compound D-8 (0.15 g; yield, 4%).

The results of a $^1$H-NMR examination of the compound obtained are shown below.

$^1$H-NMR (CDCl$_3$, ppm): 8.26 (d, 1H), 8.13-8.07 (m, 2H), 8.02-7.96 (m, 2H), 7.88 (d, 1H), 7.83 (d, 1H), 7.75-7.69 (m, 4H), 7.61-7.56 (m, 2H), 7.49-7.21 (m, 16H), 7.16-6.90 (m, 18H), 6.78-6.74 (m, 3H), 2.67-2.56 (m, 12H), 1.70-1.55 (m, 12H), 1.41-1.32 (m, 12H).

Synthesis Example for Compound (D-9) of the Invention

Synthesis of Compound D-9

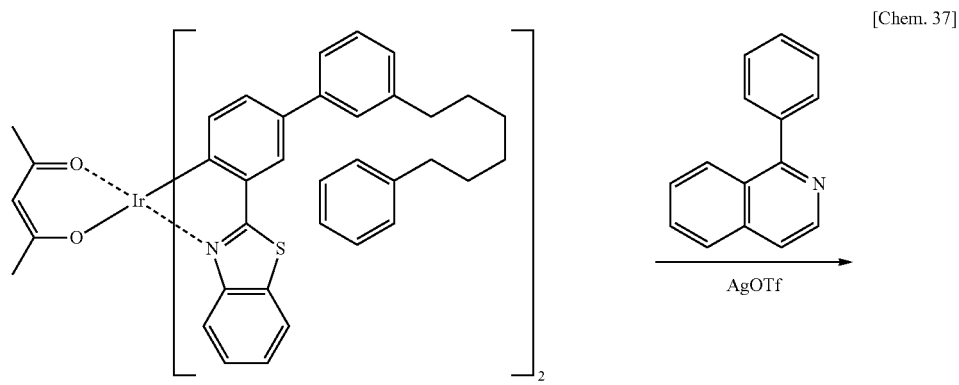

(intermediate 13)

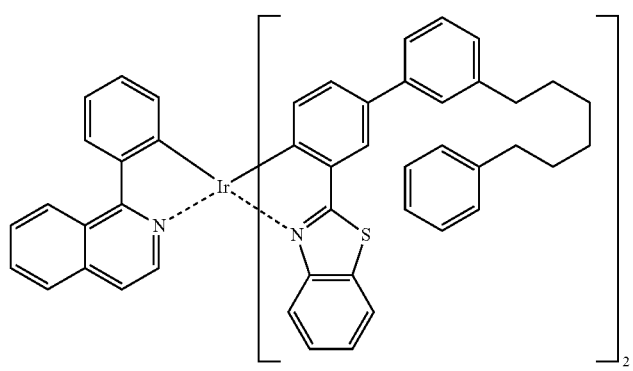

(compound D-9)

In a nitrogen atmosphere, intermediate 13 (3.0 g), 1-phenylisoquinoline (0.64 g), and diglyme (10 mL) were introduced, and the contents were heated with an oil bath of 140° C. Silver trifluoromethanesulfonate (1.0 g) was added thereto, and the mixture was stirred at 140° C. for 2 hours. After the mixture was returned to room temperature, methylene chloride was added thereto. This mixture was concentrated. The residue was subjected to column chromatography, thereby obtaining compound D-9 (0.23 g; yield, 7%). The 1-phenylisoquinoline had been purchased from Tokyo Kasei Kogyo.

The results of a $^1$H-NMR examination of the compound obtained are shown below.

$^1$H-NMR (CDCl$_3$, ppm): 8.90 (m, 1H), 8.15 (d, 1H), 7.92-7.76 (m, 6H), 7.67-7.61 (m, 2H), 7.41-7.39 (m, 4H), 7.31-6.70 (m, 27H), 6.33 (d, 1H), 2.65-2.56 (m, 8H), 1.65-1.52 (m, 8H), 1.37-1.35 (m, 8H).

Synthesis Example for Comparative Compound (D-10)

Synthesis of Comparative Compound D-10

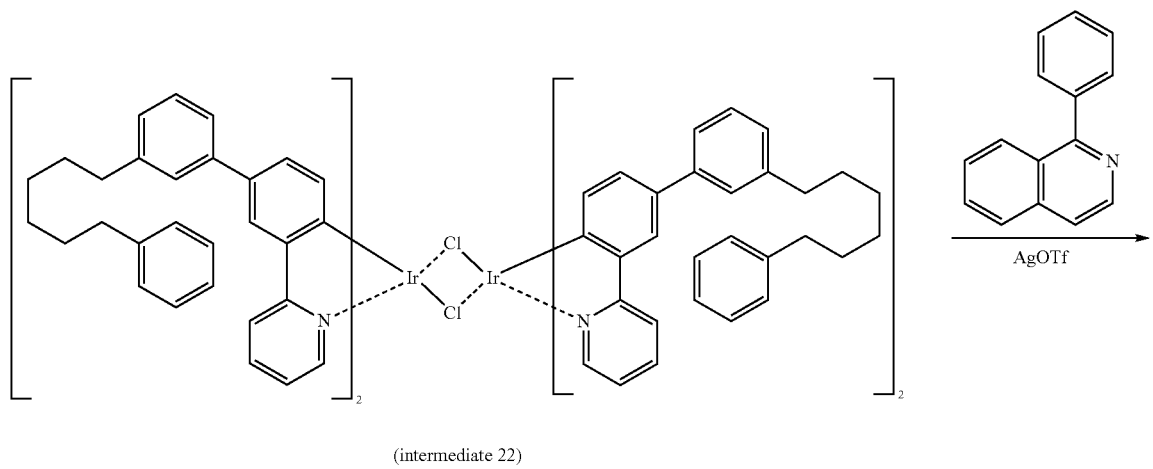

(intermediate 22)

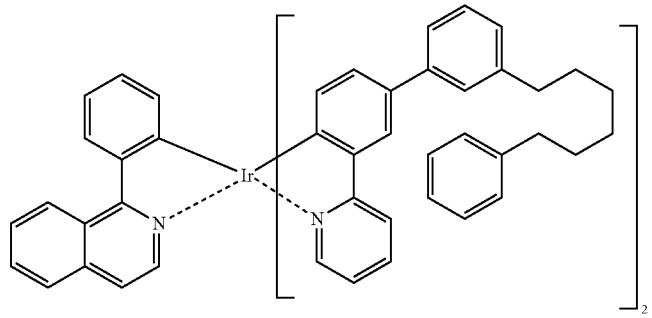

(compound D-10)

In a nitrogen atmosphere, intermediate 22 (3.43 g), 1-phenylisoquinoline (0.84 g), and diglyme (7 mL) were introduced, and the mixture was heated with an oil bath of 120° C. Silver trifluoromethanesulfonate (1.48 g) was added thereto, and the mixture was stirred at 120° C. for 60 minutes. This mixture was returned to room temperature and then dissolved in methylene chloride. The solution was subjected to suction filtration. The filtrate was concentrated, and the residue was repeatedly subjected to column chromatography, thereby obtaining compound D-10 (0.15 g; yield, 4%).

The results of a $^1$H-NMR examination of the compound obtained are shown below.

$^1$H-NMR (CDCl$_3$, ppm): 8.99-8.96 (m, 1H), 8.20 (d, 1H), 8.02-7.99 (m, 2H), 7.88 (m, 2H), 7.77-7.75 (m, 1H), 7.66-7.55 (m, 5H), 7.48-7.36 (m, 6H), 7.30-6.77 (m, 22H), 2.65-2.56 (m, 8H), 1.69-1.56 (m, 8H), 1.41-1.32 (m, 8H).

Evaluation of Luminescent Quantum Yield

Example 1

Iridium complex compound D-2, which is a compound of the invention, was dissolved in 2-methyltetrahydrofuran (dehydrated; containing no stabilizer) to prepare a solution having a concentration of 1×10$^{-5}$ mol/L. This solution was transferred to a quartz cell equipped with a Teflon cock. Thereafter, nitrogen bubbling was conducted for 15 minutes, and this solution was examined for luminescent quantum yield. The results thereof are shown in Table 1. The 2-methyltetrahydrofuran (dehydrated; containing no stabilizer) was a product of Sigma-Aldrich Corp.

<Measurement of Luminescent Quantum Yield>

Apparatus: organic EL quantum yield measuring apparatus C9920-02; Hamamatsu Photonics K.K.

(Light source: monochromatic light source L9799-01)
(Detector: multi-channel detector PMA-11)
Excitation light: 380 nm Example 2 and Comparative Example 1

2-Methyltetrahydrofuran solutions were prepared in the same manner as in Example 1, except that compound D-3 or compound D-4 was used in place of the compound D-2. These solutions were subjected to the measurement of absolute quantum yield in the same manner. The results of these measurements are summarized in Table 1. Compound D-4 is outside the scope of the invention because this compound has no ligand represented by L$^2$ in formula (1).

[Chem. 39]
<Compounds of the Invention>
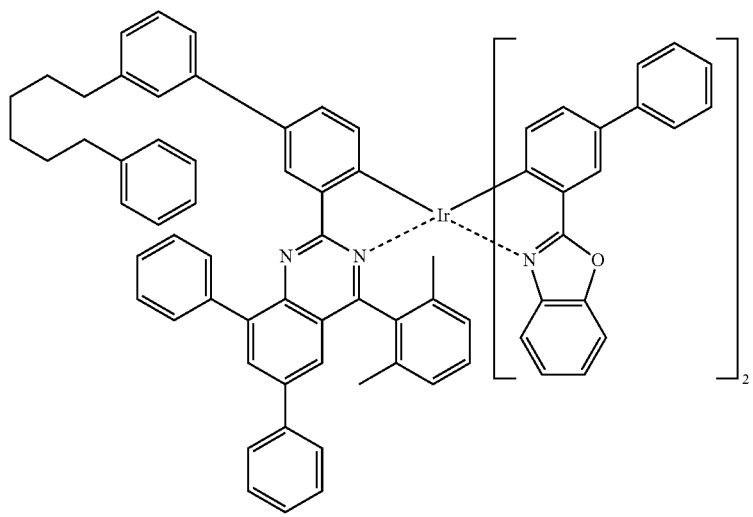
(compound D-2)
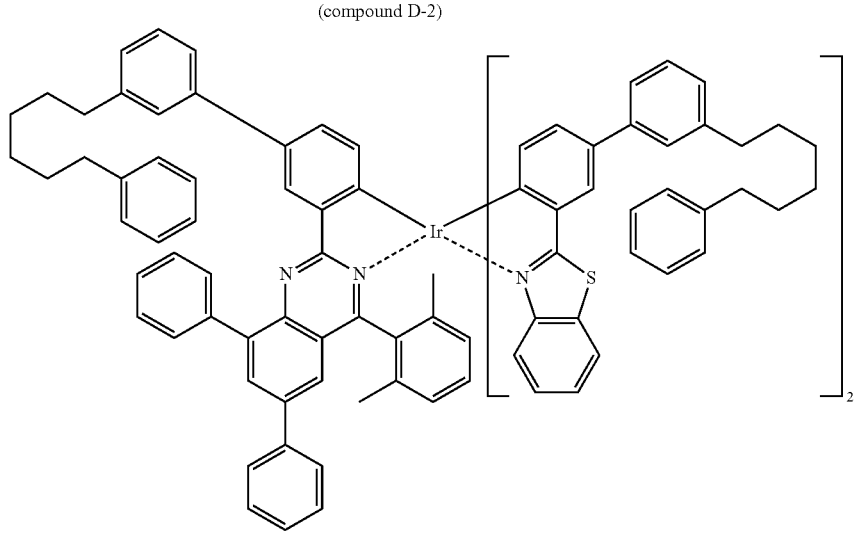
(compound D-3)
<Comparative Compound>
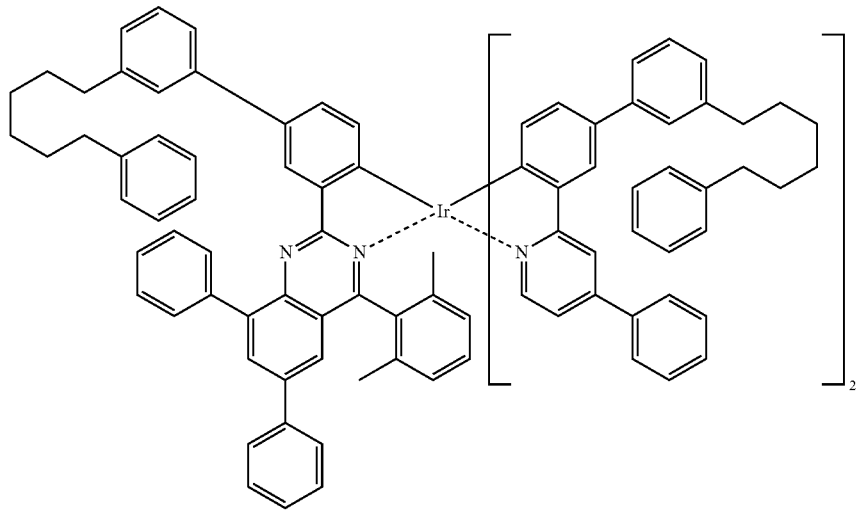
(compound D-4)

TABLE 1

| | Compound | Ionization potential (eV) | Luminescent quantum yield (Comparative Example 1 being taken as 1) | Color of luminescence |
|---|---|---|---|---|
| Example 1 | D-2 | 5.47 | 1.65 | red |
| Example 2 | D-3 | 5.41 | 1.59 | red |
| Comparative Example 1 | D-4 | 5.34 | 1 | red |

It was understood from Table 1 that the iridium complex compounds of the invention emit red light with a satisfactory quantum yield. Furthermore, it is presumed that since the iridium complex compounds of the invention each had a large value of ionization potential, the luminescent quantum yield thereof had increased accordingly. It is thought that a main cause which brought about the increased ionization potential of the iridium complex compounds of the invention is the highly electron-withdrawing nature of the ligand $L^2$ in formula (1).

Example 3 and Comparative Example 2

2-Methyltetrahydrofuran solutions were prepared in the same manner as in Example 1, except that compound D-5 and compound D-6 were used in place of the compound D-2. These solutions were subjected to the measurement of absolute quantum yield in the same manner. The results of these measurements are summarized in Table 2. Compound D-6 is outside the scope of the invention because this compound has no ligand represented by $L^2$ in formula (1).

[Chem. 40]

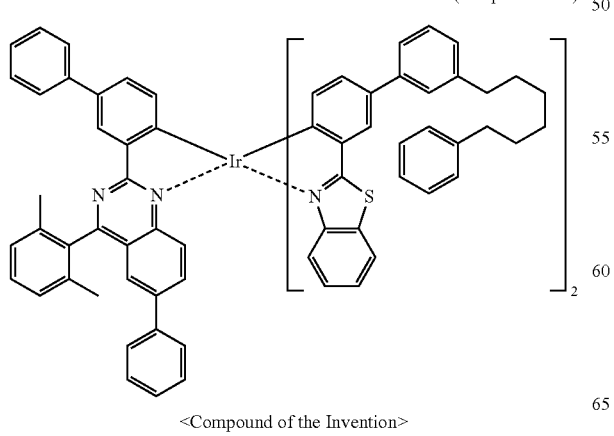

(compound D-5)

<Compound of the Invention>

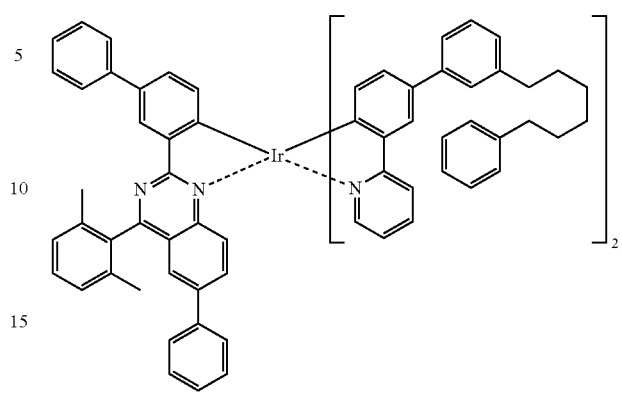

(compound D-6)

<Comparative Compound>

TABLE 2

| | Compound | Luminescent quantum yield (Comparative Example 2 being taken as 1) | Color of luminescence |
|---|---|---|---|
| Example 3 | D-5 | 3.75 | red |
| Comparative Example 2 | D-6 | 1 | red |

Example 4 and Comparative Example 3

2-Methyltetrahydrofuran solutions were prepared in the same manner as in Example 1, except that compound D-7 and compound D-8 were used in place of the compound D-2. These solutions were subjected to the measurement of absolute quantum yield in the same manner. The results of these measurements are summarized in Table 3. Compound D-8 is outside the scope of the invention because this compound has no ligand represented by $L^2$ in formula (1).

[Chem. 41]

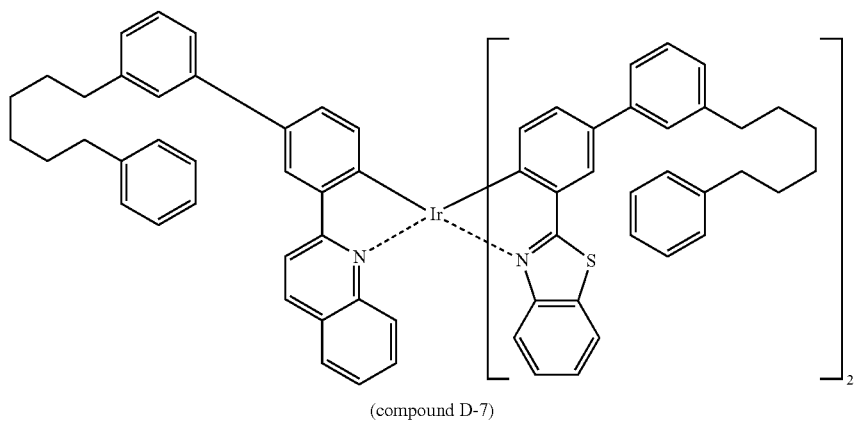

(compound D-7)

<Compound of the Invention>

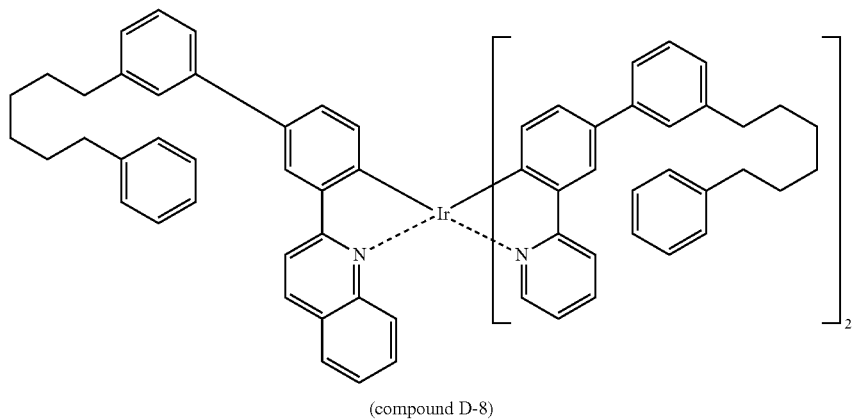

(compound D-8)

<Comparitive Compound>

TABLE 3

| Compound | | Luminescent quantum yield (Comparative Example 3 being taken as 1) | Color of luminescence |
| --- | --- | --- | --- |
| Example 4 | D-7 | 1.45 | red |
| Comparative Example 3 | D-8 | 1 | red |

Example 5 and Comparative Example 4

2-Methyltetrahydrofuran solutions were prepared in the same manner as in Example 1, except that compound D-9 and compound D-10 were used in place of the compound D-2. These solutions were subjected to the measurement of absolute quantum yield in the same manner. The results of these measurements are summarized in Table 4. Compound D-10 is outside the scope of the invention because this compound has no ligand represented by $L^2$ in formula (1).

[Chem. 42]

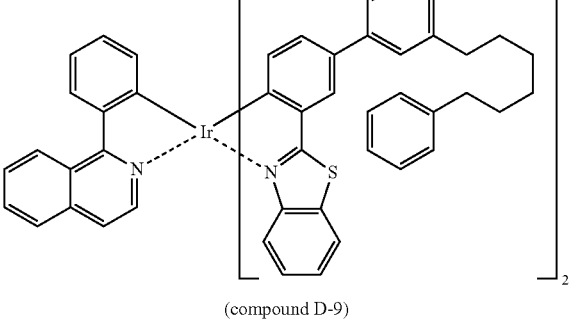

(compound D-9)

<Compound of the Invention>

<Comparative Compound>

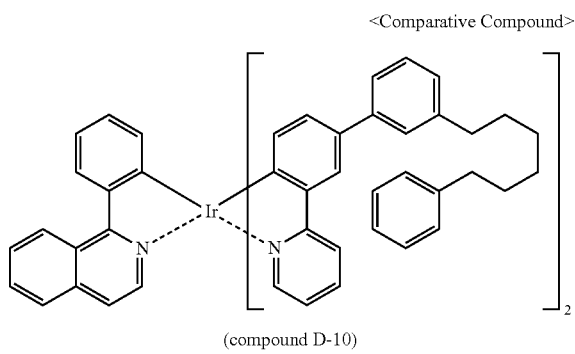

(compound D-10)

TABLE 4

| Compound | | Luminescent quantum yield (Comparative Example 4 being taken as 1) | Color of luminescence |
| --- | --- | --- | --- |
| Example 5 | D-9 | 1.20 | red |
| Comparative Example 4 | D-10 | 1 | red |

It was understood from Table 2 to Table 4 that the iridium complex compounds of the invention emit red light with a satisfactory quantum yield even when these compounds differ in the structure of ligand $L^1$ in formula (1).

Example 6

Production of Organic Electroluminescent Element

An organic electroluminescent element having the structure shown in The FIGURE was produced by the following method.

A substrate constituted of a glass substrate 1 and, formed thereon, a transparent conductive film of iridium-tin oxide (ITO) deposited in a thickness of 70 nm (sputtering-coated product; sheet resistance, 15Ω) was subjected to patterning into stripes having a width of 2 mm using an ordinary technique of photolithography and etching with hydrochloric acid. Thus, an anode was formed. The ITO substrate which had undergone the patterning was cleaned by subjecting the substrate to ultrasonic cleaning with a neutral detergent and rinsing with ultrapure water, subsequently dried by nitrogen blowing, and finally subjected to ultraviolet/ozone cleaning.

Subsequently, a hole injection layer was formed by a wet-process film formation method in the following manner. The polymer compound of the following formula (PB-1) (weight-average molecular weight, 40,000; number-average molecular weight, 29,000), which had aromatic amino groups, and the electron-accepting compound (A-1) of the structural formula shown below were used as materials for the hole injection layer, and spin coating was conducted under the following conditions to form an even thin film having a thickness of 40 nm.

The polymer compound PB-1 had been synthesized with reference to the method disclosed in International Publication WO 2009/102027.

The numerals in the following structural formula PB-1 indicate the ratio between the two kinds of repeating units within the respective [ ]s. Ar in structural formula PB-1 represents the aryl group shown on the right-hand side of the structural formula.

[Chem. 43]

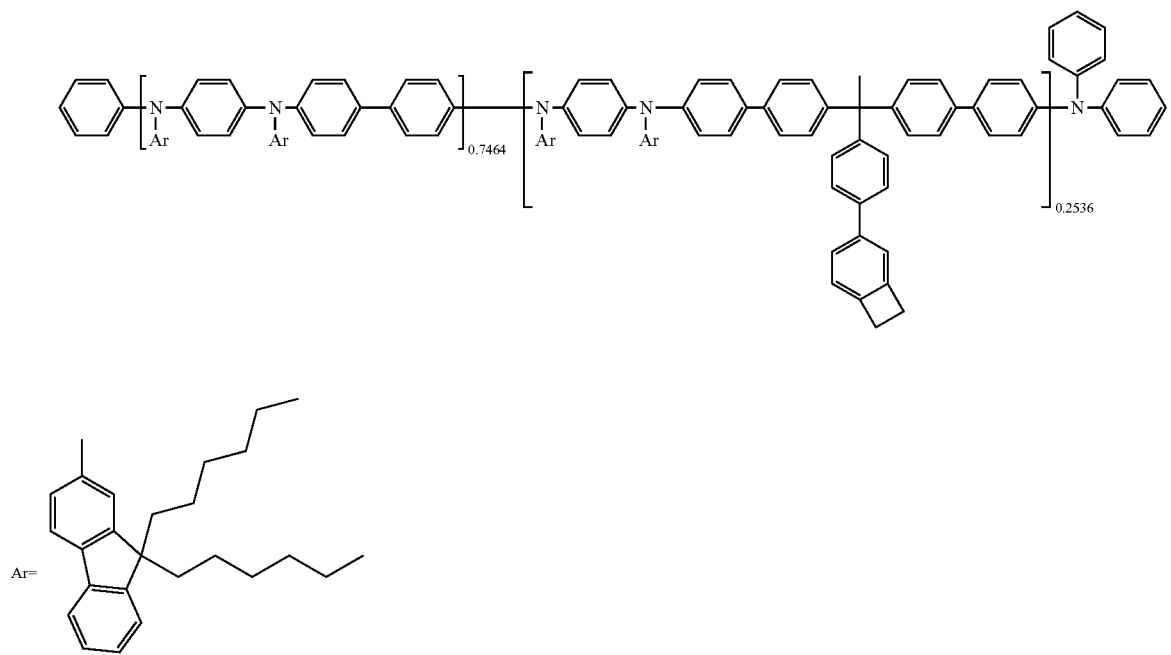

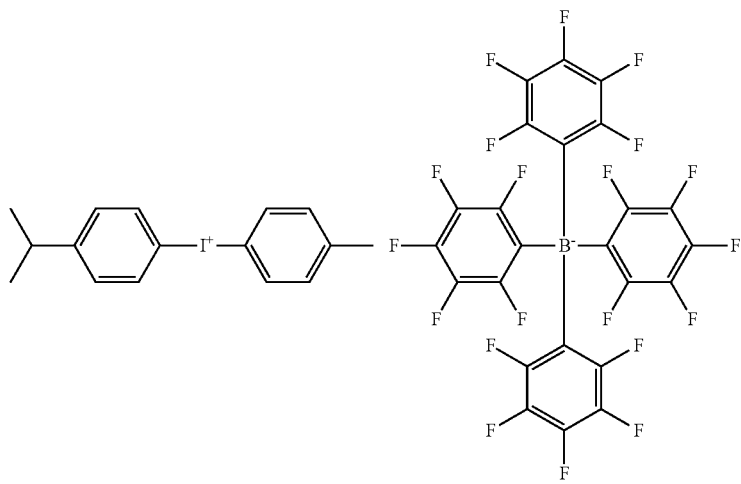

(A-1)

<Composition for Hole Injection Layer Formation>
(Solvent) ethyl benzoate
(Concentrations in coating fluid)
PB-1: 2.0% by weight
A-1: 0.50% by weight
<Conditions for Film Formation>
(Spin coating atmosphere) in the air, 23° C.
(Drying conditions) 240° C.×60 min Subsequently, a hole transport layer was formed by a wet-process film formation method in the following manner. A composition for organic electroluminescent elements was prepared using the polymer compound having aromatic amino groups which was represented by the following structural formula (weight-average molecular weight, 79,000; number-average molecular weight, 54,000), i.e., charge transport material (PB-2), as a material for the hole transport layer and using phenylcyclohexane as a solvent. This composition for organic electroluminescent elements was used and applied by spin coating under the following conditions to obtain a thin film having a thickness of 20 nm.

Ar in the structural formula PB-2 represents the two kinds of aryl groups shown on the right-hand side of the structural formula, and the two kinds of aryl groups are present in the molar ratio indicated by the numerals. The polymer compound PB-2 had been synthesized with reference to the method discloses in International Publication WO 2011/099531.

[Chem. 44]

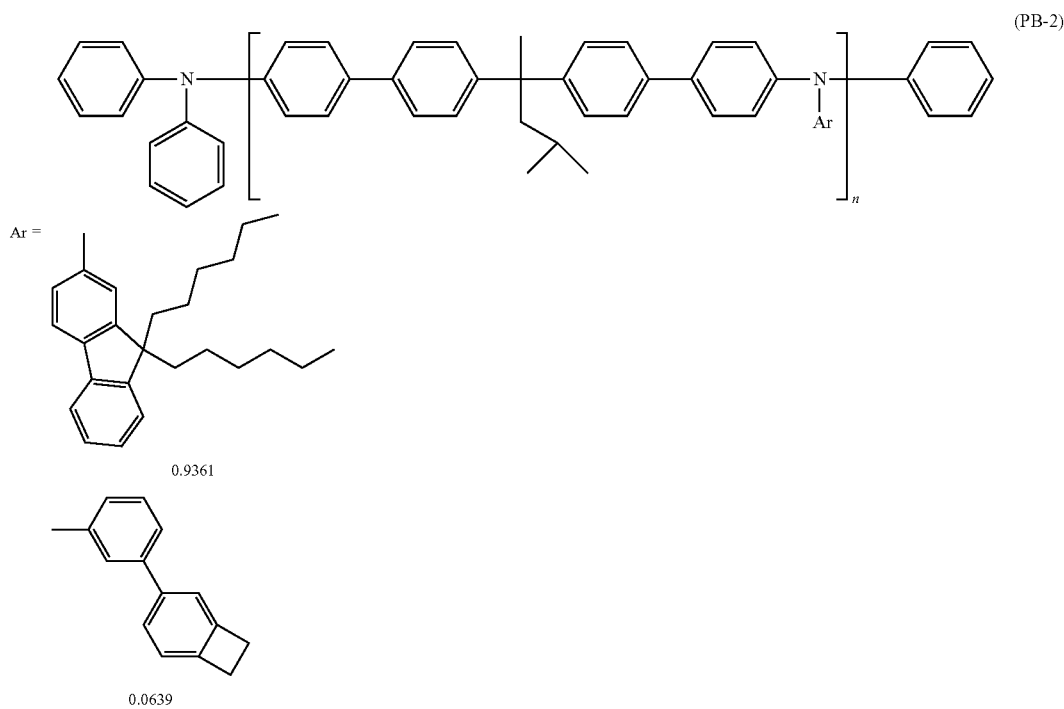

(PB-2)

<Composition for Hole Transport Layer Formation>
  (Solvent) phenylcyclohexane
  (Concentration in coating fluid)
  PB-2: 1.5% by weight
<Conditions for Film Formation>
  (Spin coating atmosphere) in dry nitrogen
  (Drying conditions) 230° C.×60 min (in dry nitrogen)

Next, in preparation for luminescent-layer formation, the iridium-complex-compound-containing composition shown below was prepared using the organic compound (HO-1) to organic compound (HO-3) shown below as charge transport materials and further using the iridium complex compound (D-A1) shown below and the iridium complex compound (D-2) of the invention as luminescent materials. This composition was applied on the hole transport layer by spin coating under the following conditions to obtain a emission layer having a thickness of 50 nm.

[Chem. 45]

(HO-1)

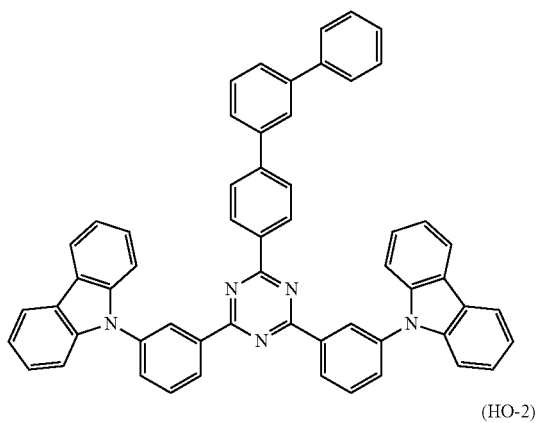

(HO-2)

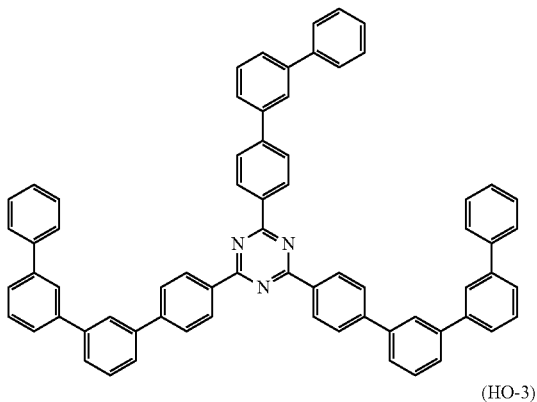

(HO-3)

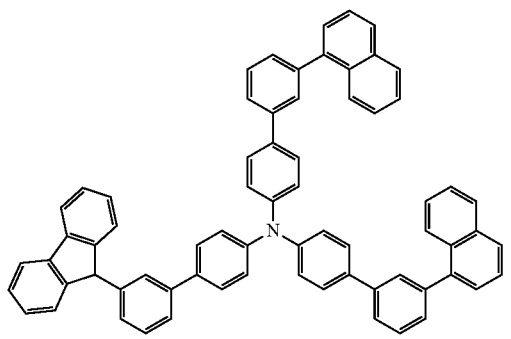

(D-A1)

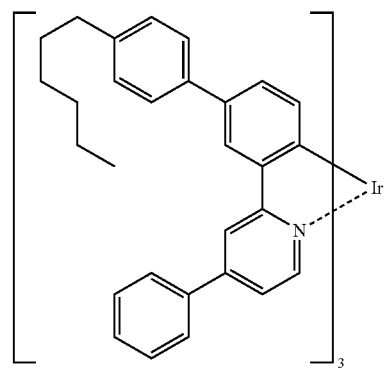

<Composition for Luminescent-Layer Formation>
  (Solvent) phenylcyclohexane
  (Concentrations in coating fluid)
  HO-1: 0.625% by weight
  HO-2: 0.625% by weight
  HO-3: 3.75% by weight
  D-A1: 0.50% by weight
  D-2: 0.50% by weight
<Conditions for Spin Coating>
  (Spin coating atmosphere) in dry nitrogen
  (Drying conditions) 120° C.×20 min (in dry nitrogen)

This substrate was temporarily taken out in the air and rapidly disposed in the chamber of a vacuum deposition apparatus. The chamber was roughed with a rotary pump and then depressurized with a cryopump. A mask for deposition was disposed on a given region of the substrate, and separate porcelain crucibles respectively containing the necessary deposition materials had been disposed beforehand in the chamber.

Next, a layer of the compound (HB-1) shown below was superposed in a thickness of 15 nm as a hole blocking layer.

[Chem. 46]

(HB-1)

Next, the 8-hydroxyquinoline aluminum complex (ET-1) shown below was vapor-deposited as an electron transport layer on the hole blocking layer in the same manner, the thickness of the electron transport layer being 20 nm.

[Chem. 47]

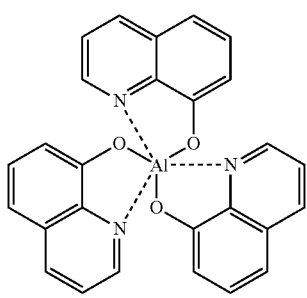

ET-1

During the vacuum deposition of the hole blocking layer and electron transport layer, the temperature of the substrate was kept at room temperature.

Here, the element in which up to the deposition of the electron transport layer had been conducted was temporarily taken out of the vacuum deposition apparatus, and a shadow-mask in the form of stripes with a width of 2 mm was brought, as a mask for cathode deposition, into close contact with the element in the air so that these stripes were perpendicular to the ITO stripes of the anode. This mask-covered element was disposed in another vacuum deposition apparatus, which was evacuated until the degree of vacuum within the apparatus became at least $3.3\times10^{-4}$ Pa in the same manner as for the organic layer.

Next, lithium fluoride (LiF) was deposited as an electron injection layer on the electron transport layer so as to result in a film thickness of 0.5 nm.

Subsequently, an aluminum layer having a thickness of 80 nm was formed as a cathode on the electron injection layer to complete the cathode. During the deposition of the electron injection layer and cathode, the temperature of the substrate was kept at room temperature.

Thus, an organic electroluminescent element which emitted red light and had a light-emitting area portion having a size of 2 mm×2 mm was obtained.

Example 7

An organic electroluminescent element was produced in the same manner as in Example 6, except that the compound D-2 used for luminescent-layer formation was replaced with compound D-3. Results concerning luminescent efficiency at 1,000 cd/m² are summarized in Table 5. The time period required for the element operated at an initial luminance of 5,000 cd/m² to decrease in luminance to 95% of the initial luminance was measured. As a result, the time period was longer in the case of compound D-3 than the case of the compound D-2. Namely, compound D-3 had a longer life.

Comparative Example 5

An organic electroluminescent element was produced in the same manner as in Example 6, except that the compound D-2 used for luminescent-layer formation was replaced with compound D-4. Results concerning luminescent efficiency at 1,000 cd/m² are summarized in Table 5. As stated hereinabove, compound D-4 is outside the scope of the present invention because this compound has no ligand represented by $L^2$ in formula (1).

TABLE 5

| | Compound | Current efficiency during luminescence at 1,000 cd/m² (Comparative Example 5 being taken as 1) | Color of luminescence |
|---|---|---|---|
| Example 6 | D-2 | 2.11 | red |
| Example 7 | D-3 | 1.65 | red |
| Comparative Example 5 | D-4 | 1 | red |

As apparent from Table 5, the organic electroluminescent elements employing the compounds of the invention each have a high luminescent efficiency.

While the invention has been described in detail and with reference to specific embodiments thereof, it will be apparent to one skilled in the art that various changes and modifications can be made therein without departing from the spirit and scope thereof. This application is based on a Japanese patent application filed on Dec. 12, 2013 (Application No. 2013-257200), the contents thereof being incorporated herein by reference.

DESCRIPTION OF THE REFERENCE NUMERALS

1 Substrate
2 Anode
3 Hole injection layer
4 Hole transport layer
4 Emission layer
6 Hole blocking layer
7 Electron transport layer
8 Electron injection layer
9 Cathode
10 Organic electroluminescent element

The invention claimed is:

1. An iridium complex compound represented by the following formula (1):

wherein in formula (1):

Ir represents an iridium atom;

$L^1$ to $L^3$ each independently represent an organic ligand bonded to the Ir, and the $L^1$ is selected from the group consisting of ligands represented by any of the following formula (2-1) to formula (2-3) or is a ligand represented by any of formula (2-1) to formula (2-3) which includes a partial structure represented by the following formula (4) and the $L^2$ is a ligand represented by the following formula (3-1) or is a ligand represented by formula (3-1) which includes a partial structure represented by the following formula (4);

m and n each are an integer of 1 or 2, and m+n is 3 or less;

the $L^3$ is not a ligand represented by any of formulae (2-1) to (2-3) or by formula (3-1); and in the case where there are a plurality of moieties represented by any of $L^1$ to $L^3$, these moieties may be the same or different:

(2-1)

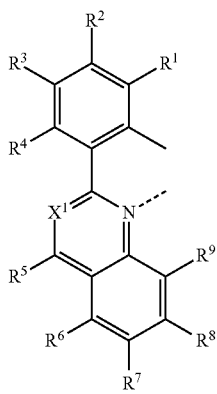

(2-2)

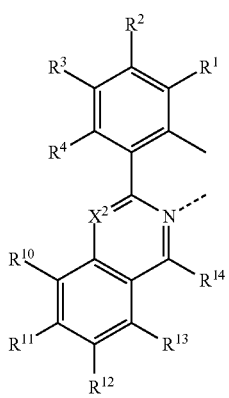

(2-3)

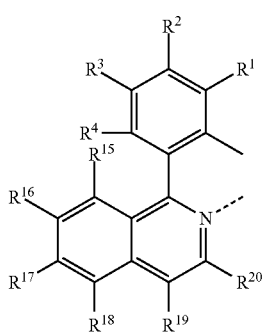

(3-1)

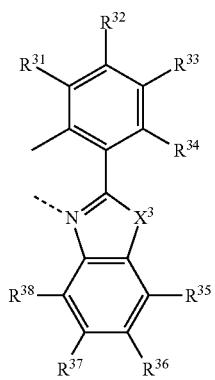

wherein
$X^1$ and $X^2$ each independently represent a nitrogen atom or C—$R^{21}$; and $R^1$ to $R^{21}$ and $R^{31}$ to $R^{38}$ each independently represent a hydrogen atom, an alkyl group having 1-20 carbon atoms, a (hetero)aralkyl group having 7-40 carbon atoms, an alkoxy group having 1-20 carbon atoms, a (hetero)aryloxy group having 3-20 carbon atoms, an alkylsilyl group in which each alkyl group has 1-20 carbon atoms, a (hetero)arylsilyl group in which each aryl group has 6-20 carbon atoms, an alkylcarbonyl group having 2-20 carbon atoms, an arylcarbonyl group having 7-20 carbon atoms, an alkylamino group having 1-20 carbon atoms, a (hetero)arylamino group having 6-20 carbon atoms, or a (hetero)aryl group having 3-30 carbon atoms, and these groups may further have substituents, $R^1$ to $R^4$ and $R^{31}$ to $R^{34}$ each may be bonded to any adjacent one of the $R^1$ to $R^4$ or of the $R^{31}$ to $R^{34}$ to form a ring, and the ring may further have one or more substituents, $X^3$ represents an oxygen atom, a sulfur atom, or N—$R^{39}$, and $R^{39}$ represents an alkyl group having 1-20 carbon atoms, a (hetero)aralkyl group having 7-40 carbon atoms, or a (hetero)aryl group having 3-20 carbon atoms;

wherein at least one of $L^1$ to $L^3$ in the formula (1) includes at least one partial structure represented by the following formula (4):

—Ar$^1$—Z     (4)

wherein Ar$1^1$ represents an arylene group having 6-20 carbon atoms, and Z represents an alkyl group having 5-20 carbon atoms, a (hetero)aralkyl group having 7-40 carbon atoms, an alkoxy group having 4-20 carbon atoms, a (hetero)aryloxy group having 3-20 carbon atoms, or a substituent represented by the following formula (4-1):

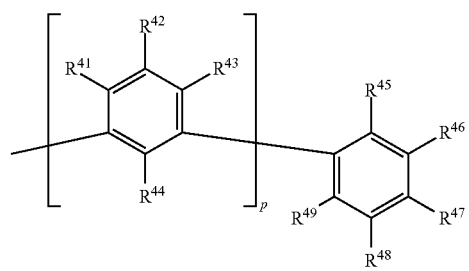

(4-1)

wherein $R^{41}$ to $R^{44}$ each independently represent a hydrogen atom, a fluorine atom, a chlorine atom, a bromine atom, an alkyl group having 1-20 carbon atoms, a (hetero)aralkyl group having 7-40 carbon atoms, an alkoxy group having 1-20 carbon atoms, a (hetero)aryloxy group having 3-20 carbon atoms, or a (hetero)aryl group having 3-20 carbon atoms; $R^{45}$ to $R^{49}$ each independently represent a hydrogen atom, a fluorine atom, a chlorine atom, a bromine atom, an alkyl group having 1-20 carbon atoms, a (hetero)aralkyl group having 7-40 carbon atoms, an alkoxy group having 1-20 carbon atoms, or a (hetero)aryloxy group having 3-20 carbon atoms; and p represents an integer of 1 to 4, and when p is 2 or larger, the multiple $R^{41}$ moieties to $R^{44}$ moieties each may be the same or different.

2. The iridium complex compound according to claim 1, wherein n in the formula (1) is 2.

3. The iridium complex compound according to claim 1, wherein $X^3$ in the formula (3-1) is a sulfur atom.

4. The iridium complex compound according to claim 1, wherein $X^1$ and $X^2$ in the formula (2-1) and the formula (2-2) are each a nitrogen atom.

5. The iridium complex compound according to claim 1, wherein $L^2$, which is represented by the formula (3-1), includes the partial structure represented by the formula (4-1).

6. The iridium complex compound according to claim 1, wherein $R^1$ to $R^{21}$ and $R^{31}$ to $R^{38}$ in the formulae (2-1) to (2-3) and the formula (3-1) each independently are a hydrogen atom, an alkyl group having 1-4 carbon atoms, an aryl group having 6-18 carbon atoms (the aryl group being not an aralkyl-substituted phenyl group), a phenyl group substituted with one or more aralkyl groups having 7-16 carbon atoms, or an arylamino group having 6-15 carbon atoms, or are bonded to any adjacent one of the $R^1$ to $R^{21}$ or of the $R^{31}$ to $R^{34}$ to form an aromatic heterocyclic group.

7. The iridium complex compound according to claim 1, wherein at least two of $R^1$ to $R^9$ in the formula (2-1), at least two of $R^1$ to $R^4$ and $R^{10}$ to $R^{14}$ in the formula (2-2), and at least two of $R^1$ to $R^4$ and $R^{16}$ to $R^{20}$ in the formula (2-3) are a group other that a hydrogen atom, and at least one of $R^{31}$ to $R^{38}$ in the formula (3-1) is a group other than a hydrogen atom.

8. The iridium complex compound according to claim 7, wherein at least one of the groups other than a hydrogen atom is a phenyl group substituted with one or more aralkyl groups having 7-16 carbon atoms.

9. The iridium complex compound according to claim 1, wherein $R^3$ in the formulae (2-1) to (2-3) or $R^{33}$ in the formula (3-1) includes the substituent represented by the formula (4).

10. A process for producing the iridium complex compound according to claim 1, comprising:
reacting an iridium complex compound represented by the following formula (5) with a compound corresponding to a ligand represented by the formula (3-1) or
reacting an iridium complex compound represented by the following formula (6) with a compound corresponding to a ligand represented by any of the formulae (2-1) to (2-3),
in the presence of a sliver salt:

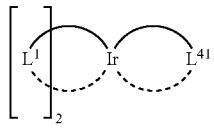

(5)

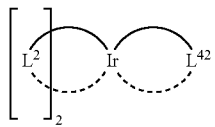

(6)

wherein $L^1$ and $L^2$ respectively represent the same ligands as the $L^1$ and $L^2$ in the formula (1), and $L^{41}$ and $L^{42}$ represent an organic ligand, with the proviso that $L^{41}$ is not a ligand represented by the formula (3-1) and $L^{42}$ is not a ligand represented by any of the formulae (2-1) to (2-3).

11. The process for production according to claim 10, wherein $L^{41}$ and $L^{42}$ in the formula (5) and the formula (6) are represented by the following formula (7-1) or formula (7-2):

(7-1)

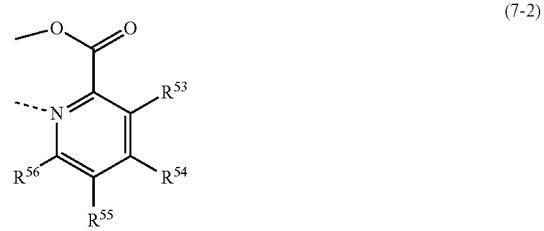

(7-2)

wherein $R^{50}$ to $R^{56}$ each independently represent a hydrogen atom, an alkyl group which has 1-20 carbon atoms and may have been substituted with one or more fluorine atoms, a phenyl group which may have been substituted with one or more alkyl groups having 1-20 carbon atoms, or a halogen atom.

12. A composition which comprises the iridium complex compound according to claim 1 and a solvent.

13. An organic electroluminescent element which comprises an anode, a cathode, and one or more organic layers disposed between the anode and the cathode, wherein at least one of the organic layers comprises the iridium complex compound according to claim 1.

14. A display device which employs the organic electroluminescent element according to claim 13.

15. An illuminator which employs the organic electroluminescent element according to claim 13.

* * * * *